US010022359B2

(12) United States Patent
Virgili-Bernado et al.

(10) Patent No.: US 10,022,359 B2
(45) Date of Patent: Jul. 17, 2018

(54) 1,9-DIAZASPIRO UNDECANE COMPOUNDS HAVING MULTIMODAL ACTIVITY AGAINST PAIN

(71) Applicant: LABORATORIOS DEL DR. ESTEVE S.A., Barcelona (ES)

(72) Inventors: Marina Virgili-Bernado, Barcelona (ES); Carlos Alegret-Molina, Barcelona (ES); Carmen Almansa-Rosales, Barcelona (ES)

(73) Assignee: ESTEVE PHARMACEUTICALS, S.A., Barcelona (ES)

( * ) Notice: Subject to any disclaimer, the term of this patent is extended or adjusted under 35 U.S.C. 154(b) by 0 days.

(21) Appl. No.: 15/527,458

(22) PCT Filed: Nov. 20, 2015

(86) PCT No.: PCT/EP2015/002333
§ 371 (c)(1),
(2) Date: May 17, 2017

(87) PCT Pub. No.: WO2016/078771
PCT Pub. Date: May 26, 2016

(65) Prior Publication Data

US 2017/0354648 A1 Dec. 14, 2017

(30) Foreign Application Priority Data

Nov. 21, 2014 (EP) .................................... 14382466

(51) Int. Cl.
*C07D 471/10* (2006.01)
*A61K 31/435* (2006.01)
*A61K 31/438* (2006.01)
*C07D 471/20* (2006.01)

(52) U.S. Cl.
CPC .......... *A61K 31/435* (2013.01); *A61K 31/438* (2013.01); *C07D 471/10* (2013.01); *C07D 471/20* (2013.01)

(58) Field of Classification Search
CPC .................................................... C07D 471/10
See application file for complete search history.

(56) References Cited

FOREIGN PATENT DOCUMENTS

| | | |
|---|---|---|
| ES | 2251317 | 4/2006 |
| WO | 2008/155132 | 12/2008 |
| WO | 2014/117920 | 8/2014 |

OTHER PUBLICATIONS

Allen, C.C., et al., Bioorganic and Medicinal Chemistry, vol. 21, p. 5707-5724, 2013.
International Search Report for PCT/FR2015/002333 dated Jan. 15, 2016.

*Primary Examiner* — Paul V Ward
(74) *Attorney, Agent, or Firm* — Hueschen and Sage

(57) ABSTRACT

The present invention relates to compounds having dual pharmacological activity towards both the sigma (σ) receptor, and the μ-opiod receptor and more particularly to 1,9-diazaspiro undecane compounds having this pharmacological activity, to processes of preparation of such compounds, to pharmaceutical compositions comprising them, and to their use in therapy, in particular for the treatment of pain.

15 Claims, No Drawings

1,9-DIAZASPIRO UNDECANE COMPOUNDS HAVING MULTIMODAL ACTIVITY AGAINST PAIN

FIELD OF THE INVENTION

The present invention relates to compounds having dual pharmacological activity towards both the sigma (σ) receptor, and the μ-opiod receptor (MOR or mu-opioid receptor) and more particularly to 1,9-diazaspiro undecane derivatives having this pharmacological activity, to processes of preparation of such compounds, to pharmaceutical compositions comprising them, and to their use in therapy, in particular for the treatment of pain.

BACKGROUND OF THE INVENTION

The adequate management of pain constitutes an important challenge, since currently available treatments provide in many cases only modest improvements, leaving many patients unrelieved [Turk D C, Wilson H D, Cahana A. Treatment of chronic non-cancer pain. *Lancet* 377, 2226-2235 (2011)]. Pain affects a big portion of the population with an estimated prevalence of around 20% and its incidence, particularly in the case of chronic pain, is increasing due to the population ageing. Additionally, pain is clearly related to comorbidities, such as depression, anxiety and insomnia, which lead to important productivity losses and socio-economical burden [Goldberg D S, McGee S J. Pain as a global public health priority. *BMC Public Health.* 11, 770 (2011)]. Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

As mentioned before, there are few available therapeutic classes for the treatment of pain, and opioids are among the most effective, especially when addressing severe pain states. They act through three different types of opioid receptors (mu, kappa and gamma) which are transmembrane G-protein coupled receptors (GPCRs). Still, the main analgesic action is attributed to the activation of the μ-opioid receptor (MOR). However, the general administration of MOR agonists is limited due to their important side effects, such as constipation, respiratory depression, tolerance, emesis and physical dependence [Meldrum, M. L. (Ed.). Opioids and Pain Relief: A Historical Perspective. Progress in Pain Research and Management, Vol 25. IASP Press, Seattle, 2003]. Additionally, MOR agonists are not optimal for the treatment of chronic pain as indicated by the diminished effectiveness of morphine against chronic pain conditions. This is especially proven for the chronic pain conditions of neuropathic or inflammatory origin, in comparison to its high potency against acute pain. The finding that chronic pain can lead to MOR down-regulation may offer a molecular basis for the relative lack of efficacy of morphine in long-term treatment settings [Dickenson, A. H., Suzuki, R. *Opioids in neuropathic pain: Clues from animal studies.* Eur J Pain 9, 113-6 (2005)]. Moreover, prolonged treatment with morphine may result in tolerance to its analgesic effects, most likely due to treatment-induced MOR down-regulation, internalization and other regulatory mechanisms. As a consequence, long-term treatment can result in substantial increases in dosing in order to maintain a clinically satisfactory pain relief, but the narrow therapeutic window of MOR agonists finally results in unacceptable side effects and poor patient compliance.

The sigma-1 ($\sigma_1$) receptor was discovered 35 years ago and initially assigned to a new subtype of the opioid family, but later on and based on the studies of the enantiomers of SKF-10,047, its independent nature was established. The first link of the $\sigma_1$ receptor to analgesia was established by Chien and Pasternak [Chien C C, Pasternak G W. Sigma antagonists potentiate opioid analgesia in rats. *Neurosci. Lett.* 190, 137-9 (1995)], who described it as an endogenous anti-opioid system, based on the finding that $\sigma_1$ receptor agonists counteracted opioid receptor mediated analgesia, while $\sigma_1$ receptor antagonists, such as haloperidol, potentiated it.

Many additional preclinical evidences have indicated a clear role of the $\sigma_1$ receptor in the treatment of pain [Zamanillo D, Romero L, Merlos M, Vela J M. Sigma-1 receptor: A new therapeutic target for pain. *Eur. J. Pharmacol,* 716, 78-93 (2013)]. The development of the $\sigma_1$ receptor knockout mice, which show no obvious phenotype and perceive normally sensory stimuli, was a key milestone in this endeavour. In physiological conditions the responses of the $\sigma_1$ receptor knockout mice to mechanical and thermal stimuli were found to be undistinguishable from WT ones but they were shown to possess a much higher resistance to develop pain behaviours than WT mice when hypersensitivity entered into play. Hence, in the $\sigma_1$ receptor knockout mice capsaicin did not induce mechanical hypersensitivity, both phases of formalin-induced pain were reduced, and cold and mechanical hypersensitivity were strongly attenuated after partial sciatic nerve ligation or after treatment with paclitaxel, which are models of neuropathic pain. Many of these actions were confirmed by the use of $\sigma_1$ receptor antagonists and led to the advancement of one compound, S1RA, into clinical trials for the treatment of different pain states. Compound S1RA exerted a substantial reduction of neuropathic pain and anhedonic state following nerve injury (i.e., neuropathic pain conditions) and, as demonstrated in an operant self-administration model, the nerve-injured mice, but not sham-operated mice, acquired the operant responding to obtain it (presumably to get pain relief), indicating that $\sigma_1$ receptor antagonism relieves neuropathic pain and also address some of the comorbidities (i.e., anhedonia, a core symptom in depression) related to pain states.

Pain is multimodal in nature, since in nearly all pain states several mediators, signaling pathways and molecular mechanisms are implicated. Consequently, monomodal therapies fail to provide complete pain relief. Currently, combining existing therapies is a common clinical practice and many efforts are directed to assess the best combination of available drugs in clinical studies [Mao J, Gold M S, Backonja M. Combination drug therapy for chronic pain: a call for more clinical studies. *J. Pain* 12, 157-166 (2011)]. Hence, there is an urgent need for innovative therapeutics to address this unmet medical need.

As mentioned previously, opioids are among the most potent analgesics but they are also responsible for various adverse effects which seriously limit their use.

Accordingly, there is still a need to find compounds that have an alternative or improved pharmacological activity in the treatment of pain, being both effective and showing the desired selectivity, and having good "drugability" properties, i.e. good pharmaceutical properties related to administration, distribution, metabolism and excretion.

Thus, the technical problem can therefore be formulated as finding compounds that have an alternative or improved pharmacological activity in the treatment of pain.

In view of the existing results of the currently available therapies and clinical practices, the present invention offers a solution by combining in a single compound binding to two different receptors relevant for the treatment of pain. This was mainly achieved by providing the compounds according to the invention that bind both to the μ-opiod receptor and to the $\sigma_1$ receptor.

SUMMARY OF THE INVENTION

In this invention a family of structurally distinct 1,9-diazaspiro undecane derivatives which have a dual pharmacological activity towards both the sigma (σ) receptor, and the μ-opiod receptor was identified thus solving the above problem of identifying alternative or improved pain treatments by offering such dual compounds.

The invention is in one aspect directed to a compound having a dual activity binding to the $\sigma_1$ receptor and the μ-opioid receptor for use in the treatment of pain.

As this invention is aimed at providing a compound or a chemically related series of compounds which act as dual ligands of the $\sigma_1$ receptor and the μ-opioid receptor it is a very preferred embodiment if the compound has a binding expressed as $K_i$ which is preferably <1000 nM for both receptors, more preferably <500 nM, even more preferably <100 nM.

The invention is directed in a main aspect to a compound of general formula (I), (I)

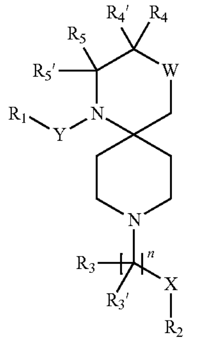

wherein $R_1$, $R_2$, $R_3$, $R_{3'}$, $R_4$, $R_{4'}$, $R_{5'}$ $R_{5'}$, W, X, Y and n are as defined below in the detailed description.

DETAILED DESCRIPTION OF THE INVENTION

The invention is directed to a family of structurally distinct 1,9-diazaspiro undecane derivatives which have a dual pharmacological activity towards both the sigma (σ) receptor and the μ-opiod receptor, thus solving the above problem of identifying alternative or improved pain treatments by offering such dual compounds.

The invention is in one aspect directed to a compound having a dual activity binding to the $\sigma_1$ receptor and the μ-opioid receptor for use in the treatment of pain.

As this invention is aimed at providing a compound or a chemically related series of compounds which act as dual ligands of the $\sigma_1$ receptor and the μ-opioid receptor it is a preferred embodiment if the compound has a binding expressed as $K_i$ which is preferably <1000 nM for both receptors, more preferably <500 nM, even more preferably <100 nM.

The applicant has surprisingly found that the problem on which the present invention is based can be solved by using a multimodal balanced analgesic approach combining two different synergistic activities in a single drug (i.e., dual ligands which are bifunctional and bind to μ-opioid receptor and to $\sigma_1$ receptor), thereby enhancing the opioid analgesia through the $\sigma_1$activation without increasing the undesirable side effects. This supports the therapeutic value of a dual MOR/$\sigma_1$ receptor compound whereby the $\sigma_1$ receptor binding component acts as an intrinsic adjuvant of the MOR binding component.

This solution offered the advantage that the two mechanisms complement each other in order to treat pain and chronic pain using lower and better tolerated doses needed based on the potentiation of analgesia but avoiding the adverse events of μ opioid receptor agonists.

A dual compound that possess binding to both the μ-opiod receptor and to the $\sigma_1$ receptor shows a highly valuable therapeutic potential by achieving an outstanding analgesia (enhanced in respect to the potency of the opioid component alone) with a reduced side-effect profile (safety margin increased compared to that of the opioid component alone) versus existing opioid therapies.

Advantageously, the dual compounds according to the present invention would in addition show one or more the following functionalities: $\sigma_1$ receptor antagonism and μ-opioid receptor agonism. It has to be noted, though, that both functionalities "antagonism" and "agonism" are also subdivided in their effect into subfunctionalities like partial agonism or inverse agonism. Accordingly, the functionalities of the dual compound should be considered within a relatively broad bandwidth.

An antagonist on one of the named receptors blocks or dampens agonist-mediated responses. Known subfunctionalities are neutral antagonists or inverse agonists.

An agonist on one of the named receptors increases the activity of the receptor above its basal level. Known subfunctionalities are full agonists, or partial agonists.

In addition, the two mechanisms complement each other since MOR agonists are only marginally effective in the treatment of neuropathic pain, while $\sigma_1$ receptor antagonists show outstanding effects in preclinical neuropathic pain models. Thus, the $\sigma_1$ receptor component adds unique analgesic actions in opioid-resistant pain. Finally, the dual approach has clear advantages over MOR agonists in the treatment of chronic pain as lower and better tolerated doses would be needed based on the potentiation of analgesia but not of the adverse events of MOR agonists.

A further advantage of using designed multiple ligands is a lower risk of drug-drug interactions compared to cocktails or multi-component drugs, thus involving simpler pharmacokinetics and less variability among patients. Additionally, this approach may improve patient compliance and broaden the therapeutic application in relation to monomechanistic drugs, by addressing more complex aetiologies. It is also seen as a way of improving the R&D output obtained using the "one drug-one target" approach, which has been questioned over the last years [Bornot A, Bauer U, Brown A, Firth M, Hellawell C, Engkvist O. Systematic Exploration of Dual-Acting Modulators from a Combined Medicinal Chemistry and Biology Perspective. *J. Med. Chem,* 56, 1197-1210 (2013)].

In a particular aspect, the present invention is directed to compounds of general formula (I):

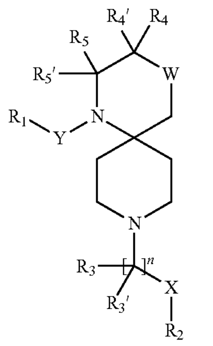

(I)

wherein n is 1, 2, 3, 4, 5 or 6;

W is $—CR_wR_{w'}—$ or —O—;

X is a bond, —C(O)— or $—CR_6R_{6'}—$;

Y is a bond or —C(O)—;

$R_1$ is substituted or unsubstituted cycloalkyl, substituted or unsubstituted aryl, substituted or unsubstituted heterocyclyl, substituted or unsubstituted alkylaryl, substituted or unsubstituted alkylheterocyclyl or substituted or unsubstituted alkylcycloalkyl;

$R_2$ is substituted or unsubstituted cycloalkyl, substituted or unsubstituted aryl or substituted or unsubstituted heterocyclyl;

$R_w$ and $R_{w'}$ are independently selected from hydrogen, halogen, $—OR_{10}$, substituted or unsubstituted $C_{1-6}$ alkyl, substituted or unsubstituted $C_{2-6}$ alkenyl, substituted or unsubstituted $C_{2-6}$ alkynyl, haloalkyl, haloalkoxy, $—C(O)OR_{10}$, $—C(O)NR_{10}R_{10'}$, $—NR_{10}C(O)R_{10'}$ and $—NR_{10}R_{10'''}$;

wherein $R_{10}$, $R_{10'}$ and $R_{10''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{10'''}$ is selected from hydrogen, unsubstituted $C_{1-6}$ alkyl, unsubstituted $C_{2-6}$ alkenyl, unsubstituted $C_{2-6}$ alkynyl and -Boc;

$R_3$ and $R_{3'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_4$ and $R_{4'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, $—C(O)OR_8$ and $—C(O)NR_8R_{8'}$;

wherein $R_8$ and $R_{8'}$ are independently selected from hydrogen, unsubstituted $C_{1-6}$ alkyl, unsubstituted $C_{2-6}$ alkenyl and unsubstituted $C_{2-6}$ alkynyl;

alternatively, $R_4$ and $R_{4'}$ may form, together with the carbon to which they are attached, a substituted or unsubstituted $C_{3-8}$ cycloalkyl;

$R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, $—C(O)OR_9$ and $—C(O)NR_9R_{9'}$;

wherein $R_9$ and $R_{9'}$ are independently selected from hydrogen, unsubstituted $C_{1-6}$ alkyl, unsubstituted $C_{2-6}$ alkenyl, and unsubstituted $C_{2-6}$ alkynyl;

$R_6$ and $R_{6'}$ are independently selected from hydrogen, halogen, $—OR_7$, substituted or unsubstituted $C_{1-6}$ alkyl, substituted or unsubstituted $C_{2-6}$ alkenyl, substituted or unsubstituted $C_{2-6}$ alkynyl, $—O(O)OR_7$, $—C(O)NR_7R_{7'}$, $—NR_7C(O)R_{7'}$ and $—NR_7R_{7'''}$;

wherein $R_7$, $R_{7'}$ and $R_{7''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{7'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In one embodiment the following proviso is applying:

$—Y—R_1$ is not benzyl when $—(CR_3R_{3'})_n—X—R_2$ is benzyl.

In another embodiment the following proviso is applying:

when $Y—R_1$ and $—(CR_3R_{3'})_n—X—R_2$ are both unsubstituted benzyl, then none of $R_4$ and $R_{4'}$ may be hydrogen or substituted or unsubstituted methyl while the other is hydrogen.

In the context of this invention, alkyl is understood as meaning saturated, linear or branched hydrocarbons, which may be unsubstituted or substituted once or several times. It encompasses e.g. $—CH_3$ and $—CH_2—CH_3$. In these radicals, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4-, or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-5}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc. Preferably alkyl is understood in the context of this invention as $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-6}$alkyl like methyl, ethyl, propyl or butyl.

Alkenyl is understood as meaning unsaturated, linear or branched hydrocarbons, which may be unsubstituted or substituted once or several times. It encompasses groups like e.g. $—CH{=}CH—CH_3$. The alkenyl radicals are preferably vinyl (ethenyl), allyl (2-propenyl). Preferably in the context of this invention alkenyl is $C_{2-10}$-alkenyl or $C_{2-8}$-alkenyl like ethylene, propylene, butylene, pentylene, hexylene, heptylene or octylene; or is $C_{2-6}$-alkenyl like ethylene, propylene, butylene, pentylene, or hexylene; or is $C_{2-4}$-alkenyl, like ethylene, propylene, or butylenes.

Alkynyl is understood as meaning unsaturated, linear or branched hydrocarbons, which may be unsubstituted or substituted once or several times. It encompasses groups like e.g. $—C{\equiv}C—CH_3$ (1-propinyl). Preferably alkynyl in the context of this invention is $C_{2-10}$-alkynyl or $C_{2-8}$-alkynyl like ethyne, propyne, butyene, pentyne, hexyne, heptyne, or octyne; or is $C_{2-6}$-alkynyl like ethyne, propyne, butyene, pentyne, or hexyne; or is $C_{2-4}$-alkynyl like ethyne, propyne, butyene, pentyne, or hexyne.

In the context of this invention cycloalkyl is understood as meaning saturated and unsaturated (but not aromatic) cyclic hydrocarbons (without a heteroatom in the ring), which can be unsubstituted or once or several times substituted. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. Examples are cyclopropyl, 2-methylcyclopropyl, cyclopropylmethyl, cyclobutyl, cyclopentyl, cyclopentylmethyl, cyclohexyl, cycloheptyl, cyclooctyl, and also adamantly. Preferably in the context of this invention cycloalkyl is $C_{3-8}$cycloalkyl like cyclopropyl, cyclobutyl, cyclopentyl, cyclohexyl, cycloheptyl, or cyclooctyl; or is $C_{3-7}$cycloalkyl like cyclopropyl, cyclobutyl, cyclopentyl, cyclohexyl, or cycloheptyl; or is $C_{3-6}$cycloalkyl like cyclopropyl, cyclobutyl, cyclopentyl or cyclohexyl, especially cyclopentyl or cyclohexyl.

In connection with alkyl (also in alkylaryl, alkylheterocyclyl or alkylcycloalkyl), alkenyl, alkynyl and O-alkyl—unless defined otherwise—the term substituted in the context of this invention is understood as meaning replacement of at least one hydrogen radical on a carbon atom by halogen (F, Cl, Br, I), —$NR_cR_{c'''}$, —$SR_c$, —$S(O)R_c$, —$S(O)_2R_c$, —$OR_c$, —$C(O)OR_c$, —CN, —$C(O)NR_cR_c$, haloalkyl, haloalkoxy or —$OC_{1-4}$alkyl being unsubstituted or substituted by one or more of —$OR_c$ or halogen (F, Cl, I, Br), being $R_c$ one of $R_{11}$ or $R_{13}$, (being $R_{c'}$ one of $R_{11'}$ or $R_{13'}$, being $R_{c''}$ one of $R_{11''}$ or $R_{13''}$, being $R_{c'''}$ one of $R_{11'''}$ or $R_{13''}$), wherein $R_1$ to $R_{13''''}$ as well as $R_w$ and $R_{w'}$ are as defined in the description, and wherein when different radicals $R_1$ to $R_{13''''}$ as well as $R_w$ and $R_{w'}$ are present simultaneously in Formula I they may be identical or different.

More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. —CH(OH)—CH═CH—$CHCl_2$.

In the context of this invention haloalkyl is understood as meaning an alkyl being substituted once or several times by a halogen (selected from F, Cl, Br, I). It encompasses e.g. —$CH_2Cl$, —$CH_2F$, —$CHCl_2$, —$CHF_2$, —$CCl_3$, —$CF_3$ and —$CH_2$—$CHCl_2$. Preferably haloalkyl is understood in the context of this invention as halogen-substituted $C_{1-4}$-alkyl representing halogen substituted C1-, C2-, C3- or C4-alkyl. The halogen-substituted alkyl radicals are thus preferably methyl, ethyl, propyl, and butyl. Preferred examples include —$CH_2Cl$, —$CH_2F$, —$CHCl_2$, —$CHF_2$, and —$CF_3$.

In the context of this invention haloalkoxy is understood as meaning an —O-alkyl being substituted once or several times by a halogen (selected from F, Cl, Br, I). It encompasses e.g. —$OCH_2Cl$, —$OCH_2F$, —$OCHCl_2$, —$OCHF_2$, —$OCCl_3$, —$OCF_3$ and —$OCH_2$—$OHCl_2$. Preferably haloalkyl is understood in the context of this invention as halogen-substituted —$OC_{1-4}$-alkyl representing halogen substituted C1-, C2-, C3- or C4-alkoxy. The halogen-substituted alkyl radicals are thus preferably O-methyl, O-ethyl, O-propyl, and O-butyl. Preferred examples include —$OCH_2Cl$, —$OCH_2F$, —$OCHCl_2$, —$OCHF_2$, and —$OCF_3$.

Most preferably in connection with alkyl (also in alkylaryl, alkylheterocyclyl or alkylcycloalkyl), alkenyl, alkynyl or O-alkyl, substituted is understood in the context of this invention that any alkyl (also in alkylaryl, alkylheterocyclyl or alkylcycloalkyl), alkenyl, alkynyl or O-alkyl which is substituted is substituted with one or more of halogen (F, Cl, Br, I), —CN, haloalkyl, haloalkoxy or —$OC_{1-4}$alkyl being unsubstituted or substituted by one or more of —$OR_c$ or halogen (F, Cl, I, Br), being $R_c$ one of $R_{11}$ or $R_{13}$, (being $R_{c'}$ one of $R_{11'}$ or $R_{13'}$; being $R_{c''}$ one of $R_{11''}$ or $R_{13''}$; being $R_{c'''}$ one of $R_{11'''}$ or $R_{13'''}$), wherein $R_1$ to $R_{13''''}$ as well as $R_w$ and $R_{w'}$ are as defined in the description, and wherein when different radicals $R_1$ to $R_{13''''}$ as well as $R_w$ and $R_{w'}$ are present simultaneously in Formula I they may be identical or different.

Aryl is understood as meaning ring systems with at least one aromatic ring but without heteroatoms even in only one of the rings. Examples are phenyl, naphthyl, fluoranthenyl, fluorenyl, tetralinyl or indanyl, in particular 9H-fluorenyl or anthracenyl radicals, which can be unsubstituted or once or several times substituted. Most preferably aryl is understood in the context of this invention as phenyl, naphthyl or anthracenyl, preferably is phenyl.

In the context of this invention alkylaryl is understood as meaning an aryl group (see above) being connected to another atom through a $C_{1-6}$-alkyl (see above) which may be branched or linear and is unsubstituted or substituted once or several times. Preferably alkylaryl is understood as meaning an aryl group (see above) being connected to another atom through 1 to 4 (—$CH_2$—) groups. Most preferably alkylaryl is benzyl (i.e. —$CH_2$-phenyl).

In the context of this invention alkylheterocyclyl is understood as meaning an heterocyclyl group being connected to another atom through a $C_{1-6}$-alkyl (see above) which may be branched or linear and is unsubstituted or substituted once or several times. Preferably alkylheterocyclyl is understood as meaning an heterocyclyl group (see above) being connected to another atom through 1 to 4 (—$CH_2$—) groups. Most preferably alkylheterocyclyl is —$CH_2$-pyridine.

In the context of this invention alkylcycloalkyl is understood as meaning an cycloalkyl group being connected to another atom through a $C_{1-6}$-alkyl (see above) which may be branched or linear and is unsubstituted or substituted once or several times.

Preferably alkylcycloalkyl is understood as meaning an cycloalkyl group (see above) being connected to another atom through 1 to 4 (—$CH_2$—) groups. Most preferably alkylcycloalkyl is —$CH_2$-cyclopropyl.

A heterocyclyl radical or group (also called heterocyclyl hereinafter) is understood as meaning heterocyclic ring systems, with at least one saturated or unsaturated ring which contains one or more heteroatoms from the group consisting of nitrogen, oxygen and/or sulfur in the ring. A heterocyclic group can also be substituted once or several times.

Examples include non-aromatic heterocyclyls such as tetrahydropyrane, oxazepane, morpholine, piperidine, pyrrolidine as well as heteroaryls such as furan, benzofuran, thiophene, benzothiophene, pyrrole, pyridine, pyrimidine, pyrazine, quinoline, isoquinoline, phthalazine, thiazole, benzothiazole, indole, benzotriazole, carbazole and quinazoline.

Subgroups inside the heterocyclyls as understood herein include heteroaryls and non-aromatic heterocyclyls.

- the heteroaryl (being equivalent to heteroaromatic radicals or aromatic heterocyclyls) is an aromatic heterocyclic ring system of one or more rings of which at least one aromatic ring contains one or more heteroatoms from the group consisting of nitrogen, oxygen and/or sulfur in the ring; preferably is an aromatic heterocyclic ring system of one or two rings of which at least one aromatic ring contains one or more heteroatoms from the group consisting of nitrogen, oxygen and/or sulfur in the ring, more preferably is selected from furan, benzofuran, thiophene, benzothiophene, pyrrole, pyridine, pyrimidine, pyrazine, quinoline, isoquinoline, phthalazine, benzothiazole, indole, benzotriazole, carbazole, quinazoline, thiazole, imidazole, pyrazole, oxazole, thiophene and benzimidazole;

the non-aromatic heterocyclyl is a heterocyclic ring system of one or more rings of which at least one ring—with this (or these) ring(s) then not being aromatic—contains one or more heteroatoms from the group consisting of nitrogen, oxygen and/or sulfur in the ring; preferably is a heterocyclic ring system of one or two rings of which one or both rings with this one or two rings then not being aromatic—contain/s one or more heteroatoms from the group consisting of nitrogen, oxygen and/or sulfur in the ring, more preferably is selected from oxazepam, pyrrolidine, piperidine, piperazine, tetrahydropyran, morpholine, indoline, oxopyrrolidine, benzodioxane, especially is benzodioxane, morpholine, tetrahydropyran, piperidine, oxopyrrolidine, and pyrrolidine.

Preferably in the context of this invention heterocyclyl is defined as a heterocyclic ring system of one or more saturated or unsaturated rings of which at least one ring contains one or more heteroatoms from the group consisting of nitrogen, oxygen and/or sulfur in the ring. Preferably it is a heterocyclic ring system of one or two saturated or unsaturated rings of which at least one ring contains one or more heteroatoms from the group consisting of nitrogen, oxygen and/or sulfur in the ring.

Preferred examples of heterocyclyls include oxazepan, pyrrolidine, imidazole, oxadiazole, tetrazole, pyridine, pyrimidine, piperidine, piperazine, benzofuran, benzimidazole, indazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyrane, pyrazole, imidazole, piperidine, thiophene, indole, benzimidazole, pyrrolo[2,3b] pyridine, benzoxazole, oxopyrrolidine, pyrimidine, oxazepane and pyrrolidine.

In the context of this invention oxopyrrolidine is understood as meaning pyrrolidin-2-one.

In connection with aromatic heterocyclyls (heteroaryls), non-aromatic heterocyclyls, aryls and cycloalkyls, when a ring system falls within two or more of the above cycle definitions simultaneously, then the ring system is defined first as an aromatic heterocyclyl (heteroaryl) if at least one aromatic ring contains a heteroatom. If no aromatic ring contains a heteroatom, then the ring system is defined as a non-aromatic heterocyclyl if at least one non-aromatic ring contains a heteroatom. If no non-aromatic ring contains a heteroatom, then the ring system is defined as an aryl if it contains at least one aryl cycle. If no aryl is present, then the ring system is defined as a cycloalkyl if at least one non-aromatic cyclic hydrocarbon is present.

Preferably, the aryl is a monocyclic aryl.

Preferably, the heteroaryl is a monocyclic heteroaryl.

Preferably, the non-aromatic heterocyclyl is a monocyclic non-aromatic heterocyclyl.

Preferably, the cycloalkyl is a monocyclic cycloalkyl.

In connection with aryl (including alkyl-aryl), cycloalkyl (including alkyl-cycloalkyl), or heterocyclyl (including alkyl-heterocyclyl), substituted is understood—unless defined otherwise—as meaning substitution of the ring-system of the aryl or alkyl-aryl, cycloalkyl or alkyl-cycloalkyl; heterocyclyl or alkyl-heterocyclyl with one or more of halogen (F, Cl, Br, I), —$R_c$, —$OR_c$, —CN, —$NO_2$, —$NR_cR_{c'''}$, —C(O)$OR_c$, $NR_cC(O)R_{c'}$, —C(O)$NR_cR_{c'}$, —$NR_cS(O)_2R_{c'}$, =O, —$OCH_2CH_2OH$, —$NR_cC(O)NR_{c'}R_{c''}$, —$S(O)_2NR_cR_{c'}$, —$NR_cS(O)_2NR_{c'}R_{c''}$, haloalkyl, haloalkoxy, —$SR_c$, —S(O)$R_c$, —$S(O)_2R_c$ or $C(CH_3)OR_c$; $NR_cR_{c'''}$, with $R_c$ and $R_{c'''}$ independently being either H or a saturated or unsaturated, linear or branched, substituted or unsubstituted $C_{1-6}$-alkyl; a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted S—$C_{1-6}$-alkyl; a saturated or unsaturated, linear or branched, substituted or unsubstituted —O(O)—$C_{1-6}$-alkyl-group; a saturated or unsaturated, linear or branched, substituted or unsubstituted —C(O)—O—$C_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl, being $R_c$ one of $R_{11}$ or $R_{12}$, (being $R_{c'}$ one of $R_{11'}$ or $R_{12'}$; being $R_{c''}$ one of $R_{11''}$ or $R_{12''}$; being $R_{c'''}$ one of $R_{11'''}$ or $R_{12'''}$), wherein $R_1$ to $R_{13'''}$ as well as $R_w$ and $R_{w'}$ are as defined in the description, and wherein when different radicals $R_1$ to $R_{13'''}$ as well as $R_w$ and $R_{w'}$ are present simultaneously in Formula I they may be identical or different.

Most preferably in connection with aryl (including alkyl-aryl), cycloalkyl (including alkyl-cycloalkyl), or heterocyclyl (including alkyl-heterocyclyl), substituted is understood in the context of this invention that any aryl, cycloalkyl and heterocyclyl which is substituted is substituted (also in an alkylaryl, alkylcycloalkyl or alkylheterocyclyl) with one or more of halogen (F, Cl, Br, I), —$R_c$, —$OR_c$, —CN, —$NO_2$, —$NR_cR_{c'''}$, $NR_cC(O)R_{c'}$, —$NR_cS(O)_2R_{c'}$, =O, haloalkyl, haloalkoxy, or $C(CH_3)OR_c$; —$OC_{1-4}$alkyl being unsubstituted or substituted with one or more of $OR_c$ or halogen (F, Cl, I, Br), —CN, or —$C_{1-4}$alkyl being unsubstituted or substituted with one or more of $OR_c$ or halogen (F, Cl, I, Br), being $R_c$ one of $R_{11}$ or $R_{12}$, (being $R_{c'}$ one of $R_{11'}$ or $R_{12'}$; being $R_{c''}$ one of $R_{11''}$ or $R_{12''}$, being $R_{c'''}$ one of $R_{11'''}$ or $R_{12'''}$), wherein $R_1$ to $R_{13'''}$ as well as $R_w$ and $R_{w'}$ are as defined in the description, and wherein when different radicals $R_1$ to $R_{13'''}$ as well as $R_w$ and $R_{w'}$ are present simultaneously in Formula I they may be identical or different.

Additionally to the above-mentioned substitutions, in connection with cycloalkyl (including alkyl-cycloalkyl), or heterocyclyl (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl; non-aromatic heterocyclyl or non aromatic alkyl-heterocyclyl with

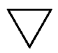

or =O;

The term "leaving group" means a molecular fragment that departs with a pair of electrons in heterolytic bond cleavage. Leaving groups can be anions or neutral molecules. Common anionic leaving groups are halides such as Cl—, Br—, and I—, and sulfonate esters, such as tosylate (TsO—) or mesylate.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes via ionic interactions.

The term "physiologically acceptable salt" means in the context of this invention any salt that is physiologically tolerated (most of the time meaning not being toxic—especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with $NH_4$, but in particular (mono)- or (di)sodium, (mono)- or (di)potassium, magnesium or calcium salts.

Physiologically acceptable salts can also be formed with anions or acids and in the context of this invention is understood as meaning salts of at least one of the compounds used according to the invention as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be present in crystalline form or in the form of free compounds like a free base or acid.

Any compound that is a solvate of a compound according to the invention like a compound according to general formula I defined above is understood to be also covered by the scope of the invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent). Especially preferred examples include hydrates and alcoholates, like methanolates or ethanolates.

Any compound that is a prodrug of a compound according to the invention like a compound according to general formula I defined above is understood to be also covered by the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon or of a nitrogen by $^{15}N$-enriched nitrogen are within the scope of this invention.

The compounds of formula (I) as well as their salts or solvates of the compounds are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts. This applies also to its solvates or prodrugs.

In a further embodiment the compound according to the invention of general formula I is a compound wherein n is 1, 2, 3, 4, 5 or 6;

W is $—CR_wR_{w'}—$ or —O—;

X is a bond, —C(O)— or $—CR_6R_{6'}—$;

Y is a bond or —C(O)—;

$R_1$ is substituted or unsubstituted cycloalkyl, substituted or unsubstituted aryl, substituted or unsubstituted heterocyclyl, substituted or unsubstituted alkylaryl, substituted or unsubstituted alkylheterocyclyl or substituted or unsubstituted alkylcycloalkyl;

wherein said cycloalkyl, aryl or heterocyclyl in $R_1$, also in alkylaryl, alkylcycloalkyl and alkylheterocyclyl, if substituted, being substituted with one or more substituents selected from halogen, $—R_{11}$, $—OR_{11}$, $—NO_2$, $—NR_{11}R_{11'''}$, $NR_{11}C(O)R_{11'}$, $—NR_{11}S(O)_2R_{11'}$, $—S(O)_2NR_{11}R_{11'}$, $—NR_{11}C(O)NR_{11'}R_{11''}$, $—SR_{11}$, $—S(O)R_{11}$, $S(O)_2R_{11}$, —CN, haloalkyl, haloalkoxy, $—C(O)OR_{11}$, $—C(O)NR_{11}R_{11'}$, $—OCH_2CH_2OH$, $—NR_{11}S(O)_2NR_{11'}R_{11''}$ and $C(CH_3)_2OR_{11}$;

additionally, cycloalkyl or heterocyclyl in $R_1$, also in alkylcycloalkyl and alkylheterocyclyl, if substituted, may also be substituted with

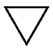

or =O;

wherein the alkyl in $R_1$, if substituted, is substituted with one or more substituents selected from $—OR_{11}$, halogen, —CN, haloalkyl, haloalkoxy, $—NR_{11}R_{11'''}$, $—SR_{11}$, $—S(O)R_{11}$, and $—S(O)_2R_{11}$;

wherein $R_{11}$, $R_{11'}$, and $R_{11''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl, unsubstituted alkylcycloalkyl, unsubstituted heterocyclyl and unsubstituted alkylheterocyclyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

$R_2$ is substituted or unsubstituted cycloalkyl, substituted or unsubstituted aryl or substituted or unsubstituted heterocyclyl;

wherein said cycloalkyl, aryl or heterocyclyl in $R_2$, if substituted, is substituted with one or more substituents selected from halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$OCH_2CH_2OH$, —$NR_{12}S(O)_2NR_{12'}R_{12''}$ and $C(CH_3)_2OR_{12}$;

additionally, cycloalkyl or heterocyclyl in $R_2$, if substituted, may also be substituted with

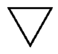

or ═O;

wherein $R_{12}$, $R_{12'}$ and $R_{12''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl, unsubstituted alkylcycloalkyl, unsubstituted heterocyclyl and unsubstituted alkylheterocyclyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

$R_w$ and $R_{w'}$ are independently selected from hydrogen, halogen, —$OR_{10}$, substituted or unsubstituted $C_{1-6}$ alkyl, substituted or unsubstituted $C_{2-6}$ alkenyl, substituted or unsubstituted $C_{2-6}$ alkynyl, haloalkyl, haloalkoxy, —$C(O)OR_{10}$, —$C(O)NR_{10}R_{10'}$, —$NR_{10}C(O)R_{10'}$ and —$NR_{10}R_{10'''}$;

wherein $R_{10}$, $R_{10'}$ and $R_{10''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{10'''}$ is selected from hydrogen, unsubstituted $C_{1-6}$ alkyl, unsubstituted $C_{2-6}$ alkenyl, unsubstituted $C_{2-6}$ alkynyl and -Boc;

$R_3$ and $R_{3'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_4$ and $R_{4'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —$C(O)OR_8$ and —$C(O)NR_8R_{8'}$;

wherein $R_8$ and $R_{8'}$ are independently selected from hydrogen, unsubstituted $C_{1-6}$ alkyl, unsubstituted $C_{2-6}$ alkenyl and unsubstituted $C_{2-6}$ alkynyl;

alternatively, $R_4$ and $R_{4'}$ may form, together with the carbon to which they are attached, a substituted or unsubstituted $C_{3-8}$ cycloalkyl;

$R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —$C(O)OR_9$, and —$C(O)NR_9R_{9'}$;

wherein $R_9$ and $R_{9'}$ are independently selected from hydrogen, unsubstituted $C_{1-6}$ alkyl, unsubstituted $C_{2-6}$ alkenyl, and unsubstituted $C_{2-6}$ alkynyl;

$R_6$ and $R_{6'}$ are independently selected from hydrogen, halogen, —$OR_7$, substituted or unsubstituted $C_{1-6}$ alkyl, substituted or unsubstituted $C_{2-6}$ alkenyl, substituted or unsubstituted $C_{2-6}$ alkynyl, —$C(O)OR_7$, —$C(O)NR_7R_{7'}$, —$NR_7C(O)R_{7'}$, and —$NR_7R_{7'''}$;

wherein $R_7$, $R_{7'}$ and $R_{7''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{7'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the alkyl, alkylene or alkynyl, other than those defined in $R_1$ or $R_2$, if substituted, is substituted with one or more substituents selected from —$OR_{13}$, halogen, —CN, haloalkyl, haloalkoxy, —$NR_{13}R_{13'''}$, —$SR_{13}$, —$S(O)R_{13}$, and —$S(O)_2R_{13}$;

wherein $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein n is 1, 2, 3, 4, 5 or 6 optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the following compound is excluded:

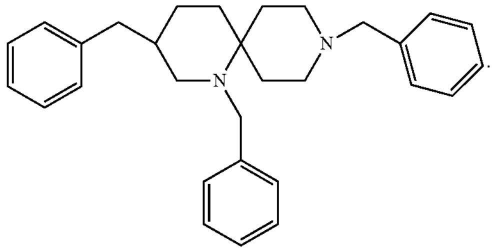 [SMILES: c1ccc(CC2CCC3(CCN(Cc4ccccc4)CC3)N(Cc3ccccc3)C2)cc1]

In a further embodiment the compound according to the invention of general formula I is a compound wherein n is 1 or 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein W is —$CR_wR_{w'}$— or —O—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein X is a bond, —C(O)— or —$CR_6R_{6'}$—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein Y is selected from bond or —C(O)—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein $R_1$ is substituted or unsubstituted cycloalkyl, substituted or unsubstituted aryl, substituted or unsubstituted heterocyclyl, substituted or unsubstituted alkylaryl, substituted or unsubstituted alkylheterocyclyl or substituted or unsubstituted alkylcycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein $R_2$ is substituted or unsubstituted cycloalkyl, substituted or unsubstituted aryl, or substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein $R_2$ is substituted or unsubstituted aryl or substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_w$ and $R_{w'}$ are independently selected from hydrogen, halogen, —$OR_{10}$, substituted or unsubstituted $C_{1-6}$ alkyl, substituted or unsubstituted $C_{2-6}$ alkenyl, substituted or unsubstituted $C_{2-6}$ alkynyl, haloalkyl, haloalkoxy, —C(O)$OR_{10}$, —C(O)$NR_{10}R_{10'}$, —$NR_{10}C(O)R_{10'}$, and —$NR_{10}R_{10'''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_w$ and $R_{w'}$ are independently selected from hydrogen, substituted or unsubstituted $C_{1-6}$alkyl, substituted or unsubstituted $C_{2-6}$ alkenyl, substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_w$ and $R_{w'}$ are independently selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_3$ and $R_{3'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl, preferably $R_3$ and $R_{3'}$ are independently selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_4$ and $R_{4'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)$OR_8$, and —C(O)$NR_8R_{8'}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_4$ and $R_{4'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl, preferably $R_4$ and $R_{4'}$ are independently selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_4$ and $R_{4'}$ may form, together with the carbon to which they are attached, a substituted or unsubstituted $C_{3-8}$ cycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)$OR_9$ and —C(O)$NR_9R_{9'}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_5$ and $R_{5'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl, preferably $R_5$ and $R_{5'}$ are independently selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_6$ and $R_{6'}$ are independently selected from hydrogen, halogen, —$OR_7$, substituted or unsubstituted $C_{1-6}$ alkyl, substituted or unsubstituted $C_{2-6}$ alkenyl, substituted or unsubstituted $C_{2-6}$ alkynyl, —C(O)$OR_7$, —C(O)$NR_7R_{7'}$, —$NR_7$C(O)$R_{7'}$ and —$NR_7R_{7'''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_6$ and $R_{6'}$ are independently selected from hydrogen, halogen, —$OR_7$, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_6$ and $R_{6'}$ are independently selected from hydrogen and —$OR_7$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_7$, $R_{7'}$ and $R_{7''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{7'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_7$, $R_{7'}$ and $R_{7''}$ are independently selected from hydrogen, unsubstituted $C_{1-6}$ alkyl, unsubstituted $C_{2-6}$ alkenyl, and unsubstituted $C_{2-6}$ alkynyl, preferably $R_7$, $R_{7'}$ and $R_{7''}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formula I is a compound wherein $R_{7'''}$ is selected from hydrogen, unsubstituted $C_{1-6}$ alkyl, unsubstituted $C_{2-6}$ alkenyl, unsubstituted $C_{2-6}$ alkynyl and -Boc, preferably $R_{7'''}$ is selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_8$ and $R_{8'}$ are independently selected from hydrogen, unsubstituted $C_{1-6}$ alkyl, unsubstituted $C_{2-6}$ alkenyl, and unsubstituted $C_{2-6}$ alkynyl, preferably $R_8$ and $R_{8'}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_9$ and $R_{9'}$ are independently selected from hydrogen, unsubstituted $C_{1-6}$ alkyl, unsubstituted $C_{2-6}$ alkenyl, and unsubstituted $C_{2-6}$ alkynyl, preferably $R_9$ and $R_{9'}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{10}$, $R_{10'}$ and $R_{10''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{10'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{10}$, $R_{10'}$ and $R_{10''}$ are independently selected from hydrogen, unsubstituted $C_{1-6}$ alkyl, unsubstituted $C_{2-6}$ alkenyl, and unsubstituted $C_{2-6}$ alkynyl, preferably $R_{10}$, $R_{10'}$ and $R_{10''}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{10'''}$ is selected from hydrogen, unsubstituted $C_{1-6}$ alkyl, unsubstituted $C_{2-6}$ alkenyl, unsubstituted $C_{2-6}$ alkynyl and -Boc, preferably $R_{10'''}$ is selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{11}$, $R_{11'}$ and $R_{11''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl, unsubstituted alkylcycloalkyl, unsubstituted heterocyclyl and unsubstituted alkylheterocyclyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{11}$, $R_{11'}$ and $R_{11''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl, unsubstituted alkylcycloalkyl, unsubstituted heterocyclyl and unsubstituted alkylheterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{11}$, $R_{11'}$ and $R_{11''}$ are independently selected from hydrogen, unsubstituted $C_{1-6}$ alkyl, unsubstituted $C_{2-6}$ alkenyl, unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc, preferably $R_{11'''}$ is selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{11}$, $R_{11'}$ and $R_{11''}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{12}$, $R_{12'}$ and $R_{12''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl, unsubstituted alkylcycloalkyl, unsubstituted heterocyclyl and unsubstituted alkylheterocyclyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{12}$, $R_{12'}$ and $R_{12''}$ are independently selected from hydrogen, unsubstituted $C_{1-6}$ alkyl, and unsubstituted $C_{2-6}$ alkenyl and unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{12}$, $R_{12'}$ and $R_{12''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl, unsubstituted alkylcycloalkyl, unsubstituted heterocyclyl and unsubstituted alkylheterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{12}$, $R_{12'}$ and $R_{12''}$ are independently selected from hydrogen, unsubstituted $C_{1-6}$ alkyl, and unsubstituted $C_{2-6}$ alkenyl and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{12}$, $R_{12'}$ and $R_{12''}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc, preferably $R_{12'''}$ is selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl, preferably $R_{13}$, $R_{13'}$ and $R_{13''}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{13'''}$ is selected from hydrogen, unsubstituted $C_{1-6}$ alkyl, unsubstituted $C_{2-6}$ alkenyl, unsubstituted $C_{2-6}$ alkynyl and -Boc, preferably $R_{13'''}$ is selected from hydrogen, unsubstituted $C_{1-6}$ alkyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein X is a bond;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein X is $—CH_2—$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein X is —CH(OH)—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein X is —C(O)— optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein Y is a bond;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein Y is —C(O)—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein n is 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein n is 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein n is 2, X is a bond and $R_2$ is substituted or unsubstituted phenyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein n is 2, X is a bond, Y is a bond and $R_2$ is substituted or unsubstituted phenyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein n is 2, X is a bond, Y is a bond, $R_1$ is substituted or unsubstituted phenyl and $R_2$ is substituted or unsubstituted phenyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_1$ is substituted or unsubstituted cycloalkyl, substituted or unsubstituted aryl, substituted or unsubstituted heterocyclyl, substituted or unsubstituted alkylaryl, substituted or unsubstituted alkylheterocyclyl and substituted or unsubstituted alkylcycloalkyl;

wherein the alkyl is $C_{1-6}$ alkyl like methyl, ethyl, propyl, butyl, pentyl, hexyl, isopropyl, or 2-methylpropyl, more preferably the alkyl is methyl or ethyl;

and/or the $C_{1-6}$ alkyl is preferably selected from methyl, ethyl, propyl, butyl, pentyl, hexyl, isopropyl, or 2-methylpropyl, preferably the $C_{1-6}$ alkyl is methyl or ethyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or the aryl is selected from phenyl, naphthyl, or anthracene; preferably is naphthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, thiazole, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocyclyl is pyridine or thiazole;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl, more preferably the cycloalkyl is cyclopropyl;

and/or $R_2$ is substituted or unsubstituted cycloalkyl, substituted or unsubstituted aryl, substituted or unsubstituted heterocyclyl;

wherein the aryl is selected from phenyl, naphthyl, or anthracene; preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocyclyl is pyridine;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_w$ and $R_{w'}$ are independently selected from hydrogen, halogen, —$OR_{10}$, substituted or unsubstituted $C_{1-6}$ alkyl, substituted or unsubstituted $C_{2-6}$ alkenyl, substituted or unsubstituted $C_{2-6}$ alkynyl, haloalkyl, haloalkoxy, —C(O)$OR_{10}$, —C(O)$NR_{10}R_{10'}$, —$NR_{10}C(O)R_{10'}$, —$NR_{10}R_{10'''}$;

wherein the alkyl is $C_{1-6}$ alkyl like methyl, ethyl, propyl, butyl, pentyl, hexyl, isopropyl, 2-methylpropyl, isopentyl or 3-pentanyl;

and/or the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_3$ and $R_{3'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl;

wherein the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_4$ and $R_{4'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)$OR_8$, —C(O)$NR_8R_{8'}$;

wherein the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_4$ and $R_{4'}$ may form, together with the carbon to which they are attached, a substituted or unsubstituted $C_{3-8}$ cycloalkyl; wherein the $C_{3-8}$ cycloalkyl is preferably selected from cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the heterocyclyl is cyclopropyl;

and/or $R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)O$R_9$, —C(O)N$R_9R_{9'}$;

wherein the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_6$ and $R_{6'}$ are independently selected from hydrogen, halogen, —O$R_7$, substituted or unsubstituted $C_{1-6}$ alkyl, substituted or unsubstituted $C_{2-6}$ alkenyl, substituted or unsubstituted $C_{2-6}$ alkynyl, —C(O)O$R_7$, —C(O)N$R_7R_{7'}$, —N$R_7$C(O)$R_{7'}$, —N$R_7R_{7''''}$;

wherein the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_7$, $R_{7'}$ and $R_{7''}$ are independently selected from hydrogen, unsubstituted $C_{1-6}$ alkyl, unsubstituted $C_{2-6}$ alkenyl, and unsubstituted $C_{2-6}$ alkynyl;

$R_{7''''}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_8$ and $R_{8'}$ are independently selected from hydrogen, unsubstituted $C_{1-6}$ alkyl, unsubstituted $C_{2-6}$ alkenyl, and unsubstituted $C_{2-6}$ alkynyl;

wherein the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_9$ and $R_{9'}$ are independently selected from hydrogen, unsubstituted $C_{1-6}$ alkyl, unsubstituted $C_{2-6}$ alkenyl, and unsubstituted $C_{2-6}$ alkynyl;

wherein the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_{10}$, $R_{10'}$ and $R_{10''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{10}$ is selected from hydrogen, unsubstituted $C_{1-6}$ alkyl, unsubstituted $C_{2-6}$ alkenyl, unsubstituted $C_{2-6}$ alkynyl and -Boc; wherein the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_{11}$, $R_{11'}$ and $R_{11''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl or unsubstituted alkylaryl, unsubstituted cycloalkyl or unsubstituted alkylcycloalkyl, unsubstituted heterocyclyl and unsubstituted alkylheterocyclyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the alkyl is $C_{1-6}$ alkyl like methyl, ethyl, propyl, butyl, pentyl, hexyl, isopropyl, 2-methylpropyl, isopentyl or 3-pentanyl, more preferably the alkyl is methyl;

and/or the $C_{1-6}$ alkyl is preferably selected from methyl, ethyl, propyl, butyl, pentyl, hexyl, isopropyl, or 2-methylpropyl, preferably the $C_{1-6}$ alkyl is methyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or the aryl is selected from phenyl, naphthyl, or anthracene; preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_{12}$, $R_{12'}$ and $R_{12''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl or unsubstituted alkylaryl, unsubstituted cycloalkyl or unsubstituted alkylcycloalkyl, unsubstituted heterocyclyl and unsubstituted alkylheterocyclyl;

$R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the alkyl is $C_{1-6}$ alkyl like methyl, ethyl, propyl, butyl, pentyl, hexyl, isopropyl, 2-methylpropyl, isopentyl or 3-pentanyl, more preferably the alkyl is methyl;

and/or the $C_{1-6}$ alkyl is preferably selected from methyl, ethyl, propyl, butyl, pentyl, hexyl, isopropyl, or 2-methylpropyl, preferably the $C_{1-6}$ alkyl is methyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or the aryl is selected from phenyl, naphthyl, or anthracene; preferably is phenyl; and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl;

$R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or n is 1, 2, 3, 4, 5 or 6, preferably n is 1 or 2;

and/or

X is a bond, —C(O)— or —$CR_6R_{6'}$—;

and/or

W is —$CR_wR_{w'}$— or —O—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_1$ as defined in any of the embodiments, the alkyl is $C_{1-6}$ alkyl like methyl, ethyl, propyl, butyl, pentyl, hexyl, isopropyl, or 2-methylpropyl, more preferably the alkyl is methyl or ethyl;

and/or the $C_{1-6}$ alkyl is preferably selected from methyl, ethyl, propyl, butyl, pentyl, hexyl, isopropyl, or 2-methylpropyl, preferably the $C_{1-6}$ alkyl is methyl or ethyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or the aryl is selected from phenyl, naphthyl, or anthracene; preferably is naphthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocyclyl is pyridine or thiazole;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl, more preferably the cycloalkyl is cyclopropyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_2$ as defined in any of the embodiments, the aryl is selected from phenyl, naphthyl, or anthracene; preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocyclyl is pyridine;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_w$ and $R_{w'}$ as defined in any of the embodiments, the alkyl is $C_{1-6}$ alkyl like methyl, ethyl, propyl, butyl, pentyl, hexyl, isopropyl, 2-methylpropyl, isopentyl or 3-pentanyl;

and/or the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_3$ and $R_{3'}$ as defined in any of the embodiments, the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_4$ and $R_{4'}$ as defined in any of the embodiments, the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_4$ and $R_{4'}$ as defined in any of the embodiments, the $C_{3-8}$ cycloalkyl is preferably selected from cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the heterocyclyl is cyclopropyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_5$ and $R_{5'}$ as defined in any of the embodiments, the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_6$ and $R_{6'}$ as defined in any of the embodiments, the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_7$, $R_{7'}$, $R_{7''}$ and $R_{7'''}$ as defined in any of the embodiments, the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_8$ and $R_{8'}$ as defined in any of the embodiments, the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_9$ and $R_{9'}$ as defined in any of the embodiments, the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_{10}$, $R_{10'}$, $R_{10''}$ and $R_{10'}$ as defined in any of the embodiments, the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_{11}$, $R_{11'}$, $R_{11''}$ and $R_{11'''}$ as defined in any of the embodiments, the alkyl is $C_{1-6}$ alkyl like methyl, ethyl, propyl, butyl, pentyl, hexyl, isopropyl, 2-methylpropyl, isopentyl or 3-pentanyl, more preferably the alkyl is methyl;

and/or the $C_{1-6}$ alkyl is preferably selected from methyl, ethyl, propyl, butyl, pentyl, hexyl, isopropyl, or 2-methylpropyl, preferably the $C_{1-6}$ alkyl is methyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or the aryl is selected from phenyl, naphthyl, or anthracene; preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_{12}$, $R_{12'}$, $R_{12''}$ and $R_{12'''}$ as defined in any of the embodiments, the alkyl is $C_{1-6}$ alkyl like methyl, ethyl, propyl, butyl, pentyl, hexyl, isopropyl, 2-methylpropyl, isopentyl or 3-pentanyl, more preferably the alkyl is methyl;

and/or the $C_{1-6}$ alkyl is preferably selected from methyl, ethyl, propyl, butyl, pentyl, hexyl, isopropyl, or 2-methylpropyl, preferably the $C_{1-6}$ alkyl is methyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or the aryl is selected from phenyl, naphthyl, or anthracene; preferably is phenyl; and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_{13}$, $R_{13'}$, $R_{13''}$ and $R_{13'''}$ as defined in any of the embodiments, the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein n is 1, 2, 3, 4, 5 or 6, preferably n is 1 or 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein X is a bond, —C(O)— or —$CR_6R_{6'}$—, preferably X is a bond;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein X is a bond, —C(O)— or —$CR_6R_{6'}$—, preferably X is a —$CR_6R_{6'}$—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein X is a bond, —C(O)— or —$CR_6R_{6'}$—, preferably X is a —C(O)—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein W is —$CR_wR_{w'}$— or —O—, preferably W is —O—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein W is —$CR_wR_{w'}$— or —O—, preferably W is —$CR_w R_{w'}$—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment $R_1$ is a substituted or unsubstituted group selected from phenyl, benzyl, phenethyl, pyridine, —$CH_2$-pyridine, thiazole, cyclopropyl and —$CH_2$-cyclopropyl;

In another preferred embodiment $R_1$ is a substituted or unsubstituted group selected from phenyl, benzyl, pyridine, —$CH_2$-pyridine and thiazole;

In a most preferred embodiment $R_1$ is substituted or unsubstituted phenyl, substituted or unsubstituted benzyl or substituted or unsubstituted pyridine;

In a preferred embodiment $R_2$ is a substituted or unsubstituted phenyl or pyridine;

In a preferred embodiment $R_3$ and $R_{3'}$ are both hydrogen;

In a preferred embodiment $R_4$ and $R_{4'}$ are both hydrogen;

In a preferred embodiment $R_5$ and $R_{5'}$ are both hydrogen;

In a preferred embodiment $R_6$ is selected from hydrogen and hydroxy;

In another preferred embodiment $R_{6'}$ is hydrogen;

In another preferred embodiment $R_6$ is hydroxy and $R_{6'}$ is hydrogen;

In another preferred embodiment $R_6$ and $R_{6'}$ are both hydrogen;

In a preferred embodiment $R_7$ is hydrogen;

In another preferred embodiment $R_{11}$ is selected from hydrogen and unsubstituted methyl;

In another preferred embodiment $R_{11'}$ is unsubstituted methyl;

In another preferred embodiment $R_{11}$ is hydrogen while $R_{11'}$ is unsubstituted methyl;

In another preferred embodiment $R_{12}$ is selected from hydrogen and substituted methyl;

In another preferred embodiment $R_{12'}$ is unsubstituted methyl;

In another preferred embodiment $R_{12}$ is hydrogen while $R_{12'}$ unsubstituted methyl;

In a preferred embodiment $R_w$ and $R_{w'}$ are hydrogen;

In another preferred embodiment n is 1 or 2;

In another preferred embodiment

W is —O—;

In another preferred embodiment

W is —$CH_2$—;

In another preferred embodiment

X is a bond, —C(O)—, —$CH_2$—, or —CH(OH)—;

In another preferred embodiment

X is a bond or —$CH_2$—;

In another preferred embodiment

X is a bond;

In another preferred embodiment

X is —$CH_2$—;

In another preferred embodiment

X is —CH(OH)—;

In another preferred embodiment

X is —C(O)—;

In another preferred embodiment

Y is a bond or —C(O)—;

In another preferred embodiment

Y is a bond;

In another preferred embodiment

Y is —C(O)—;

In an particular embodiment the halogen is fluorine, chlorine, iodine or bromine;

In an particular embodiment the halogen is fluorine or chlorine;

In a preferred further embodiment, the compounds of the general formula I are selected from

| EX | Chemical name |
|---|---|
| 1 | 9-benzyl-1-phenyl-1,9-diazaspiro[5.5]undecane |
| 2 | 3-(9-benzyl-1,9-diazaspiro[5.5]undecan-1-yl)phenol |
| 3 | 9-phenethyl-1-phenyl-1,9-diazaspiro[5.5]undecane |
| 4 | 9-benzyl-1-(3-methoxyphenyl)-1,9-diazaspiro[5.5]undecane |
| 5 | 9-benzyl-1-phenyl-4-oxa-1,9-diazaspiro[5.5]undecane |
| 6 | 1-benzyl-9-phenethyl-4-oxa-1,9-diazaspiro[5.5]undecane |
| 7 | 9-phenethyl-1-phenyl-4-oxa-1,9-diazaspiro[5.5]undecane |
| 8 | cyclopropyl(9-phenethyl-4-oxa-1,9-diazaspiro[5.5]undecan-1-yl)methanone |
| 9 | (9-benzyl-4-oxa-1,9-diazaspiro[5.5]undecan-1-yl)(phenyl)methanone |
| 10 | (9-phenethyl-4-oxa-1,9-diazaspiro[5.5]undecan-1-yl)(phenyl)methanone |
| 11 | (9-phenethyl-4-oxa-1,9-diazaspiro[5.5]undecan-1-yl)(pyridin-2-yl)methanone |
| 12 | (9-phenethyl-4-oxa-1,9-diazaspiro[5.5]undecan-1-yl)(thiazol-2-yl)methanone |
| 13 | (9-phenethyl-4-oxa-1,9-diazaspiro[5.5]undecan-1-yl)(pyridin-4-yl)methanone |
| 14 | (9-phenethyl-4-oxa-1,9-diazaspiro[5.5]undecan-1-yl)(pyridin-3-yl)methanone |
| 15 | (2-fluorophenyl)(9-phenethyl-4-oxa-1,9-diazaspiro[5.5]undecan-1-yl)methanone |
| 16 | (9-phenethyl-4-oxa-1,9-diazaspiro[5.5]undecan-1-yl)(thiazol-4-yl)methanone |
| 17 | 1-(9-phenethyl-4-oxa-1,9-diazaspiro[5.5]undecan-1-yl)-2-(pyridin-2-yl)ethanone |
| 18 | 2-cyclopropyl-1-(9-phenethyl-4-oxa-1,9-diazaspiro[5.5]undecan-1-yl)ethanone |
| 19 | 1-(9-phenethyl-4-oxa-1,9-diazaspiro[5.5]undecan-1-yl)-2-(pyridin-4-yl)ethanone |
| 20 | (9-phenethyl-4-oxa-1,9-diazaspiro[5.5]undecan-1-yl)(thiazol-5-yl)methanone |
| 21 | 1-(9-phenethyl-4-oxa-1,9-diazaspiro[5.5]undecan-1-yl)-2-phenylethanone |
| 22 | 1-(9-phenethyl-4-oxa-1,9-diazaspiro[5.5]undecan-1-yl)-2-(pyridin-3-yl)ethanone |
| 23 | N-(3-(2-(1-phenyl-4-oxa-1,9-diazaspiro[5.5]undecan-9-yl)ethyl)phenyl)acetamide |
| 24 | 9-phenethyl-1-(pyridin-4-ylmethyl)-4-oxa-1,9-diazaspiro[5.5]undecane |
| 25 | 1-(3-methoxybenzyl)-9-phenethyl-4-oxa-1,9-diazaspiro[5.5]undecane |

-continued

| EX | Chemical name |
|---|---|
| 26 | 9-phenethyl-1-(pyridin-2-ylmethyl)-4-oxa-1,9-diazaspiro[5.5]undecane |
| 27 | 9-phenethyl-1-(pyridin-3-ylmethyl)-4-oxa-1,9-diazaspiro[5.5]undecane |
| 28 | 2-((9-phenethyl-4-oxa-1,9-diazaspiro[5.5]undecan-1-yl)methyl)phenol |
| 29 | 1,9-diphenethyl-4-oxa-1,9-diazaspiro[5.5]undecane |
| 30 | 1-(4-methoxybenzyl)-9-phenethyl-4-oxa-1,9-diazaspiro[5.5]undecane |
| 31 | 1-((3-fluoropyridin-4-yl)methyl)-9-phenethyl-4-oxa-1,9-diazaspiro[5.5]undecane |
| 32 | N-(3-((9-phenethyl-4-oxa-1,9-diazaspiro[5.5]undecan-1-yl)methyl)phenyl)methanesulfonamide |
| 33 | N-(4-((9-phenethyl-4-oxa-1,9-diazaspiro[5.5]undecan-1-yl)methyl)phenyl)acetamide |
| 34 | 1-benzyl-9-(2-(pyridin-2-yl)ethyl)-4-oxa-1,9-diazaspiro[5.5]undecane |
| 35 | 1-benzyl-9-(2-methoxyphenethyl)-4-oxa-1,9-diazaspiro[5.5]undecane |
| 36 | 1-benzyl-9-(3-methoxyphenethyl)-4-oxa-1,9-diazaspiro[5.5]undecane |
| 37 | 1-benzyl-9-(4-methoxyphenethyl)-4-oxa-1,9-diazaspiro[5.5]undecane |
| 38 | 1-benzyl-9-(2-(pyridin-3-yl)ethyl)-4-oxa-1,9-diazaspiro[5.5]undecane |
| 39 | 1-benzyl-9-(2-(pyridin-4-yl)ethyl)-4-oxa-1,9-diazaspiro[5.5]undecane |
| 40 | 1-phenyl-9-(2-(pyridin-2-yl)ethyl)-4-oxa-1,9-diazaspiro[5.5]undecane |
| 41 | 9-(3-nitrophenethyl)-1-phenyl-4-oxa-1,9-diazaspiro[5.5]undecane |
| 42 | 1-phenyl-9-(2-(pyridin-3-yl)ethyl)-4-oxa-1,9-diazaspiro[5.5]undecane |
| 43 | 1-phenyl-9-(2-(6-(trifluoromethyl)pyridin-3-yl)ethyl)-4-oxa-1,9-diazaspiro[5.5]undecane |
| 44 | 1-phenyl-9-(2-(pyridin-4-yl)ethyl)-4-oxa-1,9-diazaspiro[5.5]undecane |
| 45 | 2-(1-benzoyl-4-oxa-1,9-diazaspiro[5.5]undecan-9-yl)-1-phenylethanone |
| 46 | 3-(2-(1-benzyl-4-oxa-1,9-diazaspiro[5.5]undecan-9-yl)ethyl)phenol |
| 47 | 3-((9-phenethyl-4-oxa-1,9-diazaspiro[5.5]undecan-1-yl)methyl)phenol |
| 48 | 4-(2-(1-benzyl-4-oxa-1,9-diazaspiro[5.5]undecan-9-yl)ethyl)phenol |
| 49 | 2-(2-(1-benzyl-4-oxa-1,9-diazaspiro[5.5]undecan-9-yl)ethyl)phenol |
| 50 | 3-(2-(1-phenyl-4-oxa-1,9-diazaspiro[5.5]undecan-9-yl)ethyl)aniline |
| 51 | (9-(2-hydroxy-2-phenylethyl)-4-oxa-1,9-diazaspiro[5.5]undecan-1-yl)(phenyl)methanone |
| 52 | 1-(cyclopropylmethyl)-9-phenethyl-4-oxa-1,9-diazaspiro[5.5]undecane |

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I, is a compound wherein W is —$CH_2$— the compound being exemplified in examples 1-4;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I, is a compound wherein W is —O— the compound being exemplified in examples 5-52;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I, is a compound wherein X is a bond and n is 1, the compound being exemplified in examples 1, 2, 4, 5, 9;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I, is a compound wherein X is a bond and n is 2, the compound being exemplified in examples 3, 6, 7, 8, 10 to 44, 46 to 50 and 52;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I, is a compound wherein X is —$CH_2$— and n is 1, the compound being exemplified in examples 3, 6, 7, 8, 10 to 44, 46 to 50 and 52;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I is a compound wherein Y is a bond the compound being exemplified in examples 1 to 7, 23 to 44, 46 to 50 and 52;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I is a compound wherein Y is —C(O)— the compound being exemplified in examples 8 to 22. 45 and 51;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I is a compound wherein n is 1 and X is a bond, the compound exemplified in from examples 1, 2, 4, 5, 9;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I is a compound wherein n is 2, the compound being exemplified in examples 3, 6 to 8, 10 to 44, 46 to 50 and 52;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I is a compound wherein n is 2, X is a bond and $R_2$ is substituted or unsubstituted phenyl, the compound being exemplified in examples 3, 6 to 8, 10 to 33, 35 to 37, 41, 46 to 50 and 52 optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I is a compound wherein n is 2, X is a bond, Y is a bond, $R_1$ is substituted or unsubstituted phenyl or substituted or unsubstituted benzyl and $R_2$ is substituted or unsubstituted phenyl, the compound being exemplified in examples 3, 6, 7, 23, 25, 28, 30, 32, 33, 35 to 37, 41 and 46 to 50;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I is a compound wherein n is 2, X is a bond, Y is a bond, $R_1$ is substituted or unsubstituted phenyl or substituted or unsubstituted benzyl and $R_2$ is substituted or unsubstituted pyridine, the compound being exemplified in examples 34, 38 to 40 and 42 to 44;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I, $R_1$ is substituted or unsubstituted cycloalkyl, substituted or unsubstituted aryl, substituted or unsubstituted heterocyclyl, substituted or unsubstituted alkylaryl, substituted or unsubstituted alkylheterocyclyl and substituted or unsubstituted alkylcycloalkyl;

wherein said cycloalkyl, aryl or heterocyclyl in $R_1$, also in alkylaryl, alkylcycloalkyl and alkylheterocyclyl, if substituted, being substituted with one or more substituents selected from halogen, $—R_{11}$, $—OR_{11}$, $—NO_2$, $—NR_{11}R_{11'''}$, $NR_{11}C(O)R_{11'}$, $—NR_{11}S(O)_2R_{11'}$, $—S(O)_2NR_{11}R_{11'}$, $—NR_{11}C(O)NR_{11'}R_{11''}$, $—SR_{11}$, $—S(O)R_{11}$, $S(O)_2R_{11}$, —CN, haloalkyl, haloalkoxy, $—C(O)OR_{11}$, $—C(O)NR_{11}R_{11'}$, $—OCH_2CH_2OH$, $—NR_{11}S(O)_2NR_{11'}R_{11''}$ and $C(CH_3)_2OR_{11}$;

additionally, cycloalkyl or heterocyclyl in $R_1$, also in alkylcycloalkyl and alkylheterocyclyl, if substituted, may also be substituted with

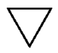

or =O;

wherein the alkyl in $R_1$, if substituted, is substituted with one or more substituents selected from $—OR_{11}$, halogen, —CN, haloalkyl, haloalkoxy, $—NR_{11}R_{11'''}$, $—SR_{11}$, $—S(O)R_{11}$, and $—S(O)_2R_{11}$;

wherein $R_{11}$, $R_{11'}$ and $R_{11''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl or unsubstituted alkylaryl, unsubstituted cycloalkyl or unsubstituted alkylcycloalkyl, unsubstituted heterocyclyl and unsubstituted alkylheterocyclyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the compound according to the invention of general formula I, $R_2$ is substituted or unsubstituted cycloalkyl, substituted or unsubstituted aryl, substituted or unsubstituted heterocyclyl;

wherein said cycloalkyl, aryl or heterocyclyl in $R_2$, if substituted, is substituted with one or more substituents selected from halogen, $—R_{12}$, $—OR_{12}$, $—NO_2$, $—NR_{12}R_{12'''}$, $NR_{12}C(O)R_{12'}$, $—NR_{12}S(O)_2R_{12'}$, $—S(O)_2NR_{12}R_{12'}$, $—NR_{12}C(O)NR_{12'}R_{12''}$, $—SR_{12}$, $—S(O)R_{12}$, $S(O)_2R_{12}$, —CN, haloalkyl, haloalkoxy, $—C(O)OR_{12}$, $—C(O)NR_{12}R_{12'}$, $—OCH_2CH_2OH$, $—NR_{12}S(O)_2NR_{12'}R_{12''}$ and $C(CH_3)_2OR_{12}$;

additionally, cycloalkyl or heterocyclyl in $R_2$, if substituted, may also be substituted with

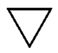

or =O;

wherein $R_{12}$, $R_{12'}$ and $R_{12''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl or unsubstituted alkylaryl, unsubstituted cycloalkyl or unsubstituted alkylcycloalkyl, unsubstituted heterocyclyl and unsubstituted alkylheterocyclyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the compound according to the invention of general formula I, $R_2$ is substituted or unsubstituted cycloalkyl, substituted or unsubstituted aryl, substituted or unsubstituted heterocyclyl;

wherein said cycloalkyl, aryl or heterocyclyl in $R_2$, if substituted, is substituted with one or more substituents selected from halogen, $—R_{12}$, $—OR_{12}$, $—NO_2$, $—NR_{12}R_{12'''}$, $NR_{12}C(O)R_{12'}$, $—NR_{12}S(O)_2R_{12'}$, $—S(O)_2NR_{12}R_{12'}$, $—NR_{12}C(O)NR_{12'}R_{12''}$, $—SR_{12}$, $—S(O)R_{12}$, $S(O)_2R_{12}$, —CN, haloalkyl, haloalkoxy, $—C(O)OR_{12}$, $—C(O)NR_{12}R_{12'}$, $—OCH_2CH_2OH$, $—NR_{12}S(O)_2NR_{12'}R_{12''}$ and $C(CH_3)_2OR_{12}$;

additionally, cycloalkyl or heterocyclyl in $R_2$, if substituted, may also be substituted with

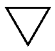

or =O;

wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the compound according to the invention of general formula I, the alkyl, alkylene or alkynyl, other than those defined in $R_1$ or $R_2$, if substituted, is substituted with one or more substituents selected from $—OR_{13}$, halogen, —CN, haloalkyl, haloalkoxy, $—NR_{13}R_{13'''}$, $—SR_{13}$, $—S(O)R_{13}$, and $—S(O)_2R_{13}$;

wherein $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I and in relation to $R_1$ of any of the previous embodiments, the cycloalkyl, aryl or heterocyclyl in $R_1$, also in alkylaryl, alkylcycloalkyl and alkylheterocyclyl, if substituted, being substituted with one or more substituents selected from halogen, $—R_{11}$, $—OR_{11}$, $—NO_2$, $—NR_{11}R_{11'''}$, $NR_{11}C(O)R_{11'}$, $—NR_{11}S(O)_2R_{11'}$, $—S(O)_2NR_{11}R_{11'}$, $—NR_{11}C(O)NR_{11'}R_{11''}$, $—SR_{11}$, $—S(O)R_{11}$, $S(O)_2R_{11}$, —CN, haloalkyl, haloalkoxy, $—C(O)OR_{11}$, $—C(O)NR_{11}R_{11'}$, $—OCH_2CH_2OH$, $—NR_{11}S(O)_2NR_{11'}R_{11''}$ and $C(CH_3)_2OR_{11}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I and in relation to $R_1$ of any of the previous embodiments, the cycloalkyl or heterocyclyl in $R_1$, also in alkylcycloalkyl and alkylheterocyclyl, if substituted, may also be substituted with

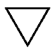

or =O;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I and in relation to $R_1$ of any of the previous embodiments, the alkyl in $R_1$, if substituted, is substituted with one or more substituents selected from $—OR_{11}$, halogen, —CN, haloalkyl, haloalkoxy, $—NR_{11}R_{11'''}$, $—SR_{11}$, $—S(O)R_{11}$, and $—S(O)_2R_{11}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I and in relation to $R_2$ of any of the previous embodiments, the cycloalkyl, aryl or heterocyclyl in $R_2$, if substituted, is substituted with one or more substituents selected from halogen, $—R_{12}$, $—OR_{12}$, $—NO_2$, $—NR_{12}R_{12'''}$, $NR_{12}C(O)R_{12'}$, $—NR_{12}S(O)_2R_{12'}$, $—S(O)_2NR_{12}R_{12'}$, $—NR_{12}C(O)NR_{12'}R_{12''}$, $—SR_{12}$, $—S(O)R_{12}$, $S(O)_2R_{12}$, —CN, haloalkyl, haloalkoxy, $—C(O)OR_{12}$, $—C(O)NR_{12}R_{12'}$, $—OCH_2CH_2OH$, $—NR_{12}S(O)_2NR_{12'}R_{12''}$ and $C(CH_3)_2OR_{12}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I and in relation to $R_2$ of any of the previous embodiments, the cycloalkyl or heterocyclyl in $R_2$, if substituted, may also be substituted with

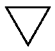

or =O;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I and in relation to alkyls other than those defined in $R_1$ or $R_2$ of any of the previous embodiments, the alkyl, alkylene or alkynyl, other than those defined in $R_1$ or $R_2$, if substituted, is substituted with one or more substituents selected from —$OR_{13}$, halogen, —CN, haloalkyl, haloalkoxy, —$NR_{13}R_{13'''}$, —$SR_{13}$, —$S(O)R_{13}$, and —$S(O)_2R_{13}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general formula I, the halogen is fluorine, chlorine, iodine or bromine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a most preferred embodiment of the compound according to the invention of general formula I, the halogen is fluorine or chlorine optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general formula I, the haloalkyl is —CF3;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the compound according to the invention of general formula I, the haloalkoxy is —OCF3;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

As this invention is aimed at providing a compound or a chemically related series of compounds which act as dual ligands of the $\sigma_1$ receptor and the μ-opiod receptor it is a very preferred embodiment in which the compounds are selected which act as dual ligands of the $\sigma_1$ receptor and the μ-opiod receptor and especially compounds which have a binding expressed as Ki which is preferably <1000 nM for both receptors, more preferably <500 nM, even more preferably <100 nM.

A further embodiment of the invention concerns compounds of general Formula (IXV"). This embodiment is herewith called EMBODIMENT A.

A 1st embodiment of EMBODIMENT A is a compound of Formula (IX")

(IX")

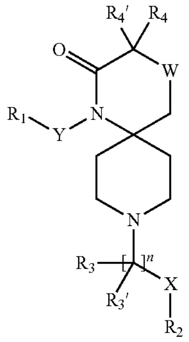

wherein n is 1, 2, 3, 4, 5 or 6

W is —$CR_wR_{w'}$— or —O—;

X is a bond, —C(O)— or —$CR_6R_{6'}$—;

Y is a bond or —C(O)—;

$R_1$ is substituted or unsubstituted cycloalkyl, substituted or unsubstituted aryl, substituted or unsubstituted heterocyclyl, substituted or unsubstituted alkylaryl, substituted or unsubstituted alkylheterocyclyl and substituted or unsubstituted alkylcycloalkyl;

wherein said cycloalkyl, aryl or heterocyclyl in $R_1$, also in alkylaryl, alkylcycloalkyl and alkylheterocyclyl, if substituted, being substituted with one or more substituents selected from halogen, —$R_{11}$, —$OR_{11}$, —$NO_2$, —$NR_{11}R_{11'''}$NR$_{11}$C(O)$R_{11'}$, —$NR_{11}S(O)_2R_{11'}$, —$S(O)_2$ $NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11''}$ and $C(CH_3)_2OR_{11}$;

additionally, cycloalkyl or heterocyclyl in $R_1$, also in alkylcycloalkyl and alkylheterocyclyl, if substituted, may also be substituted with

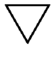

or =O;

wherein the alkyl in $R_1$, if substituted, is substituted with one or more substituents selected from —$OR_{11}$, halogen, —CN, haloalkyl, haloalkoxy, —$NR_{11}R_{11'''}$, —$SR_{11}$, —$S(O)R_{11}$, and —$S(O)_2R_{11}$;

wherein $R_{11}$, $R_{11'}$ and $R_{11''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

or

Y—$R_1$ is hydrogen;

$R_2$ is substituted or unsubstituted cycloalkyl, substituted or unsubstituted aryl, substituted or unsubstituted heterocyclyl;

wherein said cycloalkyl, aryl or heterocyclyl in $R_2$, if substituted, is substituted with one or more substituents selected from halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$OCH_2CH_2OH$, —$NR_{12}S(O)_2NR_{12'}R_{12''}$ and $C(CH_3)_2OR_{12}$;

additionally, cycloalkyl or heterocyclyl in $R_2$, if substituted, may also be substituted with

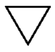

or =O;

wherein $R_{12}$, $R_{12'}$ and $R_{12''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

$R_w$ and $R_{w'}$ are independently selected from hydrogen, halogen, —$OR_{10}$, substituted or unsubstituted $C_{1-6}$ alkyl, substituted or unsubstituted $C_{2-6}$ alkenyl, substituted or unsubstituted $C_{2-6}$ alkynyl, haloalkyl, haloalkoxy, —$C(O)OR_{10}$, —$C(O)NR_{10}R_{10'}$, —$NR_{10}C(O)R_{10'}$, —$NR_{10}R_{10'''}$;

wherein $R_{10}$, $R_{10'}$ and $R_{10''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{10'''}$ is selected from hydrogen, unsubstituted $C_{1-6}$ alkyl, unsubstituted $C_{2-6}$ alkenyl, unsubstituted $C_{2-6}$ alkynyl and -Boc;

$R_3$ and $R_{3'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl;

$R_4$ and $R_{4'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —$C(O)OR_8$, —$C(O)NR_8R_{8'}$;

wherein $R_8$ and $R_{8'}$ are independently selected from hydrogen, unsubstituted $C_{1-6}$ alkyl, unsubstituted $C_{2-6}$ alkenyl, and unsubstituted $C_{2-6}$ alkynyl;

alternatively, $R_4$ and $R_{4'}$ may form, together with the carbon to which they are attached, a substituted or unsubstituted $C_{3-8}$ cycloalkyl;

$R_6$ and $R_{6'}$ are independently selected from hydrogen, halogen, —$OR_7$, substituted or unsubstituted $C_{1-6}$ alkyl, substituted or unsubstituted $C_{2-6}$ alkenyl, substituted or unsubstituted $C_{2-6}$ alkynyl, —$C(O)OR_7$, —$C(O)NR_7R_{7'}$, —$NR_7C(O)R_{7'}$, —$NR_7R_{7'''}$;

wherein $R_7$, $R_{7'}$ and $R_{7''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_7$ is selected from hydrogen, unsubstituted $C_{1-6}$ alkyl, unsubstituted $C_{2-6}$ alkenyl, unsubstituted $C_{2-6}$ alkynyl and -Boc;

wherein the alkyl, alkylene or alkynyl, other than those defined in $R_1$ or $R_2$, if substituted, is substituted with one or more substituents selected from —$OR_{13}$, halogen, —CN, haloalkyl, haloalkoxy, —$NR_{13}R_{13'''}$, —$SR_{13}$, —$S(O)R_{13}$, and —$S(O)_2R_{13}$;

wherein $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{13'''}$ is selected from hydrogen, unsubstituted $C_{1-6}$ alkyl, unsubstituted $C_{2-6}$ alkenyl, unsubstituted $C_{2-6}$ alkynyl and -Boc.

In an embodiment of this 1st embodiment of EMBODIMENT A the following proviso applies:

that

—Y—$R_1$ is not unsubstituted benzyl or hydrogen when —$(CR_3R_{3'})_n$—X—$R_2$ is unsubstituted benzyl.

In a 2nd embodiment of EMBODIMENT A according to the 1st embodiment:

n is 1 or 2;

and/or, preferably and

W is —$CR_wR_{w'}$— or —O—;

and/or, preferably and

X is a bond, —C(O)— or $CH(OR_7)$—;

and/or, preferably and

Y is a bond, or —C(O)—;

and/or, preferably and $R_1$ is substituted or unsubstituted cycloalkyl, substituted or unsubstituted aryl, substituted or unsubstituted heterocyclyl, substituted or unsubstituted alkylaryl, substituted or unsubstituted alkylheterocyclyl and substituted or unsubstituted alkylcycloalkyl;

or

—Y—$R_1$ is hydrogen;

and/or, preferably and $R_2$ is substituted or unsubstituted cycloalkyl, substituted or unsubstituted aryl, substituted or unsubstituted heterocyclyl;

and/or, preferably and $R_w$ and $R_{w'}$ are both hydrogen;

and/or, preferably and $R_3$ and $R_{3'}$ are both hydrogen;

and/or, preferably and $R_4$ and $R_{4'}$ are both hydrogen;

and/or, preferably and $R_7$ is selected from hydrogen and unsubstituted $C_{1-6}$ alkyl.

In an embodiment of this 2nd embodiment of EMBODIMENT A the following proviso applies:

that

—Y—$R_1$ is not unsubstituted benzyl or hydrogen when —$(CR_3R_{3'})_n$—X—$R_2$ is unsubstituted benzyl.

In a 3rd embodiment of EMBODIMENT A according to the 1st and 2nd embodiment:

n is 1 or 2;

W is —$CR_wR_{w'}$— or —O—;

X is a bond, —C(O)— or $CH(OR_7)$—;

Y is a bond or —C(O)—;

$R_1$ is substituted or unsubstituted cycloalkyl, substituted or unsubstituted aryl, substituted or unsubstituted heterocyclyl, substituted or unsubstituted alkylaryl, substituted or unsubstituted alkylheterocyclyl and substituted or unsubstituted alkylcycloalkyl;

or

Y—$R_1$ is hydrogen;

$R_2$ is substituted or unsubstituted cycloalkyl, substituted or unsubstituted aryl, substituted or unsubstituted heterocyclyl;

$R_w$ and $R_{w'}$ are both hydrogen;

$R_3$ and $R_{3'}$ are both hydrogen;

$R_4$ and $R_{4'}$ are both hydrogen;

$R_7$ is selected from hydrogen and unsubstituted $C_{1-6}$ alkyl.

In an embodiment of this $3^{rd}$ embodiment of EMBODIMENT A the following proviso applies:

that

—Y—$R_1$ is not unsubstituted benzyl or hydrogen when —$(CR_3R_{3'})_n$—X—$R_2$ is unsubstituted benzyl.

In a $4^{th}$ embodiment of EMBODIMENT A according to the $1^{st}$ to $3^{rd}$ embodiment:

n is 1 or 2;

W is —$CR_wR_{w'}$— or —O—;

X is a bond;

Y is a bond;

$R_1$ is substituted or unsubstituted aryl, or substituted or unsubstituted heterocyclyl, substituted or unsubstituted alkylaryl;

or

Y—$R_1$ is hydrogen;

$R_2$ is substituted or unsubstituted aryl;

$R_w$ and $R_{w'}$ are both hydrogen;

$R_3$ and $R_{3'}$ are both hydrogen;

$R_4$ and $R_{4'}$ are both hydrogen.

In an embodiment of this $4^{th}$ embodiment of EMBODIMENT A the following proviso applies:

that

—Y—$R_1$ is not unsubstituted benzyl or hydrogen when —$(CR_3R_{3'})_n$—X—$R_2$ is unsubstituted benzyl.

In a $5^{th}$ embodiment of EMBODIMENT A according to the $1^{st}$ to $4^{th}$ embodiment:

n is 2, X is a bond and $R_2$ is substituted or unsubstituted phenyl.

In a $6^{th}$ embodiment of EMBODIMENT A according to the $1^{st}$ to $5^{th}$ embodiment:

$R_1$ is substituted or unsubstituted phenyl.

In the following the phrase "compound of the invention" is used. This is to be understood as any compound according to the invention as described above according to general formula I.

The compounds of the invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention. This also applies to the compounds of EMBODIMENT A.

In general the processes are described below in the experimental part. The starting materials are commercially available or can be prepared by conventional methods.

A preferred aspect of the invention is also a process for the production of a compound according to formula I. In this process there is also the disclosure for the process of production of the compounds of EMBODIMENT A which—most often—act as intermediates in the process for the production of a compound according to formula I.

A preferred aspect of the invention is thus also a process for the production of a compound according to formula I, (I)

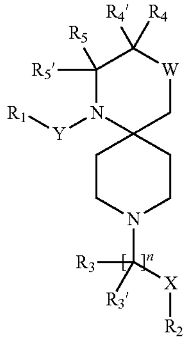

wherein n, X, Y, W, $R_1$, $R_2$, $R_3$, $R_{3'}$, $R_4$, $R_{4'}$, $R_5$ and $R_{5'}$ are as defined in the description.

In a particular embodiment there is a process for the production of a compound according to formula I (I)

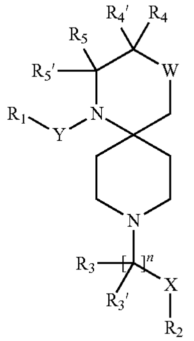

wherein n, X, Y, W, $R_1$, $R_2$, $R_3$, $R_{3'}$, $R_4$, $R_{4'}$, $R_5$ and $R_{5'}$ are as defined in the description, by reaction of a compound of formula IVH (IVH)

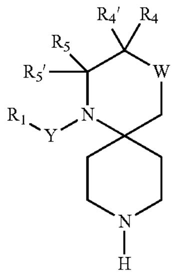

wherein $R_1$, $R_4$, $R_{4'}$, $R_5$, $R_{5'}$, W and Y have the meanings as defined above for a compound of formula (I), with a compound of formula V, VI or VII,

V

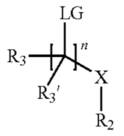

-continued

VI

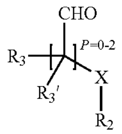

VII

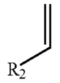

wherein $R_2$, $R_3$, $R_{3'}$, n and X have the meanings as defined above for a compound of formula (I), p represents 0, 1 or 2, and LG represents a leaving group such as halogen, mesylate, tosylate or triflate.

In another embodiment there is a process for the production of a compound according to formula I (I)

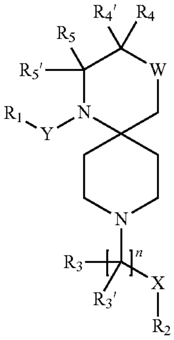

wherein n, X, Y, W, $R_1$, $R_2$, $R_3$, $R_{3'}$, $R_4$, $R_{4'}$, $R_5$ and $R_{5'}$ are as defined in the description.

by reaction of a compound of formula II (II)

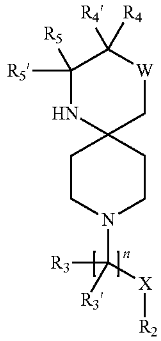

wherein $R_2$, $R_3$, $R_{3'}$, $R_4$, $R_{4'}$, $R_5$, $R_{5'}$, n, W and X have the meanings as defined above for a compound of formula (I), with a compound of formula (III)

$R_1Z$ wherein $R_1$ has the meaning as defined above for a compound of formula (I) and wherein Z represents a leaving group such as halogen, mesylate, tosylate or triflate, or an aldehyde (CHO), or alternatively it represents COOH or COV wherein V represents halogen.

In a particular embodiment there is a process for the production of a compound according to formula I (I)

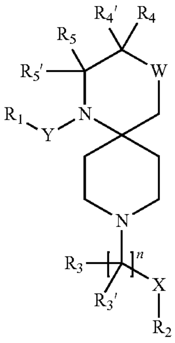

wherein n, X, Y, W, $R_1$, $R_2$, $R_3$, $R_{3'}$, $R_4$ and $R_{4'}$ are as defined in the description, and wherein $R_5$ and $R_{5'}$ are hydrogen, by reduction reaction of a compound of formula IX"

(IX")

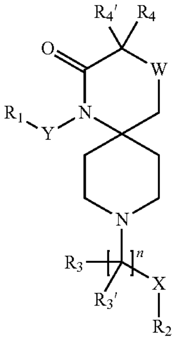

wherein $R_1$, $R_2$, $R_3$, $R_{3'}$, $R_4$, $R_{4'}$, n, W, X and Y have the meanings as defined above for a compound of formula (I).

In a particular embodiment there is a process for the production of a compound according to formula I', (I')

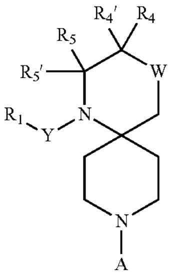

wherein A represents —$(CR_3R_{3'})_nXR_2$, hydrogen or P, wherein $R_1$, $R_2$, $R_3$, $R_{3'}$, $R_4$, $R_{4'}$, $R_5$, $R_{5'}$, n, W, X and Y have the meanings as defined above for a compound of formula (I), and P represents a suitable protecting group (preferably Boc), said process comprises reacting a compound of formula II'

(II')

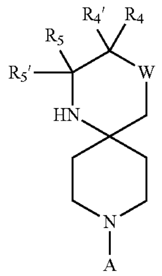

wherein A represents $-(CR_3R_{3'})_nXR_2$, hydrogen or P, wherein $R_2$, $R_3$, $R_{3'}$, $R_4$, $R_{4'}$, $R_5$, $R_{5'}$, n, W and X have the meaning as defined above for a compound of formula (I), and P represents a suitable protecting group (preferably Boc), with a compound of formula (III)

$R_1Z$ (III)

wherein $R_1$ has the meaning as defined above for a compound of formula (I), and wherein Z represents a leaving group such as halogen, mesylate, tosylate or triflate, or an aldehyde (CHO), or alternatively it represents COOH or COV wherein V represents halogen.

In another embodiment there is a process for the production of a compound according to formula IVH, (IVH)

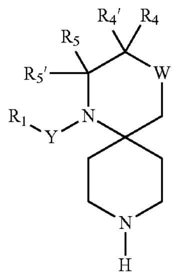

wherein $R_1$, $R_4$, $R_{4'}$, $R_5$, $R_{5'}$, W and Y have the meaning as defined above for a compound of formula (I), by deprotection of a compound of formula IVP, (IVP)

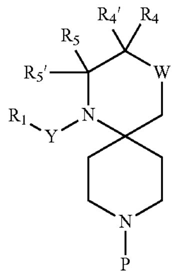

wherein $R_1$, $R_4$, $R_{4'}$, $R_5$, $R_{5'}$, W and Y have the meanings as defined above for a compound of formula (I).

In another embodiment there is a process for the production of a compound according to formula VIIIH'', (VIIIH'')

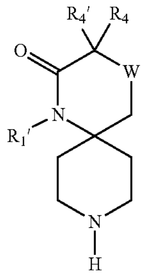

wherein $R_{1'}$ is $R_1$ or hydrogen and wherein $R_1$, $R_4$, $R_{4'}$ and W have the meanings as defined above for a compound of formula (I), by deprotection of a compound of formula VIIIP'', (VIIIP'')

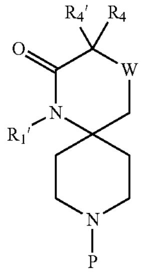

wherein $R_{1'}$ is $R_1$ or hydrogen and wherein $R_1$, $R_4$, $R_{4'}$ and W have the meanings as defined above for a compound of formula (I), and P represents a suitable protecting group (preferably Boc).

In another embodiment there is a process for the production of a compound according to formula Ib', (Ib')

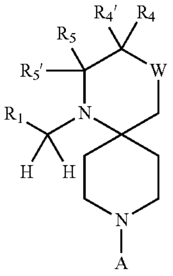

wherein A represents $-(CR_3R_{3'})_nXR_2$, hydrogen or P, and wherein $R_1$, $R_2$, $R_3$, $R_{3'}$, $R_4$, $R_{4'}$, $R_5$, $R_{5'}$, n, W and X have the meaning as defined above for a compound of formula (I), and P represents a suitable protecting group (preferably Boc), by reduction of a compound of formula (Ia')

(Ia')

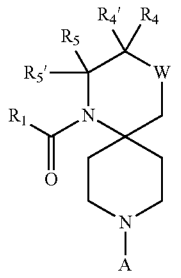

wherein A represents —$(CR_3R_{3'})_nXR_2$, hydrogen or P, and wherein $R_1$, $R_2$, $R_3$, $R_{3'}$, $R_4$, $R_{4'}$, $R_5$, $R_{5'}$, n, W and X have the meaning as defined above for a compound of formula (I), and P represents a suitable protecting group (preferably Boc), In another embodiment there is a process for the production of a compound according to formula Ic', (Ic')

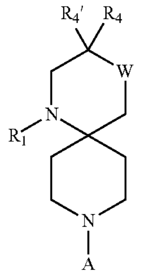

wherein A represents —$(CR_3R_{3'})_nXR_2$, hydrogen or P, and wherein $R_1$, $R_2$, $R_3$, $R_{3'}$, $R_4$, $R_{4'}$, n, W and X have the meaning as defined above for a compound of formula (I), and P represents a suitable protecting group (preferably Boc), by reduction of a compound of formula (IX')

(IX')

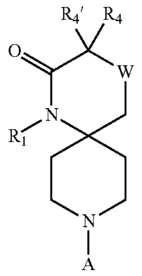

wherein A represents —$(CR_3R_{3'})_nXR_2$, hydrogen or P, and wherein $R_1$, $R_2$, $R_3$, $R_{3'}$, $R_4$, $R_{4'}$, n, W and X have the meaning as defined above for a compound of formula (I), and P represents a suitable protecting group (preferably Boc).

In a particular embodiment a compound of formula (IX')

(IX')

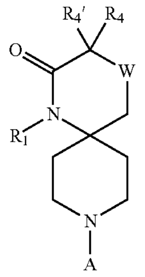

wherein A represents —$(CR_3R_{3'})_nXR_2$, hydrogen or P, wherein $R_1$, $R_2$, $R_3$, $R_{3'}$, $R_4$, $R_{4'}$, n, W and X have the meaning as defined above for a compound of formula (I), and P represents a suitable protecting group (preferably Boc), is prepared by reacting a compound of formula VIII'

(VIII')

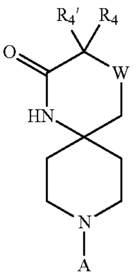

wherein A represents —$(CR_3R_{3'})_nXR_2$, hydrogen or P, wherein $R_2$, $R_3$, $R_{3'}$, $R_4$, $R_{4'}$, n, W and X have the meanings as defined above for a compound of formula (I), and P represents a suitable protecting group (preferably Boc), with a compound of formula IIIa by means of an alkylation or arylation reaction $R_1Z$ (IIIa)

wherein $R_1$ has the meaning as defined above for a compound of formula (I), and Z independently represent a leaving group such as halogen, mesylate, tosylate or triflate, and P represents a suitable protecting group (preferably Boc).

In a particular embodiment a compound of Formula (X')

(X')

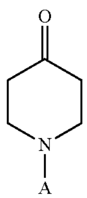

is used for the preparation of compounds of Formula (I), wherein A represents —$(CR_3R_{3'})_nXR_2$, hydrogen or P, wherein $R_2$, $R_3$, $R_{3'}$, n and X have the meaning as defined above for a compound of formula (I), and P represents a suitable protecting group (preferably Boc).

In a particular embodiment a compound of Formula (XII')

(XII')

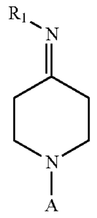

is used for the preparation of compounds of Formula (I), wherein A represents $-(CR_3R_{3'})_nXR_2$, hydrogen or P, wherein $R_1$, $R_2$, $R_3$, $R_{3'}$, $R_4$, $R_{4'}$, n, W and X have the meanings as defined above for a compound of formula (I), and P represents a suitable protecting group (preferably Boc).

In a particular embodiment a compound of Formula (XIV')

(XIV')

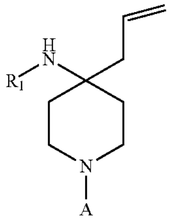

is used for the preparation of compounds of Formula (I), wherein A represents $-(CR_3R_{3'})_nXR_2$, hydrogen or P, wherein $R_1$, $R_2$, $R_3$, $R_{3'}$, $R_4$, $R_{4'}$, n, W and X have the meanings as defined above for a compound of formula (I), and P represents a suitable protecting group (preferably Boc).

In a particular embodiment a compound of Formula (XVI')

(XVI')

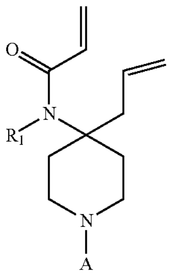

is used for the preparation of compounds of Formula (I), wherein A represents $-(CR_3R_{3'})_nXR_2$, hydrogen or P, wherein $R_1$, $R_2$, $R_3$, $R_{3'}$, $R_4$, $R_{4'}$, n, W and X have the meanings as defined above for a compound of formula (I), and P represents a suitable protecting group (preferably Boc).

In a particular embodiment a compound of Formula (IXa')

(IXa')

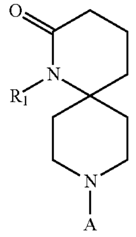

is used for the preparation of compounds of Formula (I), wherein A represents $-(CR_3R_{3'})_nXR_2$, hydrogen or P, wherein $R_1$, $R_2$, $R_3$, $R_{3'}$, $R_4$, $R_{4'}$, n, W and X have the meanings as defined above for a compound of formula (I), and P represents a suitable protecting group (preferably Boc).

In a particular embodiment a compound of Formula (XXII')

(XXII')

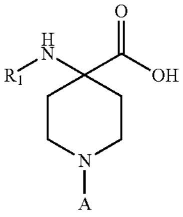

is used for the preparation of compounds of Formula (I), wherein A represents $-(CR_3R_{3'})_nXR_2$, hydrogen or P, wherein $R_1$, $R_2$, $R_3$, $R_{3'}$, $R_4$, $R_{4'}$, n, W and X have the meanings as defined above for a compound of formula (I), and P represents a suitable protecting group (preferably Boc).

In a particular embodiment a compound of Formula (XXIII')

(XXIII')

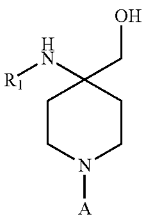

is used for the preparation of compounds of Formula (I), wherein A represents $-(CR_3R_{3'})_nXR_2$, hydrogen or P, wherein $R_1$, $R_2$, $R_3$, $R_{3'}$, $R_4$, $R_{4'}$, n, W and X have the meanings as defined above for a compound of formula (I), and P represents a suitable protecting group (preferably Boc).

In a particular embodiment a compound of Formula (IXb")

(IXb")

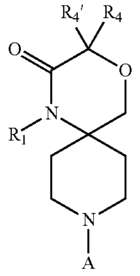

is used for the preparation of compounds of Formula (I), wherein A represents $—(CR_3R_{3'})_nXR_2$, hydrogen or P, wherein $R_1$, $R_2$, $R_3$, $R_{3'}$, $R_4$, $R_{4'}$, n, W and X have the meanings as defined above for a compound of formula (I), and P represents a suitable protecting group (preferably Boc).

In a particular embodiment a compound of Formula (XVIIa')

(XVIIa')

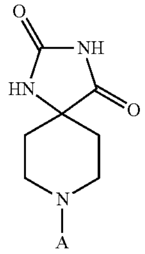

is used for the preparation of compounds of Formula (I), wherein A represents $—(CR_3R_{3'})_nXR_2$, hydrogen or P, wherein $R_1$, $R_2$, $R_3$, $R_{3'}$, $R_4$, $R_{4'}$, n, W and X have the meanings as defined above for a compound of formula (I), and P represents a suitable protecting group (preferably Boc).

In a particular embodiment a compound of Formula (XVIII')

(XVIII')

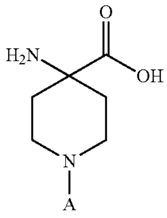

is used for the preparation of compounds of Formula (I), wherein A represents $—(CR_3R_{3'})_nXR_2$, hydrogen or P, wherein $R_1$, $R_2$, $R_3$, $R_{3'}$, $R_4$, $R_{4'}$, n, W and X have the meanings as defined above for a compound of formula (I), and P represents a suitable protecting group (preferably Boc).

In a particular embodiment a compound of Formula (XIX')

(XIX')

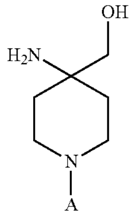

is used for the preparation of compounds of Formula (I), wherein A represents $—(CR_3R_{3'})_nXR_2$, hydrogen or P, wherein $R_1$, $R_2$, $R_3$, $R_{3'}$, $R_4$, $R_{4'}$, n, W and X have the meanings as defined above for a compound of formula (I), and P represents a suitable protecting group (preferably Boc).

In a particular embodiment a compound of Formula (VIIIa')

(VIIIa')

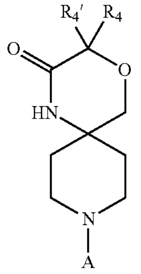

is used for the preparation of compounds of Formula (I), wherein A represents $—(CR_3R_{3'})_nXR_2$, hydrogen or P, wherein $R_1$, $R_2$, $R_3$, $R_{3'}$, $R_4$, $R_{4'}$, n, W and X have the meanings as defined above for a compound of formula (I), and P represents a suitable protecting group (preferably Boc).

In a particular embodiment a compound of Formula (IIa')

(IIa')

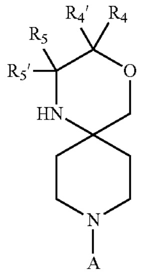

is used for the preparation of compounds of Formula (I), wherein A represents $—(CR_3R_{3'})_nXR_2$, hydrogen or P, wherein $R_1$, $R_2$, $R_3$, $R_{3'}$, $R_4$, $R_{4'}$, n, W and X have the meanings as defined above for a compound of formula (I), and P represents a suitable protecting group (preferably Boc).

In a particular embodiment a compound of Formula (IIb')

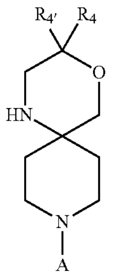

(IIb')

is used for the preparation of compounds of Formula (I), wherein A represents $-(CR_3R_{3'})_nXR_2$, hydrogen or P, wherein $R_1$, $R_2$, $R_3$, $R_{3'}$, $R_4$, $R_{4'}$, n, W and X have the meanings as defined above for a compound of formula (I), and P represents a suitable protecting group (preferably Boc).

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form of a compound of the invention is the crystalline form, including such form in pharmaceutical composition. In the case of salts and also solvates of the compounds of the invention the additional ionic and solvent moieties must also be non-toxic. The compounds of the invention may present different polymorphic forms, it is intended that the invention encompasses all such forms.

Another aspect of the invention refers to a pharmaceutical composition which comprises a compound according to the invention as described above according to general formulas I or a pharmaceutically acceptable salt or steroisomer thereof, and a pharmaceutically acceptable carrier, adjuvant or vehicle. The present invention thus provides pharmaceutical compositions comprising a compound of this invention, or a pharmaceutically acceptable salt or stereoisomers thereof together with a pharmaceutically acceptable carrier, adjuvant, or vehicle, for administration to a patient. All of this also applies to the compounds of EMBODIMENT A which could also be formulated into a pharmaceutical composition.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrups or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Another aspect of the invention refers to the use of a compound of the invention or a pharmaceutically acceptable salt or isomer thereof in the manufacture of a medicament.

Another aspect of the invention refers to a compound of the invention according as described above according to general formula I, or a pharmaceutically acceptable salt or isomer thereof, for use as a medicament for the treatment of pain. Preferably the pain is medium to severe pain, visceral pain, chronic pain, cancer pain, migraine, inflammatory pain, acute pain or neuropathic pain, allodynia or hyperalgesia. This may include mechanical allodynia or thermal hyperalgesia. All of this also applies to the compounds of EMBODIMENT A and thus applies for their use as a medicament for the treatment of pain.

Another aspect of the invention refers to the use of a compound of the invention in the manufacture of a medicament for the treatment or prophylaxis of pain.

In a preferred embodiment the pain is selected from medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

Another aspect of this invention relates to a method of treating or preventing pain which method comprises administering to a patient in need of such a treatment a therapeutically effective amount of a compound as above defined or a pharmaceutical composition thereof. Among the pain syndromes that can be treated are medium to severe pain, visceral pain, chronic pain, cancer pain, migraine, inflammatory pain, acute pain or neuropathic pain, allodynia or hyperalgesia, whereas this could also include mechanical allodynia or thermal hyperalgesia.

The present invention is illustrated below with the aid of examples. These illustrations are given solely by way of example and do not limit the general spirit of the present invention.

EXAMPLES

General Experimental Part (Methods and Equipment of the Synthesis and Analysis (I)

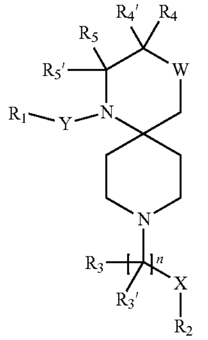

An other aspect of the invention refers to the processes for obtaining the compounds of general formula (I). Several processes have been developed for obtaining all the compounds of the invention. The different processes are summarized in Schemes 1 to 4 below.

Scheme 1

The compounds of general formula (I) can be synthesized starting from a compound of formula II, as shown in the following scheme:

Scheme 1

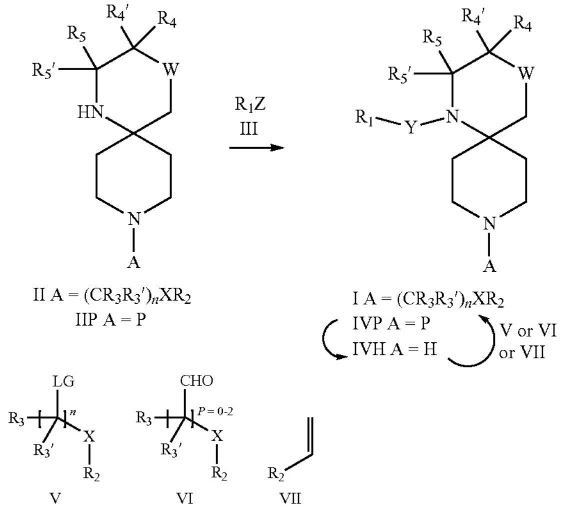

V VI VII wherein $R_1$, $R_2$, $R_3$, $R_{3'}$, $R_4$, $R_{4'}$, $R_5$, $R_{5'}$, n, W, X and Y have the meanings as defined above for a compound of formula (I), p represents 0, 1 or 2, LG represents a leaving group such as halogen, mesylate, tosylate or triflate, P represents a suitable protecting group (preferably Boc), and Z represents a leaving group such as halogen, mesylate, tosylate or triflate, or an aldehyde (CHO), or alternatively it represents COOH or COV wherein V represents halogen.

Depending on the meaning of Y, the compound of formula III can be of different nature and different reaction conditions will apply:

1) When Y represents CO, a compound of formula I is prepared by reacting a compound of formula II with an acylating agent of formula III wherein Z represents COOH or COV. When Z is COV, the reaction is carried out in a suitable solvent, such as dichloromethane, tetrahydrofuran, ethyl acetate or ethyl acetate-water mixtures; in the presence of an organic base such as triethylamine or diisopropylethylamine or an inorganic base such as $K_2OC_3$; and at a suitable temperature, preferably comprised between 0° C. and room temperature. Additionally, an activating agent such as 4-dimethylaminopyridine can be used.

When Z is COOH, the acylation reaction is carried out using a suitable coupling reagent such as N-(3-dimethylaminopropyl)-N-ethylcarbodiimide (EDC), dicyclohexylcarbodiimide (DCC), N-[(dimethylamino)-1H-1,2,3-triazolo-[4,5-b]pyridin-1-ylmethylene]-N-methylmethanaminium hexafluorophosphate N-oxide (HATU) or N,N,N,N-tetramethyl-O-(1H-benzotriazol-1-yl)uronium hexafluorophosphate (HBTU), optionally in the presence of 1-hydroxybenzotriazole, optionally in the presence of an organic base such as N-methylmorpholine or diisopropylethylamine, in a suitable solvent such as dichloromethane or dimethylformamide, and at a suitable temperature, preferably at room temperature.

2) When Y represents a bond, a compound of formula I is prepared by reacting a compound of formula II with an alkylating or arylating agent of formula III wherein Z represents a leaving group such as halogen, mesylate, tosylate or triflate, or by reacting a compound of formula II with an aldehyde of formula III wherein Z represents CHO. The following reaction conditions can be applied:

a) The alkylation reaction between a compound of formula II and an alkylating agent of formula III is carried out in a suitable solvent, such as acetonitrile, dichloromethane, 1,4-dioxane or dimethylformamide, preferably in acetonitrile; in the presence of an inorganic base such as $K_2OC_3$ or $Cs_2CO_3$, or an organic base such as triethylamine or diisopropylethylamine; at a suitable temperature comprised between room temperature and the reflux temperature, preferably heating, or alternatively, the reactions can be carried out in a microwave reactor. Additionally, an activating agent such as NaI can be used.

b) The reductive amination reaction between a compound of formula II and an aldehyde of formula III is carried out in the presence of a reductive reagent, preferably sodium triacetoxyborohydride, in an aprotic solvent, preferably tetrahydrofuran or dichloroethane, optionally in the presence of an acid, preferably acetic acid.

c) The arylation reaction between a compound of formula II and an arylating agent of formula III, wherein Z represents halogen (preferably bromo or iodo) or triflate, is carried out under catalytic conditions using a palladium or copper catalyst, optionally in the presence of a suitable ligand and a suitable base, in a suitable solvent, and at a suitable temperature, preferably heating at the reflux temperature or in a microwave reactor. When using copper catalysts such as copper(I) iodide, trans-1,2-cyclohexanediamine is the preferred ligand, potassium phosphate is used preferably as the base and 1,4-dioxane or DMF is the solvent of choice. When using palladium catalysts such as tris(dibenzylideneacetone)dipalladium(0) or palladium diacetate, 4,5-bis(diphenylphosphino)-9,9-dimethylxanthene (Xantphos) or BINAP are the preferred ligands, cesium carbonate or sodium tert-butoxide are used preferably as the base and 1,4-dioxane or toluene are the solvents of choice.

Alternatively, the group $(CR_3R_{3'})_nXR_2$ can be incorporated in the last step of the synthesis by reaction of a compound of formula IVH with a compound of formula V, VI or VII, as shown in Scheme 1. A compound of formula IVH is obtained by deprotection of a compound of formula IVP, wherein P represents a suitable protecting group, preferably Boc (tert-butoxycarbonyl). When the protecting group is Boc, the deprotection can be conducted by adding a solution of a strong acid such as HCl, in a suitable solvent such as diethyl ether, 1,4-dioxane or methanol, or with trifluoroacetic acid in dichloromethane. A compound of formula IVP is prepared from a compound of formula IIP following the same conditions described for the synthesis of compounds of formula (I).

The alkylation reaction between a compound of formula IVH (or a suitable salt such as trifluoroacetate or hydrochloride) and a compound of formula V and the reductive amination reaction between a compound of formula IVH and a compound of formula VI can be performed following the same conditions described above for the synthesis of compounds of formula (I).

The condensation reaction between a compound of general formula IVH and a compound of formula VII is preferably carried out in a suitable solvent, such as ethanol, isopropanol, n-butanol or 2-methoxyethanol, optionally in the presence of an organic base such as triethylamine or diisopropylethylamine, at a suitable temperature comprised between room temperature and the reflux temperature, preferably heating, or alternatively, the reactions can be carried out in a microwave reactor.

The compounds of general formula III, V, VI and VII wherein $R_1$, $R_2$, $R_3$, $R_{3'}$, n, p, LG, X and Z have the meanings as defined above, are commercially available or can be prepared by conventional methods described in the bibliography.

Scheme 2

Alternatively, certain compounds of general formula (I) wherein Y is a bond can be prepared by reduction of a compound of formula (I) wherein Y is CO (compounds of formula Ia), as shown in the following scheme:

Scheme 2

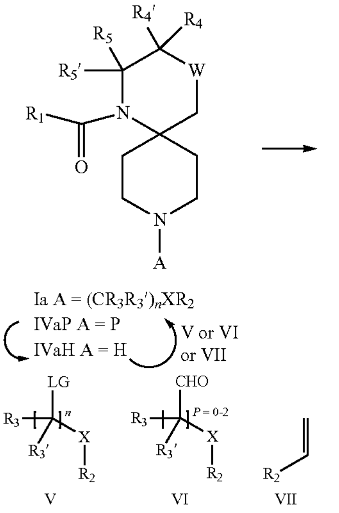

wherein $R_1$, $R_2$, $R_3$, $R_{3'}$, $R_4$, $R_{4'}$, $R_5$, $R_{5'}$, n, W and X have the meanings as defined above for a compound of formula (I), p represents 0, 1 or 2, LG represents a leaving group such as halogen, mesylate, tosylate or triflate, and P represents a suitable protecting group (preferably Boc).

The reduction reaction of a compound of formula Ia to yield a compound of formula Ib can be performed using a suitable reducing agent such as lithium aluminium hydride, borane-tetrahydrofuran complex or borane-dimethyl sulfide complex, in a suitable solvent such as tetrahydrofuran or toluene, at a suitable temperature comprised between room temperature and the reflux temperature.

Alternatively, the group $(CR_3R_{3'})_nXR_2$ may be incorporated at different stages of the synthesis. Thus, a compound of formula Ia or Ib can be prepared from a protected precursor of formula IVaP or IVbP, respectively, wherein P represents a suitable protecting group, by deprotection followed by reaction with a compound of formula V, VI or VII, under the reaction conditions described in Scheme 1.

Scheme 3

In another approach, the compounds of general formula (I) wherein Y is a bond and $R_5$ and $R_{5'}$ are hydrogen (compounds of formula Ic) can be prepared in a 2-step process starting from a compound of formula VIII, as shown in the following scheme:

Scheme 3

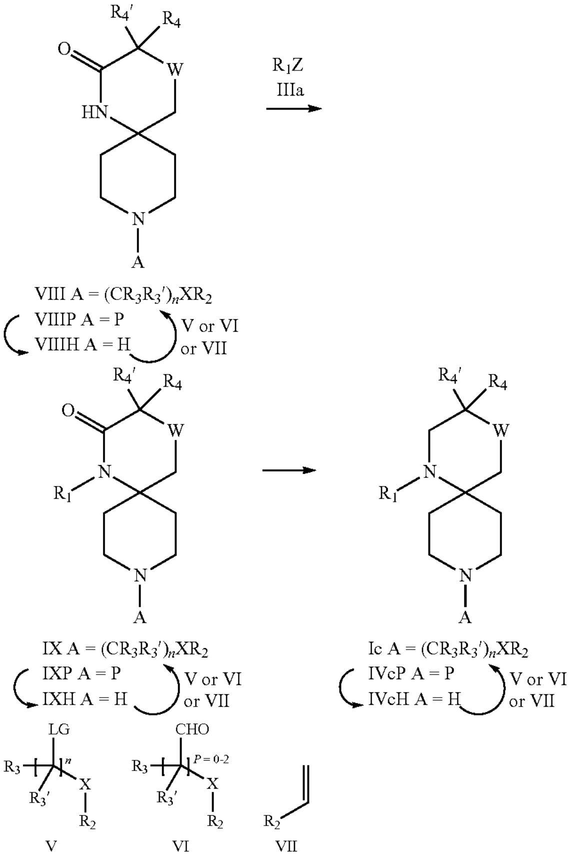

wherein $R_1$, $R_2$, $R_3$, $R_{3'}$, $R_4$, $R_{4'}$, n, W and X have the meanings as defined above for a compound of formula (I), p represents 0, 1 or 2, LG and Z independently represent a leaving group such as halogen, mesylate, tosylate or triflate, and P represents a suitable protecting group (preferably Boc).

The 2 step-process is performed as described below:

Step1: A compound of formula IX is prepared from a compound of formula VIII and a compound of formula IIIa by means of an alkylation or arylation reaction. When $R_1$ is aryl or heteroaryl, the arylation reaction is performed following the reaction conditions described in Scheme 1. Otherwise, the alkylation reaction is carried out in an aprotic solvent, preferably dimethylformamide or tetrahydrofuran, in the presence of an inorganic base such as sodium hydride, at a suitable temperature, preferably between room temperature and 80° C.

Step2: The reduction reaction of a compound of formula IX to yield a compound of formula Ic can be performed under the reaction conditions described in Scheme 2.

Alternatively, the group $(CR_3R_{3'})_nXR_2$ may be incorporated at different stages of the synthesis. Thus, a compound of formula Ic, VIII or IX can be prepared from a protected precursor of formula IVcP, VIIIP or IXP, respectively, wherein P represents a suitable protecting group, by deprotection followed by reaction with a compound of formula V, VI or VII, under the reaction conditions described in Scheme 1.

The preparation of intermediates of general formula II, IIP, VIII, VIIIP, IX and IXP is described in Scheme 4, routes A, B and C, according to the different definitions of the group W.

Scheme 4

The preparation of intermediates of general formula II, IIP, VIII, VIIIP, IX and IXP is described in the following scheme, according to the different definitions of the group W:

Scheme 4

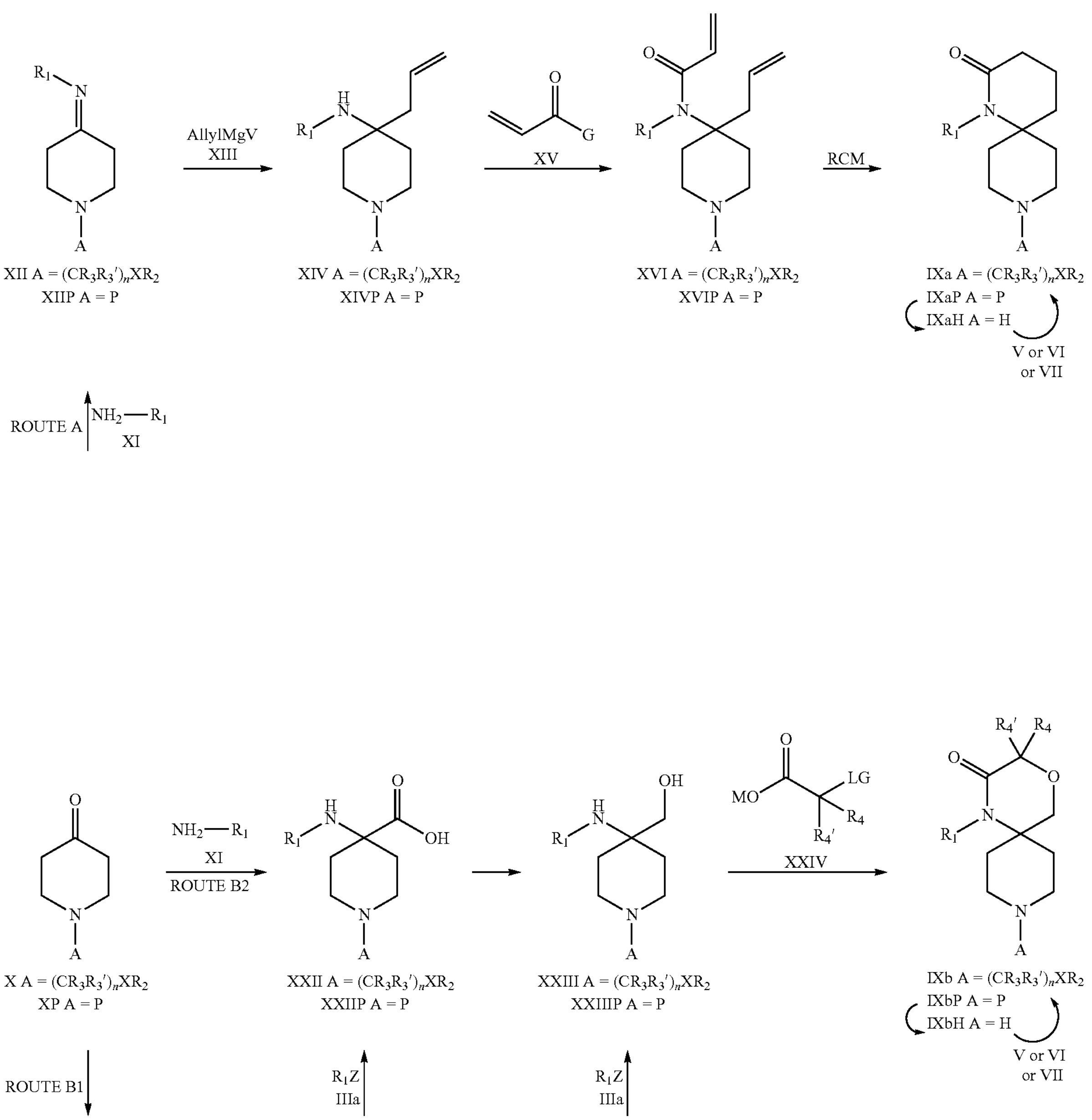

-continued

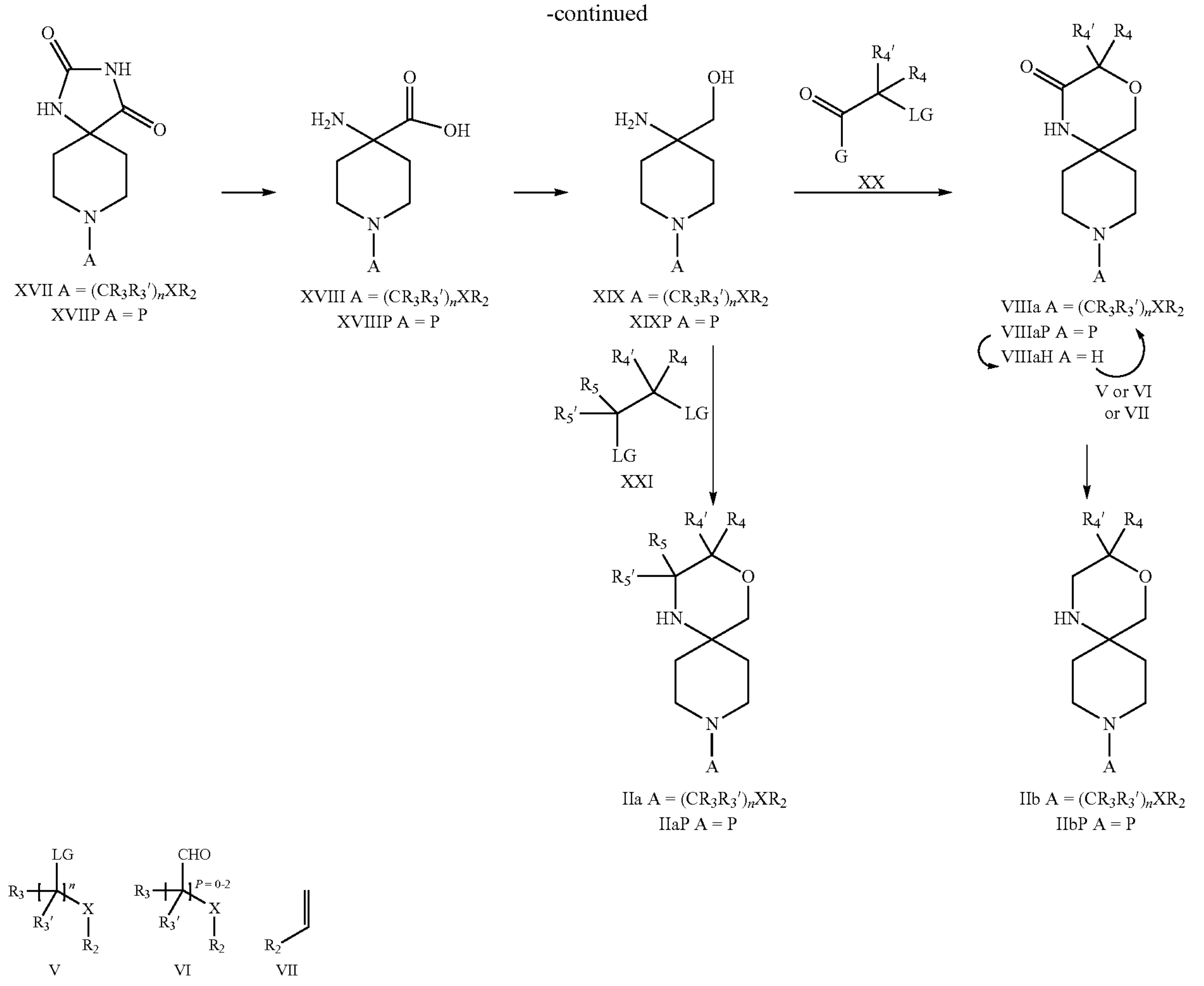

XVII A = $(CR_3R_3')_nXR_2$
XVIIP A = P

XVIII A = $(CR_3R_3')_nXR_2$
XVIIIP A = P

XIX A = $(CR_3R_3')_nXR_2$
XIXP A = P

XXI

VIIIa A = $(CR_3R_3')_nXR_2$
VIIIaP A = P
VIIIaH A = H

IIa A = $(CR_3R_3')_nXR_2$
IIaP A = P

IIb A = $(CR_3R_3')_nXR_2$
IIbP A = P

V

VI

VII wherein $R_2$, $R_3$, $R_{3'}$, $R_4$, $R_{4'}$, $R_5$, $R_{5'}$, n and X have the meanings as defined above for a compound of formula (I), $R_1$ is aryl or heteroaryl, p represents 0, 1 or 2, LG and Z independently represent a leaving group such as halogen, mesylate, tosylate or triflate, G represents chloro or bromo, M represents methyl or ethyl, V represents halogen and P represents a suitable protecting group (preferably Boc or benzyl).

Following Route A, a 4-step process is described for the synthesis of intermediate compounds of general formula IX wherein W is $CH_2$, $R_1$ is aryl or heteroaryl and $R_4$ and $R_{4'}$ are hydrogen (compounds of formula IXa):

Step1: A compound of formula XII is prepared by treating a compound of formula X with an amine of formula XI, in a suitable solvent such as toluene, optionally in the presence of a dehydrating agent such as molecular sieves.

Step2: The addition of allylmagnesium halide XIII to a compound of formula XII renders a compound of formula XIV. The reaction is carried out in a suitable aprotic solvent such as toluene or tetrahydrofuran.

Step3: A compound of formula XVI is prepared by treating a compound of formula XIV with an acryloyl derivative of formula XV. The reaction can be carried out under similar acylation conditions as described in Scheme 1.

Step4: Ring closing metathesis (RCM) of a compound of formula XVI using a Grubbs catalyst in a suitable solvent, such as dichloromethane, followed by hydrogenation, yields a compound of formula IXa.

Following Route B1, the synthesis of intermediate compounds of general formula II and VIII wherein W is O (compounds of formula IIa, IIb and VIIIa) is described in a general way. A compound of formula X is transformed into a compound of formula XVII by treatment with a source of cyanide and ammonia, such as sodium cyanide and ammonium bicarbonate, in a mixture of ethanol and water. The hydrolysis of a compound of formula XVII renders a compound of formula XVIII; the reaction can be carried out by treating with lithium hydroxide in water, at the reflux temperature. The reduction of a compound of formula XVIII under the conditions described in Scheme 2 yields a compound of formula XIX. Finally, the acylation reaction of a compound of formula XIX with a compound of formula XX under the reaction conditions described in Scheme 1, followed by internal cyclization by treatment with a suitable base, such as potassium tert-butoxide, in a suitable solvent, such as tetrahydrofuran, renders intermediate compounds of formula VIIIa.

Applying similar reduction conditions as those described in Scheme 3, intermediate compounds of formula IIb can be prepared from compounds of formula VIIIa.

Alternatively, compounds of formula IIa can be prepared from compounds of formula XIX by treatment with an alkylating agent of formula XXI, under alkylation conditions analogous as those described in Scheme 1.

Route B2 describes an alternative synthesis of intermediate compounds of general formula IX wherein W is O and $R_1$ is aryl or heteroaryl (compounds of formula IXb) to the synthesis described in Scheme 3 from a compound of formula VIII. A compound of formula X is transformed into a compound of formula XXII by reacting with an amine of formula XI, sodium hydroxide and chloroform under Bargellini reaction conditions. The reduction of a compound of formula XXII under the conditions described in Scheme 2 yields a compound of formula XXIII. Alternatively, the reduction can be carried out in a 2-step sequence, by converting the acid of formula XXII into its corresponding alkyl ester under standard esterification conditions followed by reduction with a suitable hydride, preferably Red-Al, in a suitable solvent, such as toluene or tetrahydrofuran. Finally, the alkylation of a compound of formula XXIII with a compound of formula XXIV, in the presence of a suitable base, preferably potassium tert-butoxide, in a suitable solvent, such as tetrahydrofuran, followed by internal cyclization, renders intermediate compounds of formula IXb.

Alternatively, compounds of formula XXII, XXIIP, XXIII and XXIIIP could be obtained from compounds of formula XVIII, XVIIIP, XIX and XIXP, respectively, under arylation conditions similar to the ones described in Scheme 1.

Alternatively, the group $(CR_3R_{3'})_nXR_2$ may be incorporated at different stages of the synthesis. Thus, a compound of formula VIIIa, IXa or IXb can be prepared from a protected precursor of formula VIIIaP, IXaP or IXbP, respectively, wherein P represents a suitable protecting group, by deprotection followed by reaction with a compound of formula V, VI or VII, under the reaction conditions described in Scheme 1.

The compounds of general formula XI, XIII, XV, XX, XXI and XXIV wherein $R_1$, $R_4$, $R_{4'}$, $R_5$, $R_{5'}$, LG, G, M and V have the meanings as defined above, are commercially available or can be prepared by conventional methods described in the bibliography.

Moreover, certain compounds of the present invention can also be obtained starting from other compounds of formula (I) by appropriate conversion reactions of functional groups, in one or several steps, using well-known reactions in organic chemistry under standard experimental conditions. As a way of example, some of these conversions include the demethylation of a methoxy group to yield an hydroxy group, the reduction of a nitro group to yield an amino group, the acylation of an amino group to yield an acylamino group and the reduction of a keto group to an hydroxy group.

EXAMPLES

The following abbreviations are used in the examples:

ACN: acetonitrile
Boc: tert-butoxycarbonyl
Conc: concentrated
DCM: dichloromethane
DMF: dimethylformamide
EX: example
h: hour/s
HPLC: high performance liquid chromatography
INT: intermediate
MeOH: methanol
MS: mass spectrometry
Min.: minutes
Quant: quantitative
Red-Al: sodium bis(2-methoxyethoxy)aluminumhydride
Ret.: retention
r.t.: room temperature
Sat: saturated
THF: tetrahydrofuran
Wt: weight Method A was used to determine the HPLC-MS spectrums:

Column: Xbridge $C_{18}$ XP 30×4.6 mm, 2.5 um
Temperature: 40° C.
Flow: 2.0 mL/min
Gradient: $NH_4HCO_3$ pH 8:ACN (95:5) - - - 0.5 min - - - (95:5) - - - 6.5 min - - - (0:100) - - - 1 min - - - (0:100)
Sample dissolved approx. 1 mg/mL in $NH_4HCO_3$ pH 8/ACN Alternatively, method B was used in some cases:

Column: Xbridge $C_{18}$ XP 30×4.6 mm, 2.5 um
Temperature: 25° C.
Flow: 2.0 mL/min
Gradient: $NH_4HCO_3$ pH 8:ACN (95:5) - - - 7 min - - - (0:100) - - - 3 min - - - (0:100)
Sample dissolved approx. 1 mg/mL in MeOH

SYNTHESIS OF INTERMEDIATES

Intermediate A: 9-benzyl-1-phenyl-1,9-diazaspiro[5.5]undecan-2-one

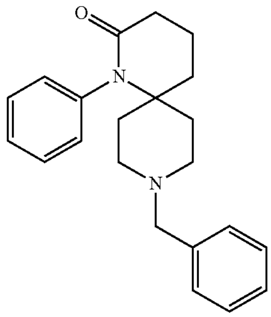 [SMILES: O=C1CCCC2(CCN(Cc3ccccc3)CC2)N1c1ccccc1]

Step 1: N-(1-benzylpiperidin-4-ylidene)aniline: A mixture of 1-benzyl-4-piperidone (0.5 g, 2.64 mmol), aniline (0.36 mL, 3.96 mmol) and molecular sieves (1 g, beads, 4A) in dry toluene (5 mL) was heated to reflux overnight. It was then filtered over a pad of celite and concentrated to dryness to yield the title compound (0.8 g, quant yield).

Step 2: 4-allyl-1-benzyl-N-phenylpiperidin-4-amine: To a solution of the product obtained in step 1 (0.37 g, 1.39 mmol) in dry toluene (5 mL), allylmagnesium bromide solution (1.67 mL, 1 M in diethyl ether, 1.67 mmol) was added dropwise at 0° C. under a nitrogen atmosphere. The mixture was stirred 30 min at 0° C. and then 1.5 h at r.t. Then, $NH_4Cl$ sat aqueous solution was added and it was extracted with ethyl acetate. The organic phases were combined, dried over $MgSO_4$, filtered and concentrated to dryness. The residue was purified by flash chromatography, silica gel, gradient DCM to MeOH:DCM (1:9) to give the title compound (0.64 g, 0.43 g theoretical weight; quant yield). HPLC retention time (method B): 5.58 min; MS: 307.2 (M+H).

Step 3: N-(4-allyl-1-benzylpiperidin-4-yl)-N-phenylacrylamide: To a solution of the product obtained in step 2 (0.091 g, 0.3 mmol) and triethylamine (0.33 mL, 2.38 mmol) in DCM (3 mL), acryloyl chloride (0.07 mL, 0.89 mmol) was added and the mixture was stirred at r.t. overnight. 10% $NaHCO_3$ aq sol and DCM were added and the phases were separated. The organic phase was dried over $MgSO_4$, filtered and concentrated to dryness. The residue was purified by flash chromatography, silica gel, gradient DCM to MeOH: DCM (1:20) to give the title compound (0.078 g, 73% yield). HPLC retention time (method B): 5.49 min; MS: 361.2 (M+H).

Step 4: 9-benzyl-1-phenyl-1,9-diazaspiro[5.5]undec-3-en-2-one: To a solution of the product obtained in step 3 (0.267 g, 0.74 mmol) in DCM (25 mL), benzylidene-bis (tricyclohexylphosphine)dichlororuthenium (Grubbs catalyst, 1st generation, 0.085 g, 0.10 mmol) was added, and the mixture was heated under reflux overnight. It was concentrated to dryness and the residue was purified by flash chromatography, silica gel, gradient ethyl acetate:cyclohexane (1:4) to ethyl acetate to give the title compound (0.145 g, 59% yield). HPLC retention time (method B): 4.17 min; MS: 333.1 (M+H).

Step 5: Title compound: A mixture of the product obtained in step 4 (0.080 g, 0.24 mmol) and platinum(IV) oxide (16 mg) in ethyl acetate (3 mL) was stirred at r.t. under a $H_2$ atmosphere (balloon) for 1.5 h. Then, the reaction mixture was filtered over a pad of celite and the solvent was removed under vacuum to give the title compound (0.066 g, 82% yield). HPLC retention time (method B): 4.15 min; MS: 335.2 (M+H).

This method was used for the preparation of intermediates B-D using suitable starting materials:

| INT | Structure | Chemical name | Ret time (min) | MS (M + H) |
|---|---|---|---|---|
| B | 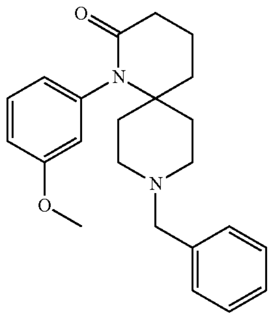 [SMILES: COc1cccc(N2C(=O)CCCC23CCN(Cc2ccccc2)CC3)c1] | 9-benzyl-1-(3-methoxyphenyl)-1,9-diazaspiro[5.5]undecan-2-one | 4.27 | 365.2 |
| C | 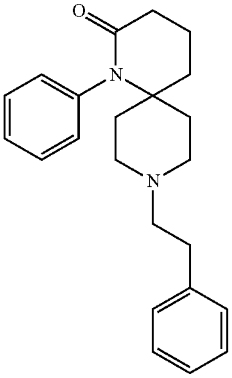 | 9-phenethyl-1-phenyl-1,9-diazaspiro[5.5]undecan-2-one | 4.10 | 349.2 |
| D | 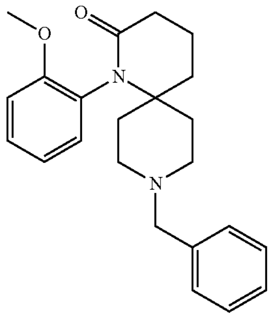 [SMILES: COc1ccccc1N1C(=O)CCCC12CCN(Cc1ccccc1)CC2] | 9-benzyl-1-(2-methoxyphenyl)-1,9-diazaspiro[5.5]undecan-2-one | 4.23 | 365.2 |

Intermediate E: 9-benzyl-1-(3-hydroxyphenyl)-1,9-diazaspiro[5.5]undecan-2-one

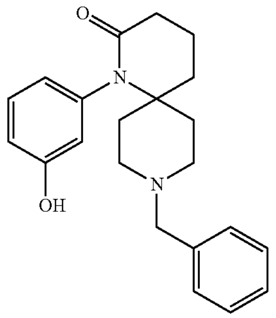 [SMILES: O=C1CCCC2(CCN(Cc3ccccc3)CC2)N1c1cccc(O)c1]

To a solution of intermediate B (0.200 g, 0.55 mmol) in DCM (8 mL), boron tribromide solution (4.3 mL, 1 M in DCM, 4.3 mmol) was added dropwise at −78° C. The reaction mixture was allowed to warm to −40° C. and it was stirred at −40° C. for 1 h and then 5 h at 0° C. Then, 8 M NaOH aqueous solution was added until pH 9 and it was extracted with DCM. The organic phases were combined, dried over $MgSO_4$, filtered and concentrated to dryness. The residue was purified by flash chromatography, silica gel, gradient DCM to MeOH:DCM (1:4) to give the title compound (0.109 g, 56% yield). HPLC retention time (method B): 3.64 min; MS: 351.2 (M+H).

Intermediate F: 9-benzyl-4-oxa-1,9-diazaspiro[5.5]undecan-2-one

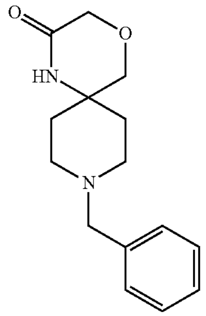 [SMILES: O=C1COCC2(CCN(Cc3ccccc3)CC2)N1]

Step 1: 8-benzyl-1,3,8-triazaspiro[4.5]decane-2,4-dione: 1-Benzyl-4-piperidone (10 g, 52.8 mmol) was added to a suspension of sodium cyanide (7 g, 143 mmol) and ammonium bicarbonate (40.2 g, 508 mmol) in a mixture of ethanol (70 mL) and water (70 mL). The resulting mixture was stirred at 60° C. for 36 h. The solids were collected by filtration, washed with warm water (2×20 mL) and dried under vacuum to yield 20.6 g of a crude product that was slurried in a mixture of ethanol (240 mL) and water (60 mL). The solids were collected by filtration and dried under vacuum to yield the title compound (16 g, 13.7 g theoretical weight; quant yield). HPLC retention time (method A): 2.46 min; MS: 260.1 (M+H).

Step 2: 4-amino-1-benzylpiperidine-4-carboxylic acid: Lithium hydroxide monohydrate (12.8 g, 306 mmol) was added to a suspension of the crude product obtained in step 1 (15.8 g, 61.2 mmol) in water (198 mL) and the mixture was refluxed overnight. The remaining solids were filtered off, washed with water and discarded. The filtrate was acidified to 5-6 with cHCl and concentrated to dryness. The residue was suspended in MeOH (50 mL) and the solids were collected by filtration, washed with MeOH (2×10 mL) and dried under vacuum to yield the title compound (12.1 g, 85% yield). HPLC retention time (method A): 0.95 min; MS: 235.1 (M+H).

Step 3: (4-amino-1-benzylpiperidin-4-yl)methanol: To a suspension of the crude product obtained in step 2 (12.0 g, 51.3 mmol) in dry THF (400 mL) cooled at 0-5° C., lithium aluminium hydride (7.79 g, 205 mmol) was added in portions. The reaction mixture was heated to reflux for 1.5 h. Water (24 mL), NaOH 1M aqueous solution (24 mL) and water (48 mL) were sequentially added the solids were filtered off over a pad of celite. The filtrate was concentrated to dryness to give the title compound as a crude product (7.2 g, 64% yield), that was used in the following step without further purification. HPLC retention time (method A): 1.89 min; MS: 221.1 (M+H).

Step 4: Title compound: To a solution of the crude product obtained in step 3 (3.23 g, 14.67 mmol) and triethylamine (2.0 mL, 14.67 mmol) in DCM (53 mL), chloroacetyl chloride (1.05 mL, 13.2 mmol) was added dropwise at r.t. The reaction mixture was stirred at r.t. for 2 h and then it was concentrated to dryness. The residue was dissolved in dry THF (50 mL), potassium tert-butoxide (4.78 g, 42.6 mmol) was added in portions under an argon atmosphere and the mixture was stirred at r.t. overnight. It was concentrated to dryness and the residue was purified by flash chromatography, silica gel, gradient DCM to MeOH:DCM (1:4) to give the title compound (2.29 g, 60% yield). HPLC retention time (method A): 2.73 min; MS: 261.1 (M+H).

Intermediate G: 9-phenethyl-4-oxa-1,9-diazaspiro[5.5]undecan-2-one

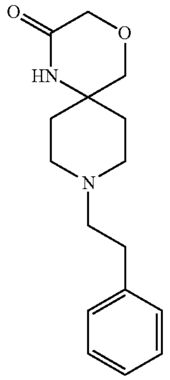 [SMILES: O=C1COCC2(CCN(CCc3ccccc3)CC2)N1]

Step 1: 4-oxa-1,9-diazaspiro[5.5]undecan-2-one acetate: A mixture of intermediate F (1.0 g, 3.84 mmol), AcOH (0.44 mL, 7.68 mmol) and Pd (100 mg, 5% wt on charcoal, wet) in MeOH (32 mL) was stirred at 50° C. under 3 bars of $H_2$ overnight. Then, the solids were filtered off and the solvent was removed under vacuum to give the title compound as a crude product (0.9 g, quant yield), that was used in the following step without further purification. HPLC retention time (method A): 0.23 min; MS: 171.1 (M+H).

Step 2: Title compound: To a solution of the crude product obtained in step 1 (0.9 g, 3.8 mmol) and phenylacetaldehyde (1.36 mL, 11.61 mmol) in dry THF (44 mL), AcOH (0.82 mL, 14.3 mmol) was added. The reaction mixture was stirred at r.t. for 15 min. and sodium triacetoxyborohydride (3.42 g, 16.1 mmol) was added in portions. The resulting mixture was stirred at r.t. overnight, after which conc. $NH_3$ (25 mL) was added and the mixture stirred at r.t. for 1 h. It was then extracted with ethyl, the organic phases were combined, dried over $MgSO_4$, filtered and concentrated to dryness. The residue was purified by flash chromatography, silica gel, gradient DCM to MeOH:DCM (1:4) to give the title compound (799 mg, 77% yield). HPLC retention time (method A): 2.88 min; MS: 275.1 (M+H).

Intermediate H: 1-benzyl-9-phenethyl-4-oxa-1,9-diazaspiro[5.5]undecan-2-one

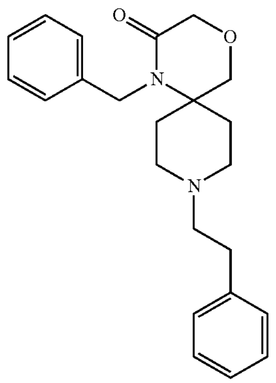 [SMILES: O=C1COCC2(CCN(CCc3ccccc3)CC2)N1Cc1ccccc1]

To a solution of intermediate G (201 mg, 0.73 mmol) in dry DMF (2 mL) cooled at 0° C., NaH (88 mg, 60 wt % in mineral oil, 2.2 mmol) was added. The reaction mixture was stirred at r.t. for 30 min. and it was cooled again at 0° C. Benzyl bromide (0.096 mL, 0.80 mmol) was added and the resulting mixture was stirred at r.t. overnight. Water was added and it was extracted with DCM. The organic phases were combined, dried over $MgSO_4$, filtered and concentrated to dryness. The residue was purified by flash chromatography, silica gel, gradient DCM to MeOH:DCM (1:9) to give the title compound (105 mg, 39% yield). HPLC retention time (method A): 4.15 min; MS: 365.1 (M+H).

Intermediate I: 9-phenethyl-1-phenyl-4-oxa-1,9-diazaspiro[5.5]undecan-2-one

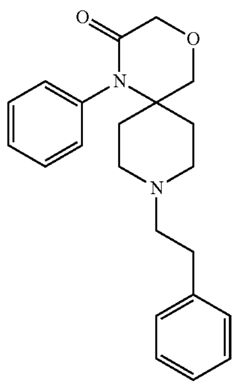 [SMILES: O=C1COCC2(CCN(CCc3ccccc3)CC2)N1c1ccccc1]

A mixture of intermediate G (250 mg, 0.91 mmol), $K_2OC_3$ (126 mg, 0.91 mmol), CuI (69 mg, 0.36 mmol) and iodobenzene (0.2 mL, 1.82 mmol) in dry DMF (2 mL) was heated, under an argon atmosphere, at 180° C. under microwave irradiation for 90 min. The reaction mixture was cooled, additional reagents were loaded and it was heated again at 180° C. under microwave irradiation for 90 min. This cycle was repeated 4 times. The reaction mixture was diluted with ethyl acetate, filtered over a pad of celite and concentrated under vacuum. The residue was purified by flash chromatography, $C_{18}$, gradient aqueous $NH_4HCO_3$ pH 8 to acetonitrile, to give the title compound (50 mg, 16% yield). HPLC retention time (method A): 3.85 min; MS: 351.1 (M+H).

Intermediate J: 9-benzyl-1-phenyl-4-oxa-1,9-diazaspiro[5.5]undecan-2-one

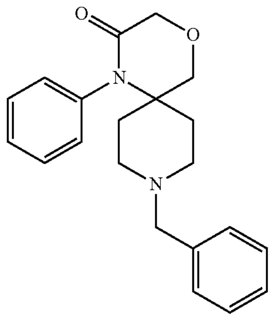 [SMILES: O=C1COCC2(CCN(Cc3ccccc3)CC2)N1c1ccccc1]

Intermediate J was prepared according to the procedure described for intermediate I using intermediate F as starting material.

HPLC retention time (method A): 3.85 min; MS: 337.2 (M+H).

Intermediate K: 9-benzyl-4-oxa-1,9-diazaspiro[5.5]undecane

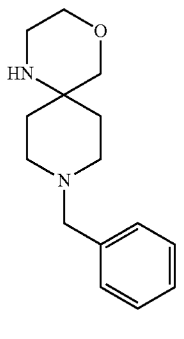 [SMILES: c1ccc(CN2CCC3(CC2)COCCN3)cc1]

To a solution of intermediate F (0.295 g, 1.13 mmol) in dry THF (9 mL) cooled at 0° C., lithium aluminium hydride solution (6 mL, 1M in THF, 6 mmol) was added dropwise. The reaction mixture was heated to reflux for 3 h. Water (0.2 mL), NaOH 1M aqueous solution (0.2 mL) and water (0.4 mL) were sequentially added the solids were filtered off over a pad of celite and the filter was rinsed with DCM. The filtrate was dried over $MgSO_4$ and concentrated to dryness and the residue was purified by flash chromatography, silica gel, gradient DCM to MeOH:DCM (1:4) to give the title compound (0.198 g, 71% yield). HPLC retention time (method A): 2.48 min; MS: 247.1 (M+H).

Intermediate L: 9-phenethyl-4-oxa-1,9-diazaspiro [5.5]undecane

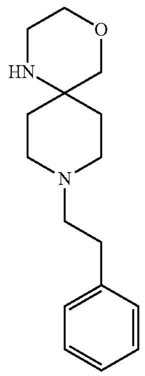

Intermediate L was prepared according to the procedure described for intermediate K using intermediate G as starting material.

HPLC retention time (method A): 2.73 min; MS: 261.1 (M+H).

Intermediate M: tert-butyl 2-oxo-4-oxa-1,9-diazaspiro[5.5]undecane-9-carboxylate

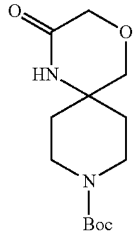

A solution of the crude product obtained in intermediate G step 1 (1.68 g, 7.3 mmol) and di-tert-butyl dicarbonate (3.85 g, 17.6 mmol) in a mixture of 1,4-dioxane (2 mL) and 1M NaOH aqueous solution (3.8 mL) was stirred at r.t. overnight. Water was added and it was extracted with ethyl acetate. The organic phases were combined, dried over $MgSO_4$, filtered and concentrated to dryness. The residue was purified by flash chromatography, silica gel, gradient DCM to MeOH:DCM (1:4) to give the title compound (1.26 g, 64% yield). HPLC retention time (method A): 2.84 min; MS: 215.1 (M+H−56).

Intermediate N: tert-butyl 2-oxo-1-phenyl-4-oxa-1,9-diazaspiro[5.5]undecane-9-carboxylate

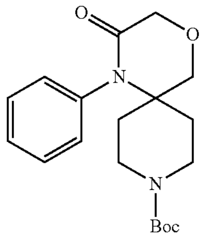 [SMILES: CC(C)(C)OC(=O)N1CCC2(CC1)COCC(=O)N2c1ccccc1]

Step 1: 1-(tert-butoxycarbonyl)-4-(phenylamino)piperidine-4-carboxylic acid: To a solution of aniline (0.70 g, 7.53 mmol) in THF (22 mL) cooled at 0° C., sodium hydroxide (3.0 g, 75.3 mmol, previously grinded) and tert-butyl 4-oxopiperidine-1-carboxylate (6.0 g, 30.1 mmol) were added. Then, chloroform (6.1 mL, 75.3 mmol) was added dropwise at 0° C. and the mixture was stirred at this temperature for 1 h and then at r.t. overnight. The precipitated solids were collected by filtration, washed with THF and then dissolved in water. The aqueous phase was washed 3 times with diethyl ether, which was discarded. The pH of the aqueous phase was then adjusted to 4 with 1M HCl and it was extracted with chloroform. The organic phases were combined, dried over $MgSO_4$, filtered and concentrated to dryness to give the title compound (2.14 g, 88% yield based on starting aniline). HPLC retention time (method A): 2.80 min; MS: 265.1 (M+H−56).

Step 2: 1-tert-butyl 4-ethyl 4-(phenylamino)piperidine-1,4-dicarboxylate: To a mixture of the crude product obtained in step 1 (2.14 g, 6.68 mmol) and sodium bicarbonate (4.21 g, 50.1 mmol) in DMF (10 mL), iodoethane (3.8 mL, 47.1 mmol) was added and the mixture stirred at r.t. overnight. The solids were filtered off and the filtrate was diluted with ethyl acetate. The organic phase was sequentially washed with 1M HCl, water and brine, and it was then dried over $MgSO_4$, filtered and concentrated to dryness to give the title compound (2.11 g, 90% yield)

Step 3: tert-butyl 4-(hydroxymethyl)-4-(phenylamino)piperidine-1-carboxylate: To a solution of the crude product obtained in step 2 (1.97 g, 5.65 mmol) in dry toluene (25 mL) cooled at 10° C., Red-Al solution (5.1 mL, 3.3 M in toluene, 16.9 mmol) was added dropwise. The reaction mixture was stirred at 10-15° C. for 3.5 h. It was then cooled at 0-5° C. and NaOH 1M aqueous solution was carefully added. The mixture was extracted with DCM and the organic phases were combined, dried over $MgSO_4$, filtered and concentrated to dryness. The residue was purified by flash chromatography, silica gel, gradient cyclohexane to ethyl acetate:cyclohexane (3:1) to give the title compound (1.26 g, 73% yield). HPLC retention time (method A): 4.02 min; MS: 307.2 (M+H).

Step 4: Title compound: To a solution of the product obtained in step 3 (1.25 g, 4.07 mmol) in THF (16 mL), under nitrogen, potassium tert-butoxide (8.2 mL, 1M solution in THF, 8.2 mmol) was added and the reaction mixture was stirred at r.t. for 30 min. Ethyl bromoacetate (0.68 mL, 6.1 mmol) was then added, and the mixture was stirred at r.t. overnight. Additional amounts of potassium tert-butoxide and ethyl bromoacetate were added and the mixture was stirred again at r.t. overnight to get the reaction to completion. It was then diluted with water and ethyl acetate, the phases were separated and the aqueous phase was extracted with ethyl acetate. The organic phases were combined, dried over $MgSO_4$, filtered and concentrated under vacuum. The residue was purified by flash chromatography, silica gel, gradient cyclohexane to ethyl acetate:cyclohexane (20:1) to give the title compound (430 mg, 30% yield). HPLC retention time: 3.67 min; MS: 347.2 (M+H).

Intermediate O: tert-butyl 1-phenyl-4-oxa-1,9-diazaspiro[5.5]undecane-9-carboxylate

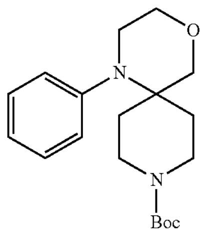 [SMILES: CC(C)(C)OC(=O)N1CCC2(CC1)COCCN2c1ccccc1]

To a solution of intermediate N (0.43 g, 1.24 mmol) in THF (8 mL), borane-dimethyl sulfide complex (0.38 mL, 3.72 mmol) was added dropwise at r.t. The reaction mixture was stirred at 55° C. for 2 h, then it was cooled to r.t. MeOH was carefully added and the solvent was concentrated under vacuum. The residue was dissolved in MeOH (6 mL), N,N'-dimethylethylenediamine (0.66 mL, 6.1 mmol) was added and the mixture was stirred under reflux for 5 h. After cooling to r.t., the volatiles were removed under vacuum, and the residue was purified by flash chromatography, silica gel, gradient cyclohexane to ethyl acetate:cyclohexane (1:1) to give the title compound (0.211 g, 51% yield). HPLC retention time (method A): 4.66 min; MS: 333.2 (M+H).

Intermediate P: tert-butyl 4-oxa-1,9-diazaspiro[5.5]undecane-9-carboxylate

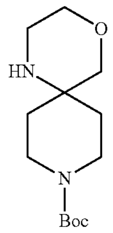

Intermediate P was prepared according to the procedure described for intermediate O using intermediate M as starting material.

HPLC retention time (method A): 2.81 min; MS: 257.1 (M+H).

Intermediate Q: tert-butyl 1-benzyl-4-oxa-1,9-diazaspiro[5.5]undecane-9-carboxylate

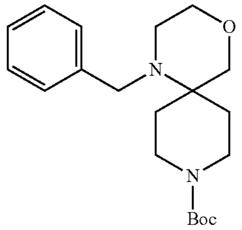 [SMILES: CC(C)(C)OC(=O)N1CCC2(CC1)COCCN2Cc1ccccc1]

To a solution of intermediate P (0.122 g, 0.47 mmol) and benzaldehyde (0.062 mL, 0.62 mmol) in dry THF (3.2 mL), acetic acid (0.06 mL, 1.06 mmol) was added. The reaction mixture was stirred at r.t. for 15 min. and sodium triacetoxyborohydride (0.303 g, 1.44 mmol) was added in portions. The resulting mixture was stirred at r.t. overnight. Water was added, pH was adjusted to 9 with $NH_3$ conc and it was extracted with ethyl acetate. The organic phases were combined, dried over $MgSO_4$, filtered and concentrated to dryness. The residue was purified by flash chromatography, silica gel, gradient DCM to MeOH:DCM (1:4) to give the title compound (138 mg, 83% yield). HPLC retention time (method A): 5.12 min; MS: 347.2 (M+H).

Synthesis of Examples

Example 1: 9-benzyl-1-phenyl-1,9-diazaspiro[5.5]undecane

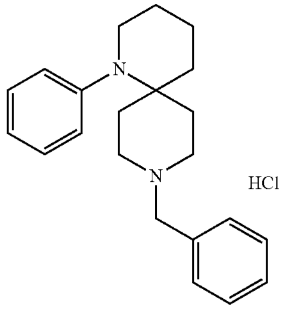 [SMILES: c1ccc(CN2CCC3(CCCCN3c3ccccc3)CC2)cc1 ; Cl]

To a solution of intermediate A (0.062 g, 0.18 mmol) in THF (2 mL) cooled at 0° C., lithium aluminium hydride solution (0.2 mL, 1M in THF, 0.2 mmol) was added dropwise and the reaction mixture was stirred at r.t. for 3 h. $NaHCO_3$ sat. aqueous solution was added, and the solids were filtered off over a pad of celite, rinsing them with THF. The filtrate was dried over $MgSO_4$, filtered and concentrated to dryness and the residue was purified by flash chromatography, silica gel, gradient cyclohexane to ethyl acetate:cyclohexane (1:1) to give the title compound (0.024 g, 44% yield). HPLC retention time (method B): 6.34 min; MS: 321.2 (M+H).

This method was used for the preparation of examples 2-7 using suitable starting materials:
| EX | Structure | Chemical name | Ret time (min) | MS (M + H) |
|---|---|---|---|---|
| 2 | 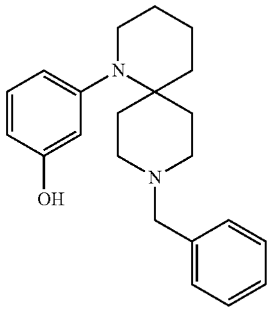 [SMILES: Oc1cccc(N2CCCCC23CCN(Cc2ccccc2)CC3)c1] | 3-(9-benzyl-1,9-diazaspiro[5.5]undecan-1-yl)phenol | 4.88 (method B) | 337.2 |
| 3 | 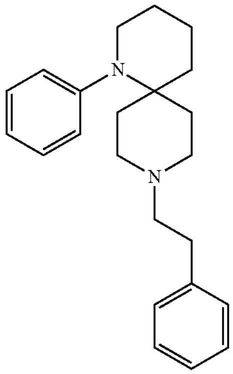 [SMILES: c1ccc(CCN2CCC3(CCCCN3c3ccccc3)CC2)cc1] | 9-phenethyl-1-phenyl-1,9-diazaspiro[5.5]undecane | 5.39 | 335.2 |
| 4 | 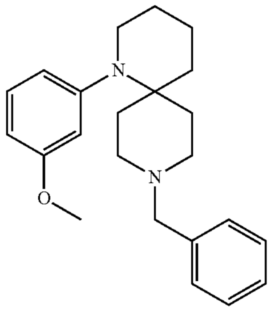 [SMILES: COc1cccc(N2CCCCC23CCN(Cc2ccccc2)CC3)c1] | 9-benzyl-1-(3-methoxyphenyl)-1,9-diazaspiro[5.5]undecane | 5.61 | 351.2 |
| 5 | 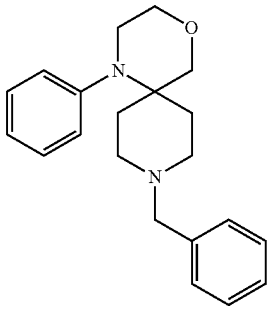 [SMILES: c1ccc(CN2CCC3(CC2)COCCN3c2ccccc2)cc1] | 9-benzyl-1-phenyl-4-oxa-1,9-diazaspiro[5.5]undecane | 4.77 | 323.1 |

-continued

| EX | Structure | Chemical name | Ret time (min) | MS (M + H) |
|---|---|---|---|---|
| 6 | 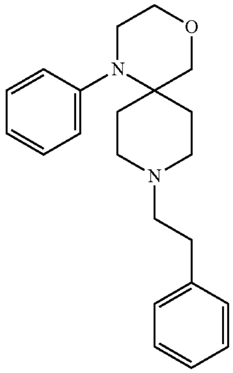 [SMILES: c1ccc(CCN2CCC3(CC2)COCCN3c2ccccc2)cc1] | 1-benzyl-9-phenethyl-4-oxa-1,9-diazaspiro[5.5]undecane | 4.91 | 351.2 |
| 7 | 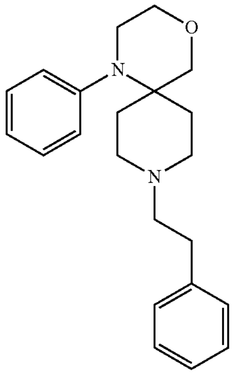 [SMILES: c1ccc(CCN2CCC3(CC2)COCCN3c2ccccc2)cc1] | 9-phenethyl-1-phenyl-4-oxa-1,9-diazaspiro[5.5]undecane (*) (**) | 4.64 | 337.2 |

(*) Additional treatment with Pd/C under hydrogenation conditions was performed to get the reaction to completion.
(**) Example 7 was alternatively synthesized from intermediate O using the method described for example 34.

Example 8: cyclopropyl(9-phenethyl-4-oxa-1,9-diazaspiro[5.5]undecan-1-yl)methanone

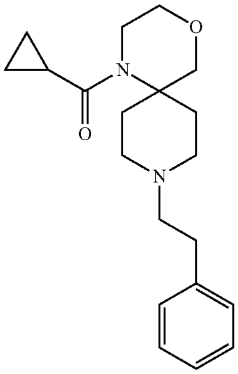 [SMILES: O=C(C1CC1)N1CCOCC12CCN(CCc1ccccc1)CC2]

To a solution of intermediate L (0.15 g, 0.58 mmol) and triethylamine (0.12 mL, 0.86 mmol) in dichloromethane (1.5 mL) at 0° C., a solution of cyclopropanecarbonyl chloride (0.06 mL, 0.69 mmol) in dichloromethane (0.5 mL) was added dropwise. The reaction mixture was stirred at r.t. overnight, then $NaHCO_3$ sat solution was added and it was extracted with dichloromethane. The organic phases were combined, dried over $MgSO_4$, filtered and concentrated to dryness. The residue was purified by flash chromatography, silica gel, gradient DCM to MeOH:DCM (1:4) to give the title compound (94 mg, 50% yield).

HPLC retention time (method A): 3.55 min; MS: 329.2 (M+H).

This method was used for the preparation of examples 9-23 using suitable starting materials:
| EX | Structure | Chemical name | Ret time (min) | MS (M + H) |
|---|---|---|---|---|
| 9 | 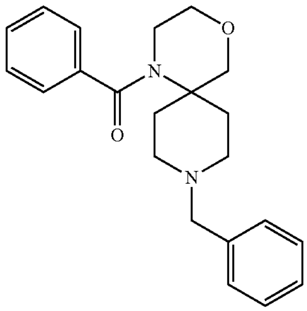 [SMILES: O=C(c1ccccc1)N1CCOCC12CCN(Cc1ccccc1)CC2] | (9-benzyl-4-oxa-1,9-diazaspiro[5.5]undecan-1-yl)(phenyl)methanone | 4.02 | 351.2 |
| 10 | 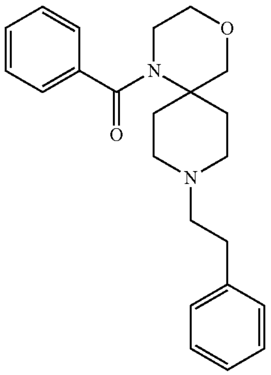 [SMILES: O=C(c1ccccc1)N1CCOCC12CCN(CCc1ccccc1)CC2] | (9-phenethyl-4-oxa-1,9-diazaspiro[5.5]undecan-1-yl)(phenyl)methanone | 4.07 | 365.2 |
| 11 | 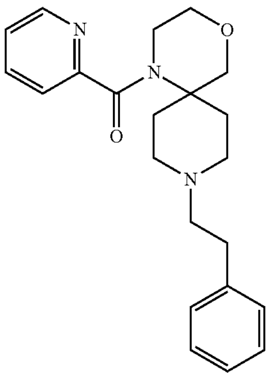 [SMILES: O=C(c1ccccn1)N1CCOCC12CCN(CCc1ccccc1)CC2] | (9-phenethyl-4-oxa-1,9-diazaspiro[5.5]undecan-1-yl)(pyridin-2-yl)methanone | 3.33 | 366.2 |
| 12 | 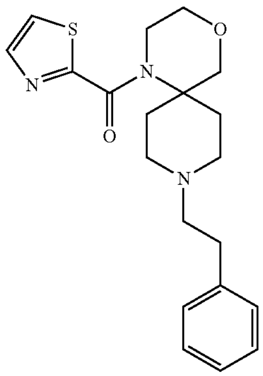 [SMILES: O=C(c1nccs1)N1CCOCC12CCN(CCc1ccccc1)CC2] | (9-phenethyl-4-oxa-1,9-diazaspiro[5.5]undecan-1-yl)(thiazol-2-yl)methanone | 3.73 | 372.1 |

-continued
| EX | Structure | Chemical name | Ret time (min) | MS (M + H) |
| --- | --- | --- | --- | --- |
| 13 | 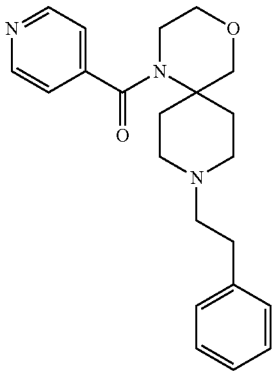 [SMILES: O=C(c1ccncc1)N1CCOCC12CCN(CCc1ccccc1)CC2] | (9-phenethyl-4-oxa-1,9-diazaspiro[5.5]undecan-1-yl)(pyridin-4-yl)methanone | 3.28 | 366.2 |
| 14 | 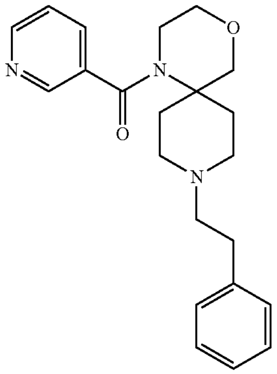 [SMILES: O=C(c1cccnc1)N1CCOCC12CCN(CCc1ccccc1)CC2] | (9-phenethyl-4-oxa-1,9-diazaspiro[5.5]undecan-1-yl)(pyridin-3-yl)methanone | 3.26 | 366.2 |
| 15 | 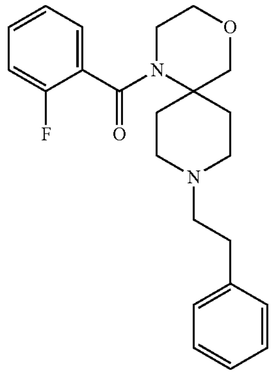 [SMILES: O=C(c1ccccc1F)N1CCOCC12CCN(CCc1ccccc1)CC2] | (2-fluorophenyl)(9-phenethyl-4-oxa-1,9-diazaspiro[5.5]undecan-1-yl)methanone | 4.07 | 383.2 |
| 16 | 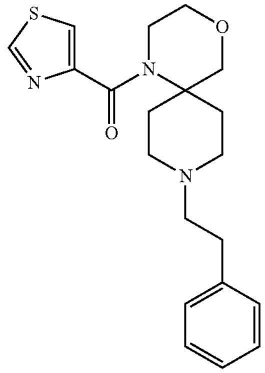 [SMILES: O=C(c1cscn1)N1CCOCC12CCN(CCc1ccccc1)CC2] | (9-phenethyl-4-oxa-1,9-diazaspiro[5.5]undecan-1-yl)(thiazol-4-yl)methanone | 3.22 | 372.1 |

-continued
| EX | Structure | Chemical name | Ret time (min) | MS (M + H) |
|---|---|---|---|---|
| 17 | 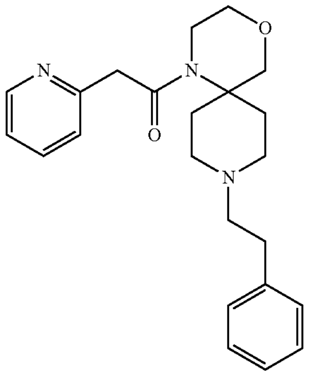 [SMILES: O=C(Cc1ccccn1)N1CCOCC12CCN(CCc1ccccc1)CC2] | 1-(9-phenethyl-4-oxa-1,9-diazaspiro[5.5]undecan-1-yl)-2-(pyridin-2-yl)ethanone | 3.3 | 380.2 |
| 18 | 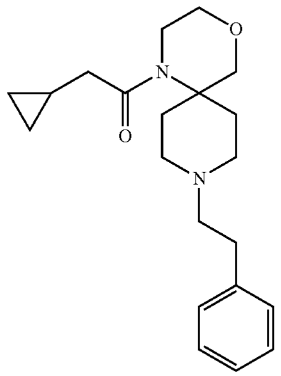 [SMILES: O=C(CC1CC1)N1CCOCC12CCN(CCc1ccccc1)CC2] | 2-cyclopropyl-1-(9-phenethyl-4-oxa-1,9-diazaspiro[5.5]undecan-1-yl)ethanone | 3.7 | 343.2 |
| 19 | 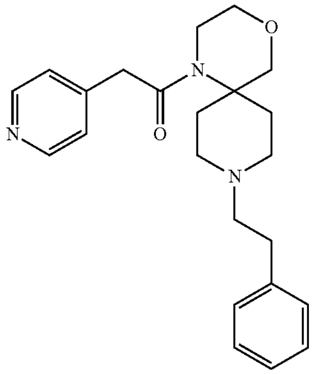 [SMILES: O=C(Cc1ccncc1)N1CCOCC12CCN(CCc1ccccc1)CC2] | 1-(9-phenethyl-4-oxa-1,9-diazaspiro[5.5]undecan-1-yl)-2-(pyridin-4-yl)ethanone | 3.25 | 380.2 |
| 20 | 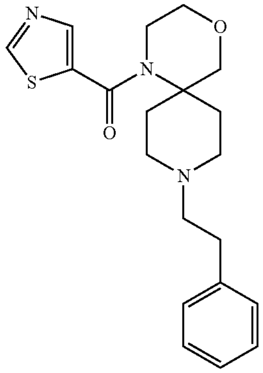 [SMILES: O=C(c1cncs1)N1CCOCC12CCN(CCc1ccccc1)CC2] | (9-phenethyl-4-oxa-1,9-diazaspiro[5.5]undecan-1-yl)(thiazol-5-yl)methanone | 3.4 | 372.1 |

-continued
| EX | Structure | Chemical name | Ret time (min) | MS (M + H) |
|---|---|---|---|---|
| 21 | 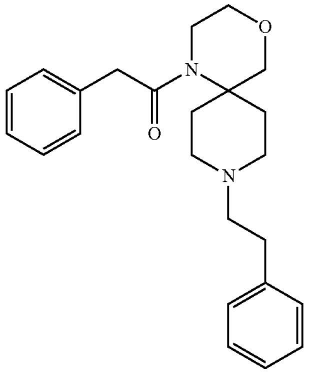 [SMILES: O=C(Cc1ccccc1)N1CCOCC12CCN(CCc1ccccc1)CC2] | 1-(9-phenethyl-4-oxa-1,9-diazaspiro[5.5]undecan-1-yl)-2-phenylethanone | 4.1 | 379.2 |
| 22 | 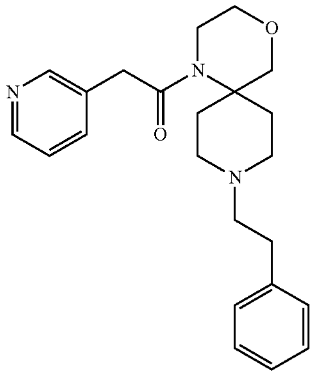 [SMILES: O=C(Cc1cccnc1)N1CCOCC12CCN(CCc1ccccc1)CC2] | 1-(9-phenethyl-4-oxa-1,9-diazaspiro[5.5]undecan-1-yl)-2-(pyridin-3-yl)ethanone | 3.27 | 380.2 |
| 23* | 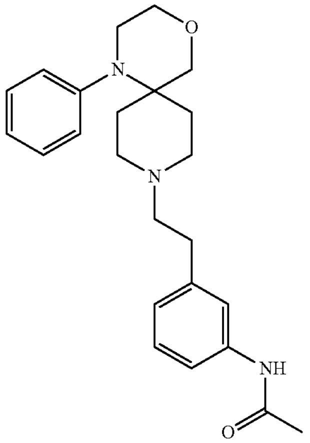 [SMILES: CC(=O)Nc1cccc(CCN2CCC3(CC2)COCCN3c2ccccc2)c1] | N-(3-(2-(1-phenyl-4-oxa-1,9-diazaspiro[5.5]undecan-9-yl)ethyl)phenyl)acetamide | 3.72 | 394.2 |
*compound 23 has been prepared by reacting compound 50 with acetylchloride and following the method as described in example 8.

Example 24: 9-phenethyl-1-(pyridin-4-ylmethyl)-4-oxa-1,9-diazaspiro[5.5]undecane

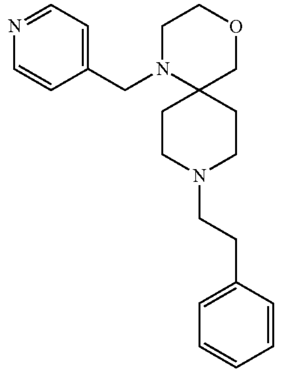 [SMILES: c1ccc(CCN2CCC3(CC2)COCCN3Cc2ccncc2)cc1]

To a solution of intermediate L (0.1 g, 0.38 mmol) and 4-pyridinecarboxaldehyde (0.072 mL, 0.77 mmol) in dry THF (3.7 mL), acetic acid (0.048 mL, 0.84 mmol) was added. The reaction mixture was stirred for 15 min., sodium triacetoxyborohydride (0.163 g, 0.77 mmol) was added in portions and the resulting mixture was stirred at r.t. overnight. Water was added, the pH was adjusted to 9 with 1 N NaOH and it was extracted with DCM. The organic phases were combined, dried over $MgSO_4$, filtered and concentrated to dryness. The residue was purified by flash chromatography, silica gel, gradient DCM to MeOH:DCM (1:4) to give the title compound (57 mg, 42% yield).

HPLC retention time (method A): 3.84 min; MS: 352.2 (M+H).

This method was used for the preparation of examples 25-33 using suitable starting materials:

| EX | Structure | Chemical name | Ret time (min) | MS (M + H) |
|---|---|---|---|---|
| 25 | 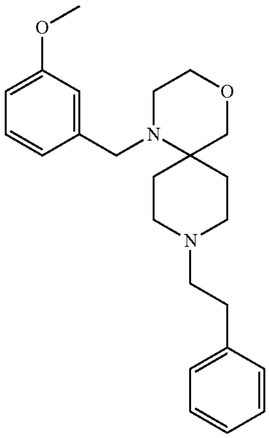 [SMILES: COc1cccc(CN2CCOCC23CCN(CCc2ccccc2)CC3)c1] | 1-(3-methoxybenzyl)-9-phenethyl-4-oxa-1,9-diazaspiro[5.5]undecane | 4.93 | 381.2 |
| 26 | 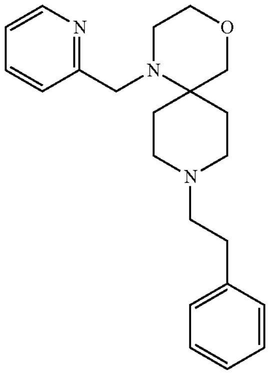 [SMILES: c1ccc(CCN2CCC3(CC2)COCCN3Cc2ccccn2)cc1] | 9-phenethyl-1-(pyridin-2-ylmethyl)-4-oxa-1,9-diazaspiro[5.5]undecane | 3.84 | 352.2 |

-continued
| EX | Structure | Chemical name | Ret time (min) | MS (M + H) |
|---|---|---|---|---|
| 27 | 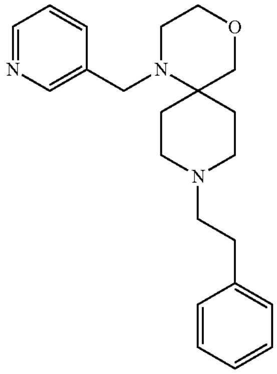 [SMILES: c1ccc(CCN2CCC3(CC2)COCCN3Cc2cccnc2)cc1] | 9-phenethyl-1-(pyridin-3-ylmethyl)-4-oxa-1,9-diazaspiro[5.5]undecane | 3.73 | 352.2 |
| 28 | 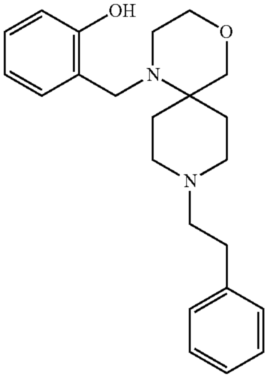 [SMILES: Oc1ccccc1CN1CCOCC12CCN(CCc1ccccc1)CC2] | 2-((9-phenethyl-4-oxa-1,9-diazaspiro[5.5]undecan-1-yl)methyl)phenol | 4.64 | 367.2 |
| 29 | 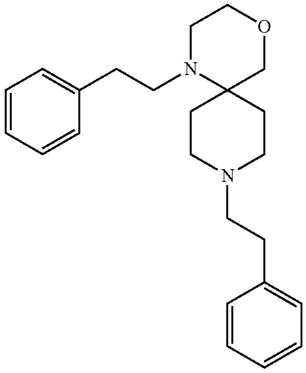 [SMILES: c1ccc(CCN2CCC3(CC2)COCCN3CCc2ccccc2)cc1] | 1,9-diphenethyl-4-oxa-1,9-diazaspiro[5.5]undecane | 4.81 | 365.2 |
| 30 | 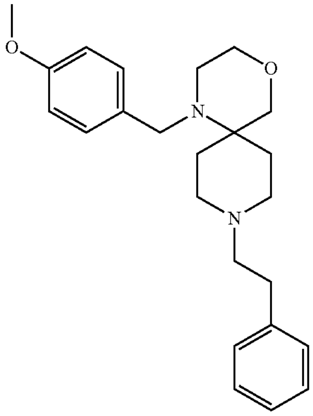 [SMILES: COc1ccc(CN2CCOCC23CCN(CCc2ccccc2)CC3)cc1] | 1-(4-methoxybenzyl)-9-phenethyl-4-oxa-1,9-diazaspiro[5.5]undecane | 4.79 | 381.2 |

-continued
| EX | Structure | Chemical name | Ret time (min) | MS (M + H) |
|---|---|---|---|---|
| 31 | 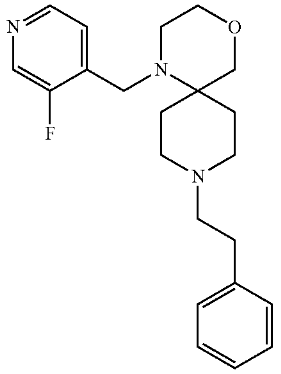 [SMILES: Fc1cnccc1CN1CCOCC12CCN(CCc1ccccc1)CC2] | 1-((3-fluoropyridin-4-yl)methyl)-9-phenethyl-4-oxa-1,9-diazaspiro[5.5]undecane | 4.04 | 370.2 |
| 32 | 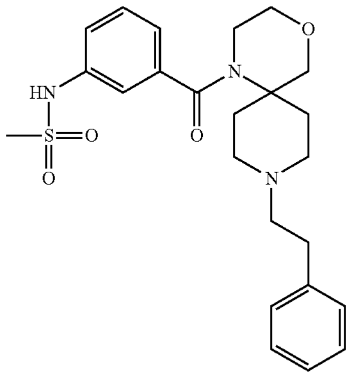 [SMILES: CS(=O)(=O)Nc1cccc(C(=O)N2CCOCC23CCN(CCc2ccccc2)CC3)c1] | N-(3-((9-phenethyl-4-oxa-1,9-diazaspiro[5.5]undecan-1-yl)methyl)phenyl) methanesulfonamide | 4.07 | 444.2 |
| 33 | 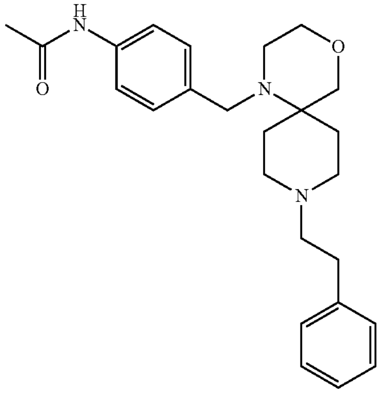 [SMILES: CC(=O)Nc1ccc(CN2CCOCC23CCN(CCc2ccccc2)CC3)cc1] | N-(4-((9-phenethyl-4-oxa-1,9-diazaspiro[5.5]undecan-1-yl)methyl)phenyl)acetamide | 3.82 | 408.2 |

Example 34: 1-benzyl-9-(2-(pyridin-2-yl)ethyl)-4-oxa-1,9-diazaspiro[5.5]undecane

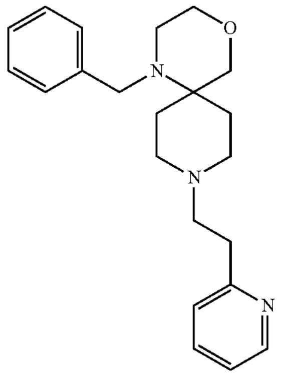 [SMILES: c1ccc(CN2CCOCC23CCN(CCc2ccccn2)CC3)cc1]

Step 1: 1-benzyl-4-oxa-1,9-diazaspiro[5.5]undecane trifluoroacetate. To a solution of intermediate Q (0.138 g, 0.4 mmol) in DCM (1.4 mL), trifluoroacetic acid (0.26 mL, 3.43 mmol) was added, and the reaction mixture was heated at 40° C. for 2 h. The solvent was evaporated to dryness to give the title compound as a crude product (0.3 g, 48 wt %, quant yield), that was used in the following step without further purification. HPLC retention time: 2.61 min; MS: 247.1 (M+H).

Step 2: Title compound: A mixture of the crude product obtained in step 1 (0.3 g, 48 wt %, 0.4 mmol). 2-(2-bromoethyl)pyridine hydrobromide (0.106 g, 0.4 mmol), sodium iodide (0.036 g, 0.24 mmol) and $K_2OC_3$ (0.33 g, 2.39 mmol) in ACN (4.5 mL) was stirred in a sealed tube at 80° C. overnight. Water was added and the reaction mixture was extracted with ethyl acetate. The organic phases were combined, washed with brine, dried over $MgSO_4$, filtered and concentrated to dryness. The residue was purified by flash chromatography, silica gel, gradient DCM to MeOH: DCM (1:4) to give the title compound (72 mg, 51% yield).

HPLC retention time: 3.75 min; MS: 352.2 (M+H).

This method was used for the preparation of examples 35-45 using suitable starting materials:

| EX | Structure | Chemical name | Ret time (min) (method A) | MS (M + H) |
|---|---|---|---|---|
| 35 | 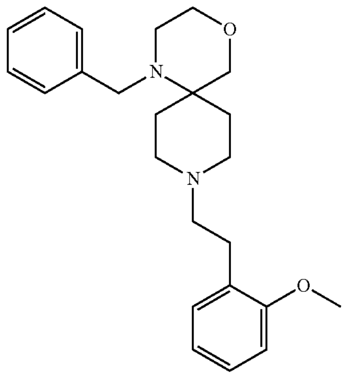 [SMILES: COc1ccccc1CCN1CCC2(CC1)COCCN2Cc1ccccc1] | 1-benzyl-9-(2-methoxyphenethyl)-4-oxa-1,9-diazaspiro[5.5]undecane | 4.9 | 381.2 |
| 36 | 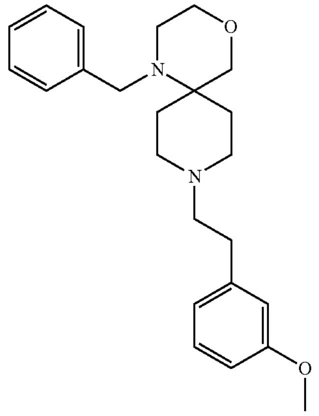 [SMILES: COc1cccc(CCN2CCC3(CC2)COCCN3Cc2ccccc2)c1] | 1-benzyl-9-(3-methoxyphenethyl)-4-oxa-1,9-diazaspiro[5.5]undecane | 4.88 | 381.2 |

-continued
| EX | Structure | Chemical name | Ret time (min) (method A) | MS (M + H) |
|---|---|---|---|---|
| 37 | 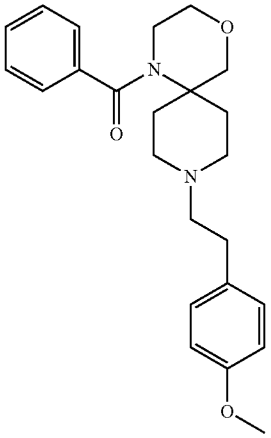 [SMILES: COc1ccc(CCN2CCC3(CC2)COCCN3C(=O)c2ccccc2)cc1] | 1-benzyl-9-(4-methoxyphenethyl)-4-oxa-1,9-diazaspiro[5.5]undecane | 4.79 | 381.2 |
| 38 | 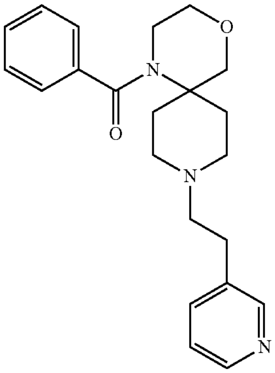 [SMILES: O=C(c1ccccc1)N1CCOCC12CCN(CCc1cccnc1)CC2] | 1-benzyl-9-(2-(pyridin-3-yl)ethyl)-4-oxa-1,9-diazaspiro[5.5]undecane | 3.81 | 352.2 |
| 39 | 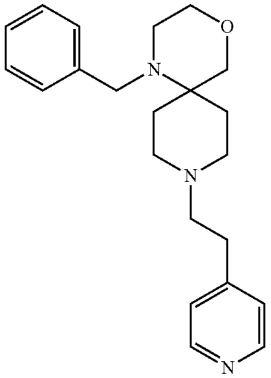 [SMILES: c1ccc(CN2CCOCC23CCN(CCc2ccncc2)CC3)cc1] | 1-benzyl-9-(2-(pyridin-4-yl)ethyl)-4-oxa-1,9-diazaspiro[5.5]undecane | 3.83 | 352.2 |
| 40 | 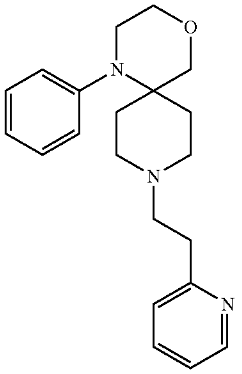 [SMILES: c1ccc(N2CCOCC23CCN(CCc2ccccn2)CC3)cc1] | 1-phenyl-9-(2-(pyridin-2-yl)ethyl)-4-oxa-1,9-diazaspiro[5.5]undecane | 3.5 | 338.2 |

-continued
| EX | Structure | Chemical name | Ret time (min) (method A) | MS (M + H) |
|---|---|---|---|---|
| 41 | 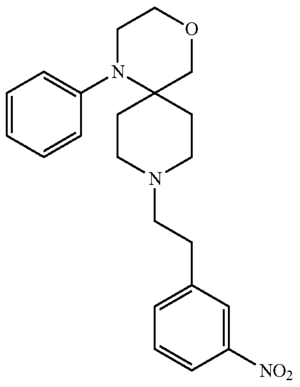 [SMILES: O=[N+]([O-])c1cccc(CCN2CCC3(CC2)COCCN3c2ccccc2)c1] | 9-(3-nitrophenethyl)-1-phenyl-4-oxa-1,9-diazaspiro[5.5]undecane | 4.84 | 382.1 |
| 42 | 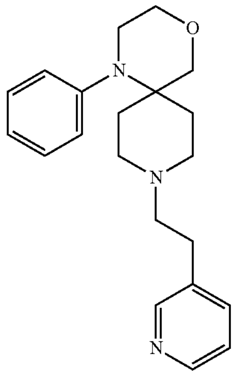 [SMILES: c1ccc(N2CCOCC23CCN(CCc2cccnc2)CC3)cc1] | 1-phenyl-9-(2-(pyridin-3-yl)ethyl)-4-oxa-1,9-diazaspiro[5.5]undecane | 3.56 | 338.2 |
| 43 | 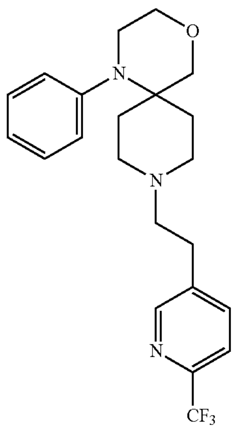 [SMILES: FC(F)(F)c1ccc(CCN2CCC3(CC2)COCCN3c2ccccc2)cn1] | 1-phenyl-9-(2-(6-(trifluoromethyl)pyridin-3-yl)ethyl)-4-oxa-1,9-diazaspiro[5.5]undecane | 4.66 | 406.2 |

-continued

| EX | Structure | Chemical name | Ret time (min) (method A) | MS (M + H) |
|---|---|---|---|---|
| 44 | 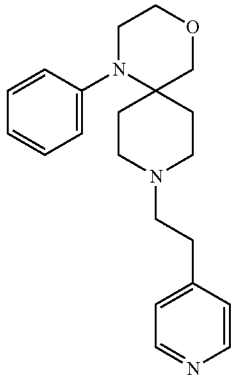 [SMILES: c1ccc(N2CCOCC23CCN(CCc2ccncc2)CC3)cc1] | 1-phenyl-9-(2-(pyridin-4-yl)ethyl)-4-oxa-1,9-diazaspiro[5.5]undecane | 3.58 | 338.2 |
| 45 | 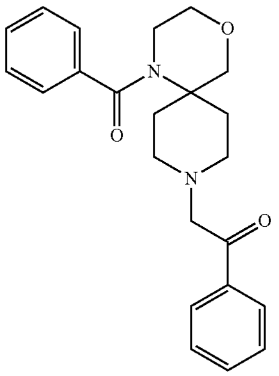 [SMILES: O=C(CN1CCC2(CC1)COCCN2C(=O)c1ccccc1)c1ccccc1] | 2-(1-benzoyl-4-oxa-1,9-diazaspiro[5.5]undecan-9-yl)-1-phenylethanone | 3.78 | 379.2 |

This method was also used for the alternative preparation of example 7 from intermediate O.

Example 46: 3-(2-(1-benzyl-4-oxa-1,9-diazaspiro[5.5]undecan-9-yl)ethyl)phenol

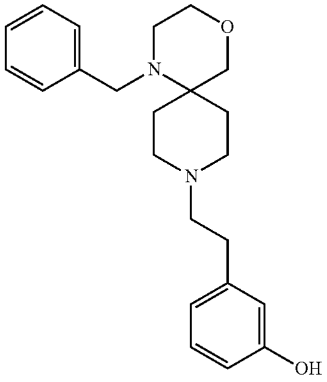 [SMILES: Oc1cccc(CCN2CCC3(CC2)COCCN3Cc2ccccc2)c1]

To a solution of example 36 (0.205 g, 0.54 mmol) in DCM (5.4 mL), boron tribromide solution (1.62 mL, 1 M in DCM, 1.62 mmol) was added dropwise at −78° C. The reaction mixture was allowed to warm to −40° C. and it was stirred at −40° C. for 1 h and then 2 h at 0° C. Then, 1 M NaOH aqueous solution was added until pH 8-9 and it was extracted with dichloromethane. The organic phases were combined, dried over $MgSO_4$, filtered and concentrated to dryness. The residue was purified by flash chromatography, silica gel, gradient DCM to MeOH:DCM (1:4) to give the title compound (0.071 g, 36% yield). HPLC retention time (method A): 4.05 min; MS: 367.2 (M+H).

This method was used for the preparation of examples 47-49 using suitable starting materials:

| EX | Structure | Chemical name | Ret time (min) (method A) | MS (M + H) |
|---|---|---|---|---|
| 47 | 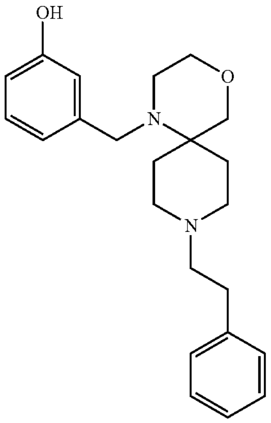 [SMILES: Oc1cccc(CN2CCOCC23CCN(CCc2ccccc2)CC3)c1] | 3-((9-phenethyl-4-oxa-1,9-diazaspiro[5.5]undecan-1-yl)methyl)phenol | 4.07 | 367.2 |
| 48 | 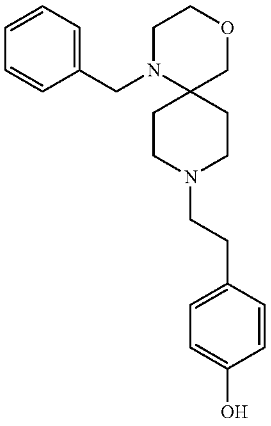 [SMILES: Oc1ccc(CCN2CCC3(CC2)COCCN3Cc2ccccc2)cc1] | 4-(2-(1-benzyl-4-oxa-1,9-diazaspiro[5.5]undecan-9-yl)ethyl)phenol | 3.95 | 367.2 |
| 49 | 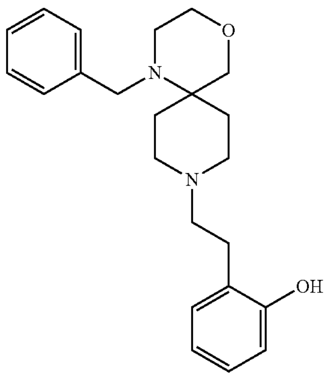 [SMILES: Oc1ccccc1CCN1CCC2(CC1)COCCN2Cc1ccccc1] | 2-(2-(1-benzyl-4-oxa-1,9-diazaspiro[5.5]undecan-9-yl)ethyl)phenol | 4.9 | 367.2 |

Example 50: (3-(2-(1-phenyl-4-oxa-1,9-diazaspiro[5.5]undecan-9-yl)ethyl)aniline

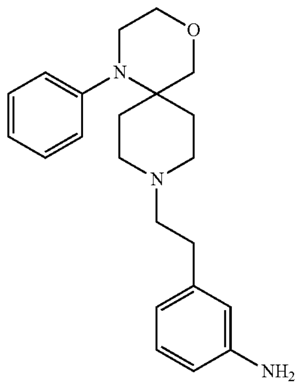

A mixture of example 41 (0.038 g, 0.093 mmol) and Pd (4 mg, 10% wt on charcoal) in MeOH (2 mL) was stirred at r.t. under 3 bars of $H_2$ overnight. Then, the solids were filtered off and the solvent was removed under vacuum to give the title compound (0.034 g, 96% yield). HPLC retention time (method A): 3.74 min; MS: 352.2 (M+H).

Example 51: (9-(2-hydroxy-2-phenylethyl)-4-oxa-1,9-diazaspiro[5.5]undecan-1-yl)(phenyl)methanone

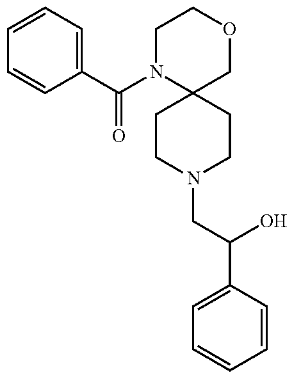 [SMILES: O=C(c1ccccc1)N1CCOCC12CCN(CC(O)c1ccccc1)CC2]

To a solution of example 45 (0.110 g, 0.29 mmol) in MeOH (1 mL) cooled at 0° C., $NaBH_4$ (22 mg, 0.58 mmol) was added. The reaction mixture was stirred at r.t. for 3 h, and then the solvent was evaporated. $NaHCO_3$ sat solution was added and it was extracted with ethyl acetate. The organic phases were combined, dried over $MgSO_4$, filtered and concentrated to dryness. The residue was purified by flash chromatography, silica gel, gradient DCM to MeOH:DCM (1:4) and then the product was filtered through an acidic ion-exchange resin (SCX cartridge), to give the title compound (0.021 g, 19% yield).

HPLC retention time (method A): 3.7 min; MS: 381.2 (M+H).

Example 52: 1-(cyclopropylmethyl)-9-phenethyl-4-oxa-1,9-diazaspiro[5.5]undecane

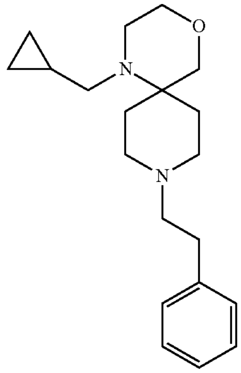 [SMILES: c1ccc(CCN2CCC3(CC2)COCCN3CC2CC2)cc1]

To a solution of example 8 (0.074 g, 0.22 mmol) in THF (1 mL), lithium aluminium hydride solution (0.9 mL, 1M in THF, 0.9 mmol) was added dropwise. The reaction mixture was stirred at 50° C. for 3 h, then at r.t. overnight. NaOH 1M aqueous solution was added, and the solids were filtered off over a pad of celite and the filter was rinsed with THF. The filtrate was concentrated to dryness and the residue was purified by flash chromatography, silica gel, gradient DCM to MeOH:DCM (1:4) to give the title compound (0.020 g, 28% yield). HPLC retention time (method A): 3.81 min; MS: 315.2 (M+H).

Table of Examples with Binding to the μ-Opioid Receptor and □$\sigma_1$-Receptor Biological Activity Pharmacological Study Human $\sigma_1$ Receptor Radioligand Assay To investigate binding properties of test compounds to human $\sigma_1$ receptor, transfected HEK-293 membranes and [$^3$H](+)-pentazocine (Perkin Elmer, NET-1056), as the radioligand, were used. The assay was carried out with 7 μg of membrane suspension, 5 nM of [$^3$H](+)-pentazocine in either absence or presence of either buffer or 10 μM Haloperidol for total and non-specific binding, respectively. Binding buffer contained Tris-HCl 50 mM at pH 8. Plates were incubated at 37° C. for 120 minutes. After the incubation period, the reaction mix was then transferred to MultiScreen HTS, FC plates (Millipore), filtered and plates were washed 3 times with ice-cold 10 mM Tris-HCL (pH7.4). Filters were dried and counted at approximately 40% efficiency in a MicroBeta scintillation counter (Perkin-Elmer) using EcoScint liquid scintillation cocktail Human μ-Opioid Receptor Radioligand Assay To investigate binding properties of test compounds to human μ-opioid receptor, transfected CHO-K1 cell membranes and [$^3$H]-DAMGO (Perkin Elmer, ES-542-C), as the radioligand, were used. The assay was carried out with 20 μg of membrane suspension, 1 nM of [$^3$H]-DAMGO in either absence or presence of either buffer or 10 μM Naloxone for total and non-specific binding, respectively. Binding buffer contained Tris-HCl 50 mM, MgCl2 5 mM at pH 7.4. Plates were incubated at 27° C. for 60 minutes. After the incubation period, the reaction mix was then transferred to MultiScreen HTS, FC plates (Millipore), filtered and plates were washed 3 times with ice-cold 10 mM Tris-HCL (pH 7.4). Filters were dried and counted at approximately 40% efficiency in a MicroBeta scintillation counter (Perkin-Elmer) using EcoScint liquid scintillation cocktail.

Results:

As this invention is aimed at providing a compound or a chemically related series of compounds which act as dual ligands of the $\sigma_1$ receptor and the μ-opiod receptor it is a very preferred embodiment in which the compounds are selected which act as dual ligands of the $\sigma_1$ receptor and the μ-opiod receptor and especially compounds which have a binding expressed as $K_i$ which is preferably <1000 nM for both receptors, more preferably <500 nM, even more preferably <100 nM.

The following scale as been adopted for representing the binding to the $\sigma_1$ receptor and the μ-opiod receptor expressed as $K_i$:

+ Both $K_i$-μ and $K_i$-$\sigma_1$>=500 nM

++ One $K_i$<500 nM while the other $K_i$ is >=500 nM

+++ Both $K_i$-μ and $K_i$-$\sigma_1$<500 nM

++++ Both $K_i$-μ and $K_i$-$\sigma_1$<100 nM

All compounds prepared in the present application exhibit binding to the $\sigma_1$ receptor and the μ-opiod receptor, in particular the following binding results are shown:

| EX | μ and $\sigma_1$ dual binding |
|---|---|
| 1 | ++ |
| 2 | +++ |
| 3 | +++ |
| 4 | +++ |
| 5 | ++ |
| 6 | ++++ |
| 7 | +++ |
| 8 | ++ |
| 9 | ++ |
| 10 | +++ |
| 11 | + |
| 12 | ++ |
| 13 | + |
| 14 | + |
| 15 | ++ |
| 16 | + |
| 17 | + |
| 18 | ++ |
| 19 | + |
| 20 | + |
| 21 | ++ |
| 22 | + |
| 23 | +++ |
| 24 | +++ |
| 25 | +++ |
| 26 | +++ |
| 27 | +++ |
| 28 | +++ |
| 29 | +++ |
| 30 | ++ |
| 31 | + |
| 32 | +++ |
| 33 | ++ |
| 34 | ++ |
| 35 | +++ |
| 36 | +++ |
| 37 | +++ |
| 38 | +++ |
| 39 | ++ |
| 40 | ++ |
| 41 | + |
| 42 | ++ |
| 43 | ++ |
| 44 | ++ |
| 45 | + |
| 46 | ++++ |
| 47 | +++ |
| 48 | ++++ |
| 49 | +++ |

-continued

| EX | μ and $\sigma_1$ dual binding |
|---|---|
| 50 | + |
| 51 | + |
| 52 | ++ |

The invention claimed is:

1. A compound of Formula (I)

(I)

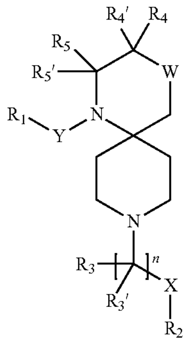

wherein n is 1,2, 3,4, 5 or 6

W is —$CR_wR_{w'}$— or —O—;

X is a bond, —C(O)— or —$CR_6R_{6'}$—;

Y is a bond or —C(O)—;

$R_1$ is substituted or unsubstituted cycloalkyl, substituted or unsubstituted aryl, substituted or unsubstituted heterocyclyl, substituted or unsubstituted alkylaryl, substituted or unsubstituted alkylheterocyclyl or substituted or unsubstituted alkylcycloalkyl;

$R_2$ is substituted or unsubstituted cycloalkyl, substituted or unsubstituted aryl, or substituted or unsubstituted heterocyclyl;

$R_w$ and $R_{w'}$ are independently selected from hydrogen, halogen, —$OR_{10}$, substituted or unsubstituted $C_{1-6}$ alkyl, substituted or unsubstituted $C_{2-6}$ alkenyl, substituted or unsubstituted $C_{2-6}$ alkynyl, haloalkyl, haloalkoxy, —$C(O)OR_{10}$, —$C(O)NR_{10}R_{10'}$, —$NR_{10}C(O)R_{10'}$, and —$NR_{10}R_{10'''}$;

wherein $R_{10}$, $R_{10'}$ and $R_{10''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{10'''}$ is selected from hydrogen, unsubstituted $C_{1-6}$ alkyl, unsubstituted $C_{2-6}$ alkenyl, unsubstituted $C_{2-6}$ alkynyl and -Boc;

$R_3$ and $R_{3'}$ are independently selected from hydrogen, substituted or unsubstituted $C_{1-6}$ alkyl, substituted or unsubstituted $C_{2-6}$ alkenyl, and substituted or unsubstituted $C_{2-6}$ alkynyl;

$R_4$ and $R_{4'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —$C(O)OR_8$, and —$C(O)NR_8R_{8'}$;

wherein $R_8$ and $R_{8'}$ are independently selected from hydrogen, unsubstituted $C_{1-6}$ alkyl, unsubstituted $C_{2-6}$ alkenyl, and unsubstituted $C_{2-6}$ alkynyl;

alternatively, $R_4$ and $R_{4'}$ may form, together with the carbon to which they are attached, a substituted or unsubstituted $C_{3-8}$ cycloalkyl;

$R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)$OR_9$, and —C(O)$NR_9R_{9'}$;

wherein $R_9$ and $R_{9'}$ are independently selected from hydrogen, unsubstituted $C_{1-6}$ alkyl, unsubstituted $C_{2-6}$ alkenyl, and unsubstituted $C_{2-6}$ alkynyl;

$R_6$ and $R_{6'}$ are independently selected from hydrogen, halogen, —$OR_7$, substituted or unsubstituted $C_{1-6}$ alkyl, substituted or unsubstituted $C_{2-6}$ alkenyl, substituted or unsubstituted $C_{2-6}$ alkynyl, —C(O)$OR_7$, —C(O)$NR_7R_{7'}$, —$NR_7$C(O) $R_{7'}$, and —$NR_7R_{7''''}$;

wherein $R_7$, $R_{7'}$ and $R_{7''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{7''''}$, is selected from hydrogen, unsubstituted $C_{1-6}$ alkyl, unsubstituted $C_{2-6}$ alkenyl, unsubstituted $C_{2-6}$ alkynyl and -Boc;

with the proviso that:

-when Y—$R_1$ and —$(CR_3R_{3'})_n$—X—$R_2$ are both unsubstituted benzyl, then none of $R_4$ and $R_{4'}$ may be hydrogen or substituted or unsubstituted methyl while the other is hydrogen, optionally as a stereoisomer, including enantiomers and diastereomers, a racemate or a mixture of at least two stereoisomers, including enantiomers and/or diastereomers, in any mixing ratio, or a corresponding salt thereof, or a corresponding solvate thereof.

2. The compound according to claim 1, wherein Y is a bond.

3. The compound according to claim 1, wherein n is 2.

4. The compound according to claim 1, wherein n is 2, X is a bond and $R_2$ is substituted or unsubstituted phenyl.

5. The compound according to claim 1, wherein $R_1$ is substituted or unsubstituted phenyl.

6. The compound according to claim 1, wherein $R_5$ and $R_{5'}$ are hydrogen.

7. The compound according to claim 1, wherein $R_3$ and $R_{3'}$ are hydrogen.

8. The compound according to claim 1, wherein $R_4$ and $R_{4'}$ are hydrogen.

9. The compound according to claim 1, wherein $R_w$ and $R_{w'}$ are hydrogen.

10. The compound according to claim 1, which is selected from the group consisting of 9-benzyl-1-phenyl-1,9-diazaspiro[5.5]undecane,
3-(9-benzyl-1,9-diazaspiro[5.5]undecan-1-yl)phenol,
9-phenethyl-1-phenyl-1,9-diazaspiro[5.5]undecane,
9-benzyl-1-(3-methoxyphenyl)-1,9-diazaspiro[5.5]undecane,
9-benzyl-1-phenyl-4-oxa-1,9-diazaspiro[5.5]undecane,
1-benzyl-9-phenethyl-4-oxa-1,9-diazaspiro[5.5]undecane,
9-phenethyl-1-phenyl-4-oxa-1,9-diazaspiro[5.5]undecane,
cyclopropyl(9-phenethyl-4-oxa-1,9-diazaspiro[5.5]undecan-1-yl)methanone,
(9-benzyl-4-oxa-1,9-diazaspiro[5.5]undecan-1-yl)(phenyl)methanone,
(9-phenethyl-4-oxa-1,9-diazaspiro[5.5]undecan-1-yl)(phenyl)methanone,
(9-phenethyl-4-oxa-1,9-diazaspiro[5.5]undecan-1-yl)(pyridin-2-yl)methanone,
(9-phenethyl-4-oxa-1,9-diazaspiro[5.5]undecan-1-yl)(thiazol-2-yl)methanone,
(9-phenethyl-4-oxa-1,9-diazaspiro[5.5]undecan-1-yl)(pyridin-4-yl)methanone,
(9-phenethyl-4-oxa-1,9-diazaspiro[5.5]undecan-1-yl)(pyridin-3-yl)methanone,
(2-fluorophenyl)(9-phenethyl-4-oxa-1,9-diazaspiro[5.5]undecan-1-yl)methanone,
(9-phenethyl-4-oxa-1,9-diazaspiro[5.5]undecan-1-yl)(thiazol-4-yl)methanone,
1-(9-phenethyl-4-oxa-1,9-diazaspiro[5.5]undecan-1-yl)-2-(pyridin-2-yl)ethanone,
2-cyclopropyl-1-(9-phenethyl-4-oxa-1,9-diazaspiro[5.5]undecan-1-yl)ethanone,
1-(9-phenethyl-4-oxa-1,9-diazaspiro[5.5]undecan-1-yl)-2-(pyridin-4-yl)ethanone,
(9-phenethyl-4-oxa-1,9-diazaspiro[5.5]undecan-1-yl)(thiazol-5-yl)methanone,
1-(9-phenethyl-4-oxa-1,9-diazaspiro[5.5]undecan-1-yl)-2-phenylethanone,
1-(9-phenethyl-4-oxa-1,9-diazaspiro[5.5]undecan-1-yl)-2-(pyridin-3-yl)ethanone,
N-(3-(2-(1-phenyl-4-oxa-1,9-diazaspiro[5.5]undecan-9-yl)ethyl)phenyl)acetamide,
9-phenethyl-1-(pyridin-4-ylmethyl)-4-oxa-1,9-diazaspiro[5.5]undecane,
1-(3-methoxybenzyl)-9-phenethyl-4-oxa-1,9-diazaspiro[5.5]undecane,
9-phenethyl-1-(pyridin-2-ylmethyl)-4-oxa-1,9-diazaspiro[5.5]undecane,
9-phenethyl-1-(pyridin-3-ylmethyl)-4-oxa-1,9-diazaspiro[5.5]undecane,
2-((9-phenethyl-4-oxa-1,9-diazaspiro[5.5]undecan-1-yl)methyl)phenol,
1,9-diphenethyl-4-oxa-1,9-diazaspiro[5.5]undecane,
1-(4-methoxybenzyl)-9-phenethyl-4-oxa-1,9-diazaspiro[5.5]undecane,
1-((3-fluoropyridin-4-yl)methyl)-9-phenethyl-4-oxa-1,9-diazaspiro[5.5]undecane,
N-(3-((9-phenethyl-4-oxa-1,9-diazaspiro[5.5]undecan-1-yl)methyl)phenyl)methanesulfonamide,
N-(4-((9-phenethyl-4-oxa-1,9-diazaspiro[5.5]undecan-1-yl)methyl)phenyl)acetamide,
1-benzyl-9-(2-(pyridin-2-yl)ethyl)-4-oxa-1,9-diazaspiro[5.5]undecane,
1-benzyl-9-(2-methoxyphenethyl)-4-oxa-1,9-diazaspiro[5.5]undecane,
1-benzyl-9-(3-methoxyphenethyl)-4-oxa-1,9-diazaspiro[5.5]undecane,
1-benzyl-9-(4-methoxyphenethyl)-4-oxa-1,9-diazaspiro[5.5]undecane,
1-benzyl-9-(2-(pyridin-3-yl)ethyl)-4-oxa-1,9-diazaspiro[5.5]undecane,
1-benzyl-9-(2-(pyridin-4-yl)ethyl)-4-oxa-1,9-diazaspiro[5.5]undecane,
1-phenyl-9-(2-(pyridin-2-yl)ethyl)-4-oxa-1,9-diazaspiro[5.5]undecane,
9-(3-nitrophenethyl)-1-phenyl-4-oxa-1,9-diazaspiro[5.5]undecane,
1-phenyl-9-(2-(pyridin-3-yl)ethyl)-4-oxa-1,9-diazaspiro[5.5]undecane,
1-phenyl-9-(2-(6-(trifluoromethyl)pyridin-3-yl)ethyl)-4-oxa-1,9-diazaspiro[5.5]undecane,
1-phenyl-9-(2-(pyridin-4-yl)ethyl)-4-oxa-1,9-diazaspiro[5.5]undecane,
2-(1-benzoyl-4-oxa-1,9-diazaspiro[5.5]undecan-9-yl)-1-phenylethanone,
3-(2-(1-benzyl-4-oxa-1,9-diazaspiro[5.5]undecan-9-yl)ethyl)phenol,
3-((9-phenethyl-4-oxa-1,9-diazaspiro[5.5]undecan-1-yl)methyl)phenol, 4-(2-(1-benzyl-4-oxa-1,9-diazaspiro[5.5]undecan-9-yl) ethyl)phenol, 2-(2-(1-benzyl-4-oxa-1,9-diazaspiro[5.5]undecan-9-yl) ethyl)phenol, 3-(2-(1-phenyl-4-oxa-1,9-diazaspiro[5.5]undecan-9-yl) ethyl)aniline, (9-(2-hydroxy-2-phenylethyl)-4-oxa-1,9-diazaspiro[5.5] undecan-1-yl)(phenyl)methanone, and 1-(cyclopropylmethyl)-9-phenethyl-4-oxa-1,9-diazaspiro [5.5]undecane.

11. A process for preparing a compound of formula I according to claim 1, (I)

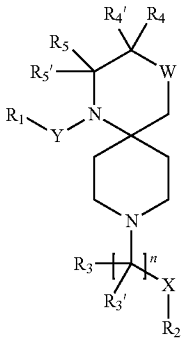

comprising a) reacting a compound of formula IVH (IVH)

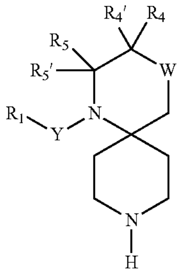

with a compound of formula V, VI or VII,

V

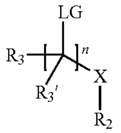

VI

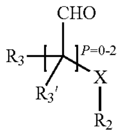

VII

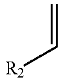

wherein p represents 0, 1 or 2, and LG represents a leaving group such as halogen, mesylate, tosylate or triflate, b) reacting a compound of formula II (II)

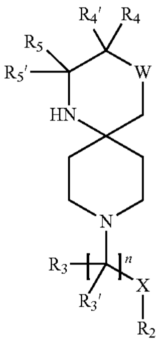

with a compound of formula (III)

$R_1Z$ (III)

wherein Z represents a leaving group, including halogen, mesylate, tosylate and triflate, or an aldehyde (CHO), or alternatively it represents COOH or COV wherein V represents halogen, or c) when $R_5$ and $R_{5'}$ are both hydrogen, by a reduction reaction of a compound of formula IX"

(IX")

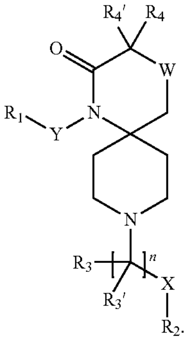

12. A method for the preparation of a compound of Formula (I) according to claim 1, employing a compound of formulae (X"), (XII'), (XIV'), (XVI'), (IXa'), XXII'), (XXIII'), IXb"), (XVIIa'), (XVIII'), (XIX'), (VIIIa'), (IIa'), (IIb'), (V), (VI) or (VII)

(X')

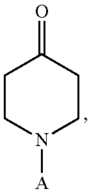

-continued
(XII')
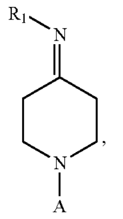
(XIV')
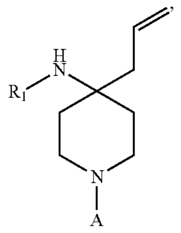
(XVI')
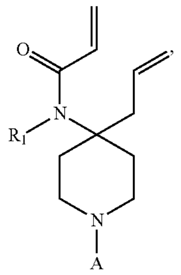
(IXa')
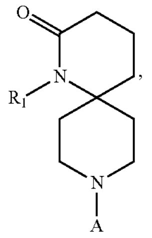
(XXII')
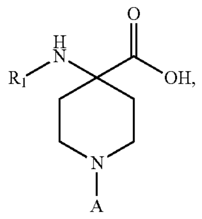
(XXIII')
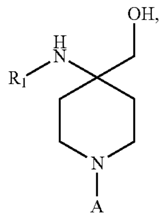
-continued
(IXb'')
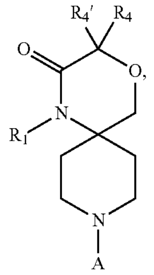
(XVIIa')
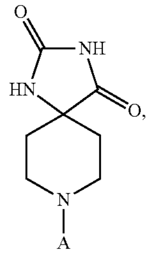
(XVIII')
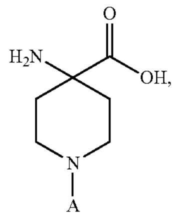
(XIX')
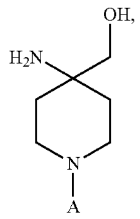
(VIIIa')
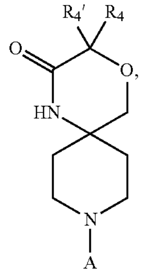
(IIa')
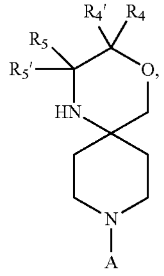

-continued (IIb')

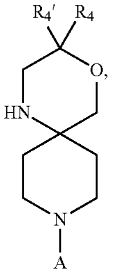

(V)

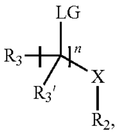

(VI)

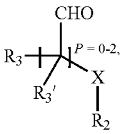

-continued (VII)

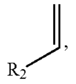

wherein A represents —$(CR_3R_{3'})_nXR_2$, hydrogen or P, wherein $R_1$, $R_2$, $R_3$, $R_{3'}$, $R_4$, $R_{4'}$, $R_5$, $R_{5'}$, n, W, X and Y have the meanings as defined in claim 1, for the compound of formula (I), p represents 0, 1 or 2, LG and Z independently represent a leaving group, including halogen, mesylate, tosylate and triflate, and P represents a suitable protecting group, including Boc.

13. A pharmaceutical composition comprising the compound according to claim 1, or a pharmaceutically acceptable salt thereof, and a pharmaceutically acceptable carrier, adjuvant or vehicle.

14. A method of treating pain in a subject in need thereof, comprising administration of an effective amount of the compound according to claim 1.

15. The method according to claim 14, wherein the pain is selected from medium to severe pain, visceral pain, chronic pain, cancer pain, migraine, inflammatory pain, acute pain, neuropathic pain, allodynia, and hyperalgesia.

* * * * *